United States Patent [19]

Swain et al.

[11] Patent Number: 5,760,184

[45] Date of Patent: Jun. 2, 1998

[54] HAPTEN-CARRIER CONJUGATES FOR USE IN DRUG-ABUSE THERAPY AND METHODS FOR PREPARATION OF SAME

[75] Inventors: Philip A. Swain, Boston; Victoria C. Schad, Cambridge; Julia L. Greenstein, West Newton; Mark A. Exley, Chestnut Hill; Barbara S. Fox, Wayland; Stephen P. Powers, Waltham; Malcolm L. Gefter, Lincoln; Thomas J. Briner, Arlington, all of Mass.

[73] Assignee: ImmuLogic, Inc., Waltham, Mass.

[21] Appl. No.: 563,673

[22] Filed: Nov. 28, 1995

Related U.S. Application Data

[63] Continuation-in-part of Ser. No. 414,971, Mar. 30, 1995, abandoned.

[51] Int. Cl.⁶ .................. C07K 16/00; A61K 39/385; A61K 39/395
[52] U.S. Cl. .................. 530/387.1; 530/389.8; 424/193.1; 424/175.1; 424/236.1; 424/261.1; 424/196.11; 424/197.11
[58] Field of Search .................. 424/193.1, 175.1, 424/196.11, 197.11, 236.1, 261.1, 204.1; 530/387.1, 389.8; 546/112

[56] References Cited

U.S. PATENT DOCUMENTS

| | | | |
|---|---|---|---|
| 3,888,886 | 6/1975 | Leute et al. | 549/260 |
| 4,045,420 | 8/1977 | Soffer et al. | 530/405 |
| 4,123,431 | 10/1978 | Soffer et al. | 546/130 |
| 4,197,237 | 4/1980 | Leute et al. | 530/389.8 |
| 4,375,414 | 3/1983 | Strahilevitz | 210/638 |
| 4,620,977 | 11/1986 | Strahilevitz | 424/193.1 |
| 4,666,837 | 5/1987 | Harford et al. | 435/69.3 |
| 4,791,067 | 12/1988 | Sheiman et al. | 436/513 |
| 4,813,924 | 3/1989 | Strahilevitz | 604/5 |
| 4,834,973 | 5/1989 | Strahilevitz | 424/175.1 |
| 5,019,384 | 5/1991 | Gefter et al. | 424/184.1 |
| 5,037,645 | 8/1991 | Strahilevitz | 424/172.1 |
| 5,256,409 | 10/1993 | Blincko | 424/175.1 |
| 5,268,276 | 12/1993 | Holmgren et al. | 435/69.1 |
| 5,283,066 | 2/1994 | Liu et al. | 424/484 |

FOREIGN PATENT DOCUMENTS

| | | |
|---|---|---|
| 0 311 383 | 12/1989 | European Pat. Off. . |
| 0 363 041 | 11/1990 | European Pat. Off. . |
| 0 613 899 A2 | 7/1993 | European Pat. Off. . |
| 2202441 | 1/1973 | Germany . |
| 2548196A1 | 7/1977 | Germany . |
| 792869 | 3/1982 | U.S.S.R. . |
| 1123704A | 11/1984 | U.S.S.R. . |
| WO 92/03163 | 3/1992 | WIPO . |
| WO 93/12111 | 6/1993 | WIPO . |
| WO 93/23076 | 11/1993 | WIPO . |
| WO 95/07992 | 3/1995 | WIPO . |
| WO 95/27786 | 10/1995 | WIPO . |

OTHER PUBLICATIONS

Carroll et al., (1994) *Pharm. News* 1:11–16.
Bonese et al., (1974)*Nature* 252:708–710.
Bagasra et al., (1992) *Immunopharmacol.* 23:173–179.
Gallacher (1994) *Immunopharm.* 27:79–81.
Killian et al., (1978) *Pharmacol. Biochem. Behavior* 9:347–352.
Pentel et al., (1991) *Drug Met. Dispositions* 19:24–28.
Landary et al., (1993) *Science* 259:1899–1901.

(List continued on next page.)

*Primary Examiner*—Ponnathapura Achutamurthy
*Assistant Examiner*—Padmashri Ponnaluri
*Attorney, Agent, or Firm*—Hale and Dorr LLP

[57] ABSTRACT

Hapten-carrier conjugates capable of eliciting anti-hapten antibodies in vivo are disclosed. Methods of preparing the hapten-carrier conjugates and therapeutic compositions are also disclosed. Where the hapten is a drug of abuse, a therapeutic composition containing the hapten-carrier conjugate is particularly useful in the treatment of drug addiction, more particularly, cocaine addiction. Passive immunization using antibodies raised against conjugates of the instant invention is also disclosed. The therapeutic composition is suitable for co-therapy with other conventional drugs.

8 Claims, 20 Drawing Sheets

OTHER PUBLICATIONS

McKenzie et al., The Journal of Immunology., vol. 133., No. 4., pp. 1818–1824, Oct. 1984.

Curreru et al. (1993) *Society for Neuroscience* 754.4 (Abstract).

Chuong et al. (1977) *Annales Pharmaceutiques Francaises* 35:257–264 (Translation).

Kovalev et al. (1979 *Khim. Farm. (USSR)* pp. 615–618 with translation.

Ambre et al. (1991) *Journal of Analytical Toxicology* 15:17–20.

Holmgren et al. (1994) *Am. J. Trop. Med. Hyg.* pp. 42–54.

Inaba, "Cocaine: Pharmacokinetics and biotransformation in man", *SFBS Symposium on Frontiers in Cocaine Research*, Quebec, Canada, Jun. 15, 1988, pp. 1154–1157.

Jatlow (1988) *The Yale Journal of Biology and Medicine* 61:105–113.

Kantack et al. (1992) *Pharm. Biochem. and Behavior* 41:415–423.

Manganaro (1994) *Int. Arch. Immunol.* 103:223–233.

Stok et al. (1994) *Vaccine* 12:521–526.

Slos (1994) *Protein Expression and Purification* 5:518–526.

Witkin (1994) *Neurosci. and Biobehav. Reviews* 18:121–142.

Jones–Witters and Witters, *Drugs and Society–A Biological Perspective*, Wadsworth Health Sciences Division, 1983, Wadsworth, Inc., Belmont, California 94002, pp. 142–147.

Witkin (1994) *Neurosci. and Biobehav. Reviews* 18121–142.

We et al. (1994) *Vaccine* 12215–222.

Wainer et al. (1972) *Science* 176:1143–1145.

Wainer et al. (19720 *Science* 178:647–648.

Spector et al. (1970) *Science* 168:1347–1348.

Wainer et al. (1973) *The Journal of Immunology* 110:667–673.

Van Vunakis et al. (1972) *The Journal of Pharmacology and Experimental Therapeutics* 180:514–521.

Spector (1971) *The Journal of Pharmacology and Experimental Therapeutics* 178:253–258.

Castro et al. (1980) *Eur. J. Biochem* 104: 331–340.

Castro et al. (1975) *Biochemical and Biophysical Research Communications* 67:583–589.

Matsushita et al. (1974) *Biochemical and Biophysical Research Communications* 57:1006–1010.

Castro et al. (1985) *Biochemical Archives* 1:173–183.

Castro et al. (1986) *Research Communications in Chemical Pathology and Pharmacology* 51:393–404.

Decato et al. (1977) *Journal of Immunological Methods* 18:201–213.

Killian et al. (1978) *Pharmacology Biochemistry & Behavior* 9:347–352.

Berkowitz (1972) *Science* 178:1290–1292.

Berkowitz et al. (1975) *Life Sciences* 15:1017–1028.

Zimmermann et al. (1976) *Proc. West. Pharmacol. Soc.* 19:260–265.

Spector et al. (1973) *Pharmacological Reviews* 25:281–291.

Spector (1976) *Biochemical Pharmacology* 25:2427–2428.

Lomax et al. (1973) *Proc. West. Pharmacol. Soc.* 16:252–256.

Wainer et al. (1973) *Nature* 241:537–538.

Miller et al. (1974) *Proc. West. Pharmacol. Soc.* 17:69–72.

Herndon (1975) *Life Sciences* 17:151–158.

Schmidt et al. (1971) *The Journal of Clinical Investigation* 50:866–871.

Colburn (1980) *Drug Method Rev.* 11:223–262.

Pentel et al. (1991) *Drug Meth. & Disp.* 19:24–28.

Kovalev et al. (1980) *Khim. Pharm.* pp. 200–204.

(−)-COCAINE

| CJ# | BRANCH | VARIABLES |
|---|---|---|
| CJ 0 | Q | Q = H, OH, CH$_2$, HALOGEN, COOH, CARRIER PROTEIN, MODIFIED CARRIER PROTEIN |
| CJ 1 | (CH$_2$)$_n$Q | Q = H, COOH, HALOGEN, 2-NITRO-4-SULFOPHENYL ESTER, N-OXYSUCCINIMIDYL ESTER, CARRIER PROTEIN, MODIFIED CARRIER PROTEIN, CJ 1.2 |
| CJ 1.1 | CO$_2$Q | Q = H, CH$_3$ |
| CJ 1.2 | COQ | Q = H, HALOGEN, 1-OXY-2-NITRO-4-SULFOPHENYL, N-OXYSUCCINIMIDYL, N-MALEIMIDYL, CARRIER PROTEIN CJ 10 |
| CJ 2 | OCO(CH$_2$)$_n$Q | Q = COOH, HALOGEN, 2-NITRO-4-SULFOPHENYL ESTER N-OXYSUCCINIMIDYL ESTER, CARRIER PROTEIN, MODIFIED CARRIER PROTEIN |
| CJ 2.1 | OCOCH=Q | Q = H |
| CJ 2.2 | OCOCH(O)CH$_2$ | |
| CJ 2.3 | OCO(CH$_2$)$_n$CH(O)CH$_2$ | |
| CJ 3 | CO(CH$_2$)$_n$COQ | Q = H, OH, HALOGEN, 1-OXY-2-NITRO-4-SULFOPHENYL, N-OXYSUCCINIMIDYL, N-MALEIMIDYL, CARRIER PROTEIN, CJ 10 |
| CJ 3.1 | CO(CH$_2$)$_n$CNQ | Q = OCH$_3$ OR CARRIER PROTEIN |
| CJ 4 | OCO(CH$_2$)$_n$COQ | Q = H, OH, HALOGEN, 1-OXY-2-NITRO-4-SULFOPHENYL, N-OXYSUCCINIMIDYL, N-MALEIMIDYL, CARRIER PROTEIN, CJ 10 |
| CJ 4.1 | CO(CH$_2$)$_n$CNQ | Q = OCH$_3$ OR CARRIER PROTEIN |
| CJ 5 | CH$_2$OCO(CH$_2$)$_n$COQ | Q = H, OH, HALOGEN, 1-OXY-2-NITRO-4-SULFOPHENYL, N-OXYSUCCINIMIDYL, N-MALEIMIDYL, CARRIER PROTEIN CJ 10 |
| CJ 5.1 | CO(CH$_2$)$_n$CNQ | Q = OCH$_3$ OR CARRIER PROTEIN |
| CJ 6 | CONH(CH$_2$)$_n$Q | Q = H, COOH, HALOGEN, 2-NITRO-4-SULFOPHENYL ESTER, N-OXYSUCCINIMIDYL ESTER, CARRIER PROTEIN, MODIFIED CARRIER PROTEIN |
| CJ 7 | Y(CH$_2$)$_n$Q | Y = S, O, NH; Q = HALOGEN, COOH, CARRIER PROTEIN, MODIFIED CARRIER PROTEIN |
| CJ 7.1 | CH$_2$Y(CH$_2$)$_n$Q | Y = S, O, NH; Q = HALOGEN, COOH, CARRIER PROTEIN, MODIFIED CARRIER PROTEIN |
| CJ 8 | OCOCH(OH)CH$_2$Q | Q = CARRIER PROTEIN, MODIFIED CARRIER PROTEIN |
| CJ 8.1 | OCO(CH$_2$)$_n$CH(OH)CH$_2$Q | Q = CARRIER PROTEIN, MODIFIED CARRIER PROTEIN |
| CJ 9 | OCOC$_6$H$_5$ | |

*FIG. 2A*

ALTERNATIVE REPRESENTATION FOR SELECTED BRANCHES
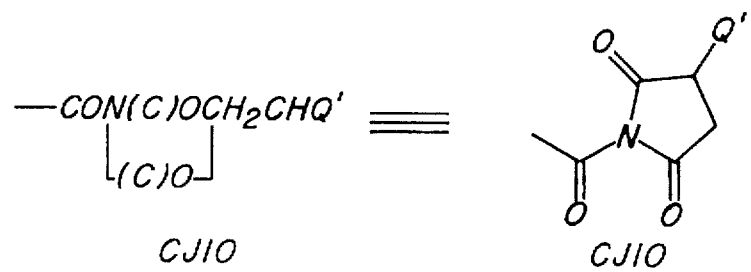
CJ10
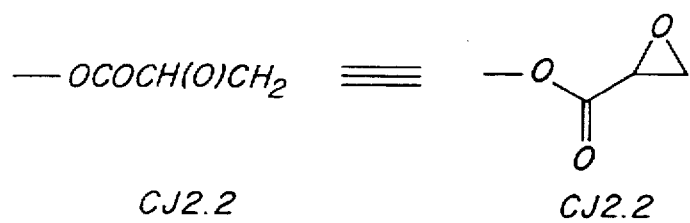
CJ2.2
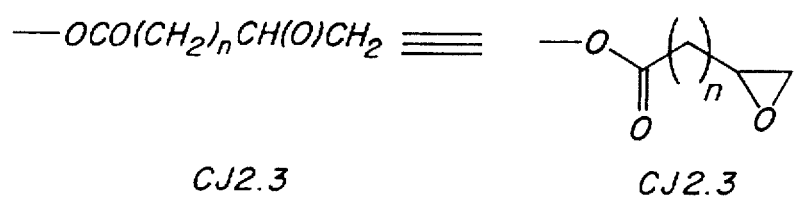
CJ2.3
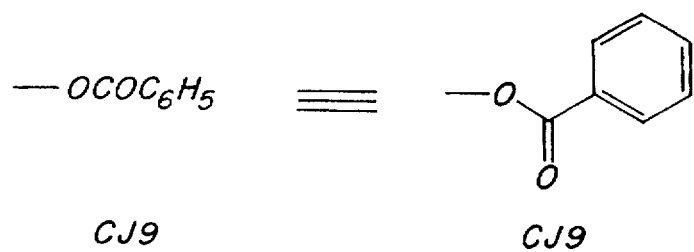
CJ9
*FIG. 2B*

| BRANCHES | A | B | C | D | E | F |
|---|---|---|---|---|---|---|
| PS-2 | CJ1.1 WHERE Q=CH₃ | CJ2 WHERE Q=HALOGEN OR MODIFIED T CELL EPITOPE CONTAINING CARRIER & n=1 | CJ0 WHERE Q=H | CJ0 WHERE Q=H | CJ0 WHERE Q=H | CJ1 WHERE Q=H, n=1 |
| PS-3 | CJ1.1 WHERE Q=CH₃ | CJ0 WHERE Q=MODIFIED T CELL EPITOPE CONTAINING CARRIER | CJ0 WHERE Q=H | CJ0 WHERE Q=H | CJ0 WHERE Q=H | CJ1 WHERE Q=H, n=1 |
| PS-4 | CJ1.1 WHERE Q=CH₃ | CJ4 WHERE Q=MODIFIED T CELL EPITOPE CONTAINING CARRIER & n=1 | CJ0 WHERE Q=H | CJ0 WHERE Q=H | CJ0 WHERE Q=H | CJ1 WHERE Q=H, n=1 |
| PS-5 | CJ1.1 WHERE Q=CH₃ | CJ9 | CJ0 WHERE Q=H | CJ0 WHERE Q=H | CJ0 WHERE Q=H | CJ3 WHERE Q=CARRIER PROTEIN AND n=2 |
| PS-6 | CJ5 WHERE Q=CARRIER PROTEIN AND n=2 | CJ9 | CJ0 WHERE Q=H | CJ0 WHERE Q=H | CJ0 WHERE Q=H | CJ1 WHERE Q=H AND n=1 |
| PS-9 | CH1.2 WHERE Q=CARRIER PROTEIN | CJ9 | CJ0 WHERE Q=H | CJ0 WHERE Q=H | CJ0 WHERE Q=H | CJ1 WHERE Q=H AND n=1 |
| PS-10 | CJ6 WHERE Q=H OR CJ 1.1 WHERE Q=CH₃ | CJ2 WHERE Q=HALOGEN | CJ0 WHERE Q=H | CJ0 WHERE Q=H | CJ0 WHERE Q=H | CJ1 WHERE Q=H AND n=1 |
| PS-11 | CJ6 WHERE Q=H OR CJ 1.1 WHERE Q=CH₃ | CJ2 WHERE Q=MODIFIED T CELL EPITOPE CONTAINING CARRIER | CJ0 WHERE Q=H | CJ0 WHERE Q=H | CJ0 WHERE Q=H | CJ1 WHERE Q=H, n=1 |
| PS-12 | CJ6 WHERE Q=H OR CJ 1.1 WHERE Q=CH₃ | CJ2.1 | CJ0 WHERE Q=H | CJ0 WHERE Q=H | CJ0 WHERE Q=H | CJ1 WHERE Q=H, n=1 |
| PS-13 | CJ6 WHERE Q=H OR CJ 1.1 WHERE Q=CH₃ | CJ20=CARRIER PROTEIN OR MODIFIED T CELL EPITOPE CONTAINING CARRIER AND n=2 | CJ0 WHERE Q=H | CJ0 WHERE Q=H | CJ0 WHERE Q=H | CJ1 WHERE Q=H, n=1 |
| PS-14 | CJ6 WHERE Q=H OR CJ 1.1 WHERE Q=CH₃ | CJ2.2 | CJ0 WHERE Q=H | CJ0 WHERE Q=H | CJ0 WHERE Q=H | CJ1 WHERE Q=H, n=1 |
| PS-15 | CJ6 WHERE Q=H OR CJ 1.1 WHERE Q=CH₃ | CJ8 | CJ0 WHERE Q=H | CJ0 WHERE Q=H | CJ0 WHERE Q=H | CJ1 WHERE Q=H, n=1 |
| PS-16 | CJ6 WHERE Q=H OR CJ 1.1 WHERE Q=CH₃ | CJ2.3 | CJ0 WHERE Q=H | CJ0 WHERE Q=H | CJ0 WHERE Q=H | CJ1 WHERE Q=H, n=1 |
| PS-17 | CJ6 WHERE Q=H OR CJ 1.1 WHERE Q=CH₃ | CJ8.1 | CJ0 WHERE Q=H | CJ0 WHERE Q=H | CJ0 WHERE Q=H | CJ1 WHERE Q=H, n=1 |

PRECURSORS / CONJUGATES

FIG. 3B(1)

| | BRANCHES | | | | | |
|---|---|---|---|---|---|---|
| | | CJ 4 | CJ J O WHERE Q=H | | | |
| PS-18 | CJ 6 WHERE Q=H, OR CJ 1.1 WHERE Q=CH₃ | | CJ O WHERE Q=H | CJ O WHERE Q=H | CJ O WHERE Q=H | CJ 1 WHERE Q=H, n=1 |
| PS-19 | CJ 6 WHERE Q=H, OR CJ 1.1 WHERE Q=CH₃ | CJ 1 WHERE Q=COOH, HALOGEN, 2-NITRO-4-SULFOPHENYL ESTER, N-OXYSUCCINIMIDYL ESTER, CARRIER PROTEIN OR MODIFIED CARRIER | CJ O WHERE Q=H | CJ O WHERE Q=H | CJ O WHERE Q=H | CJ 1 WHERE Q=H, n=1 |
| PS-20 | CJ 6 WHERE Q=H, OR CJ 1.1 WHERE Q=CH₃ | CJ 7 | CJ O WHERE Q=H | CJ O WHERE Q=H | CJ O WHERE Q=H | CJ 1 WHERE Q=H, n=1 |
| PS-21 | CJ 6 WHERE Q=H, OR CJ 1.1 WHERE Q=CH₃ | CJ 9 | CJ O WHERE Q=H | CJ O WHERE Q=H | CJ O WHERE Q=H | CJ 3 |
| PS-22 | CJ 6 WHERE Q=H, OR CJ 1.1 WHERE Q=CH₃ | CJ 9 | CJ O WHERE Q=H | CJ O WHERE Q=H | CJ O WHERE Q=H | CJ 1 WHERE Q=CJ 1.2 |
| PS-23 | CJ 5 | CJ 9 | CJ O WHERE Q=H | CJ O WHERE Q=H | CJ O WHERE Q=H | CJ 1 WHERE Q=H |
| PS-24 | CJ 7.1 | CJ 9 | CJ O WHERE Q=H | CJ O WHERE Q=H | CJ O WHERE Q=H | CJ 1 WHERE Q=H |
| PS-25 | CJ 7 | CJ 9 | CJ O WHERE Q=H | CJ O WHERE Q=H | CJ O WHERE Q=H | CJ 1 WHERE Q=H |
| PS-26 | CJ 1.2 | CJ 9 | CJ O WHERE Q=H | CJ O WHERE Q=H | CJ O WHERE Q=H | CJ 1 WHERE Q=H |
| PS-27 | CJ 6 WHERE Q=H, OR CJ 1.1 WHERE Q=CH₃ | CJ 9 | CJ 2 | CJ O WHERE Q=H | CJ O WHERE Q=H | CJ 1 WHERE Q=H, n=1 |
| PS-28 | CJ 6 WHERE Q=H, OR CJ 1.1 WHERE Q=CH₃ | CJ 9 | CJ 1 WHERE Q=COOH, HALOGEN, 2-NITRO-4-SULFOPHENYL ESTER, N-OXYSUCCINIMIDYL ESTER, CARRIER PROTEIN, MODIFIED T CELL EPITOPE CONTAINING CARRIER, CJ 1.2 | CJ O WHERE Q=H | CJ O WHERE Q=H | CJ 1 WHERE Q=H, n=1 |
| PS-29 | CJ 6 WHERE Q=H, OR CJ 1.1 WHERE Q=CH₃ | CJ 9 | CJ 2.2 | CJ O WHERE Q=H | CJ O WHERE Q=H | CJ 1 WHERE Q=H |
| PS-30 | CJ 6 WHERE Q=H, OR CJ 1.1 WHERE Q=CH₃ | CJ 9 | CJ 8 | CJ O WHERE Q=H | CJ O WHERE Q=H | CJ 1 WHERE Q=H |
| PS-31 | CJ 6 WHERE Q=H, OR CJ 1.1 WHERE Q=CH₃ | CJ 9 | CJ 2.3 | CJ O WHERE Q=H | CJ O WHERE Q=H | CJ 1 WHERE Q=H |

PRECURSORS / CONJUGATES

FIG. 3B(2)

| PRECURSORS/CONJUGATES | BRANCHES | | | | | |
|---|---|---|---|---|---|---|
| PS-32 | CJ 6 WHERE Q=H, OR CJ 1.1 WHERE Q=CH3 | CJ9 | CJ8.1 | CJ 0 WHERE Q=H | CJ 0 WHERE Q=H | CJ1 WHERE Q=H, n=1 |
| PS-33 | CJ 6 WHERE Q=H, OR CJ 1.1 WHERE Q=CH3 | CJ9 | CJ4 | CJ 0 WHERE Q=H | CJ 0 WHERE Q=H | CJ1 WHERE Q=H, n=1 |
| PS-34 | CJ 6 WHERE Q=H, OR CJ 1.1 WHERE Q=CH3 | CJ9 | CJ5 | CJ 0 WHERE Q=H | CJ 0 WHERE Q=H | CJ1 WHERE Q=H, n=1 |
| PS-35 | CJ 6 WHERE Q=H, OR CJ 1.1 WHERE Q=CH3 | CJ9 | CJ 0 WHERE Q=H | CJ2 | CJ 0 WHERE Q=H | CJ1 WHERE Q=H, n=1 |
| PS-36 | CJ 6 WHERE Q=H, OR CJ 1.1 WHERE Q=CH3 | CJ9 | CJ 0 WHERE Q=H | CJ1 WHERE Q=COOH, HALOGEN, 2-NITRO-4-SULFOPHENYL ESTER, N-OXYSUC-CINIMIDYL ESTER, CARRIER PROTEIN, MODIFIED T CELL EPITOPE CONTAIN-ING CARRIER,CJ1.2 | CJ 0 WHERE Q=H | CJ1 WHERE Q=H, n=1 |
| PS-37 | CJ 6 WHERE Q=H, OR CJ 1.1 WHERE Q=CH3 | CJ9 | CJ 0 WHERE Q=H | CJ 2.2 | CJ 0 WHERE Q=H | CJ1 WHERE Q=H, n=1 |
| PS-38 | CJ 6 WHERE Q=H, OR CJ 1.1 WHERE Q=CH3 | CJ9 | CJ 0 WHERE Q=H | CJ 8 | CJ 0 WHERE Q=H | CJ1 WHERE Q=H, n=1 |
| PS-39 | CJ 6 WHERE Q=H, OR CJ 1.1 WHERE Q=CH3 | CJ9 | CJ 0 WHERE Q=H | CJ 2.3 | CJ 0 WHERE Q=H | CJ1 WHERE Q=H, n=1 |
| PS-40 | CJ 6 WHERE Q=H, OR CJ 1.1 WHERE Q=CH3 | CJ9 | CJ 0 WHERE Q=H | CJ 8.1 | CJ 0 WHERE Q=H | CJ1 WHERE Q=H, n=1 |
| PS-41 | CJ 6 WHERE Q=H, OR CJ 1.1 WHERE Q=CH3 | CJ9 | CJ 0 WHERE Q=H | CJ 4 | CJ 0 WHERE Q=H | CJ1 WHERE Q=H, n=1 |
| PS-42 | CJ 6 WHERE Q=H, OR CJ 1.1 WHERE Q=CH3 | CJ9 | CJ 0 WHERE Q=H | CJ 5 | CJ 0 WHERE Q=H | CJ1 WHERE Q=H, n=1 |
| PS-43 | CJ 6 WHERE Q=H, OR CJ 1.1 WHERE Q=CH3 | CJ9 | CJ 0 WHERE Q=H | CJ 0 WHERE Q=H | CJ 2 | CJ1 WHERE Q=H, n=1 |
| PS-44 | CJ 6 WHERE Q=H, OR CJ 1.1 WHERE Q=CH3 | CJ9 | CJ 0 WHERE Q=H | CJ 0 WHERE Q=H | CJ1 WHERE Q=COOH, HALOGEN, 2-NITRO-4-SULFOPHENYL ESTER, CARRIER N-OXYSUCCINIMIDYL ESTER, CARRIER PROTEIN, MODIFIED T CELL EPITOPE CONTAINING CARRIER, CJ1.2 | CJ1 WHERE Q=H, n=1 |

PRECURSORS / CONJUGATES

| | BRANCHES | | | |
|---|---|---|---|---|
| PS-45 | CJ6 WHERE Q=H, OR CJ 1.1 WHERE Q=CH3 | CJ9 | CJ0 WHERE Q=H | CJ0 WHERE Q=H | CJ2.2 | CJ1 WHERE Q=H, n=1 |
| PS-46 | CJ6 WHERE Q=H, OR CJ 1.1 WHERE Q=CH3 | CJ9 | CJ0 WHERE Q=H | CJ0 WHERE Q=H | CJ8 | CJ1 WHERE Q=H, n=1 |
| PS-47 | CJ6 WHERE Q=H, OR CJ 1.1 WHERE Q=CH3 | CJ9 | CJ0 WHERE Q=H | CJ0 WHERE Q=H | CJ2.3 | CJ1 WHERE Q=H, n=1 |
| PS-48 | CJ6 WHERE Q=H, OR CJ 1.1 WHERE Q=CH3 | CJ9 | CJ0 WHERE Q=H | CJ0 WHERE Q=H | CJ8.1 | CJ1 WHERE Q=H, n=1 |
| PS-49 | CJ6 WHERE Q=H, OR CJ 1.1 WHERE Q=CH3 | CJ9 | CJ0 WHERE Q=H | CJ0 WHERE Q=H | CJ4 | CJ1 WHERE Q=H, n=1 |
| PS-50 | CJ6 WHERE Q=H, OR CJ 1.1 WHERE Q=CH3 | CJ9 | CJ0 WHERE Q=H | CJ0 WHERE Q=H | CJ5 | CJ1 WHERE Q=H, n=1 |

FIG. 4

| | A | B | C | D | E | F |
|---|---|---|---|---|---|---|
| COCAINE | CJ1.1 WHERE Q=CH3 | CJ9 | CJ0 WHERE Q=H | CJ0 WHERE Q=H | CJ0 WHERE Q=H | CJ1 WHERE Q=H, n=1 |
| ECGONINE METHYL ESTER | CJ1.1 WHERE Q=CH3 | CJ10 WHERE Q=OH | CJ0 WHERE Q=H | CJ0 WHERE Q=H | CJ0 WHERE Q=H | CJ1 WHERE Q=H, n=1 |
| NORCOCAINE | CJ1.1 WHERE Q=CH3 | CJ9 | CJ0 WHERE Q=H | CJ0 WHERE Q=H | CJ0 WHERE Q=H | CJ0 WHERE Q=H |
| BENZOYL ECGONINE | CJ0 WHERE Q=COOH | CJ9 | CJ0 WHERE Q=H | CJ0 WHERE Q=H | CJ0 WHERE Q=H | CJ1 WHERE Q=H, n=1 |

OTHER COMMONLY ABUSED DRUGS
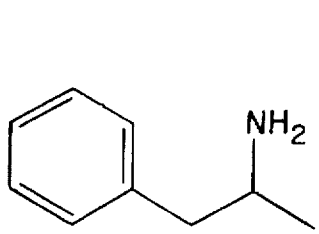
AMPHETAMINE
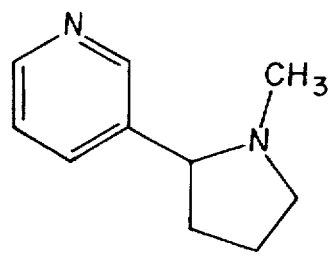
NICOTINE
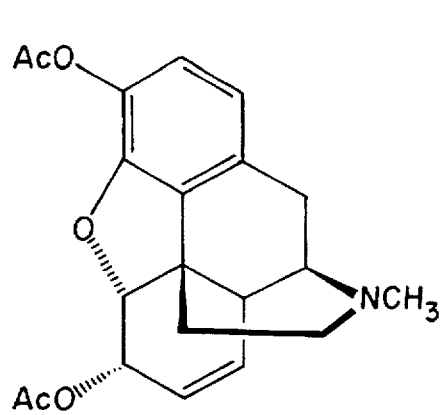
HEROIN
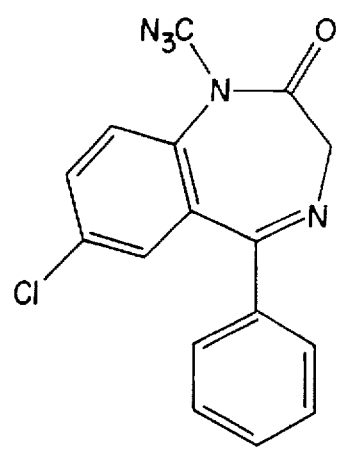
DIAZEPAM
*FIG. 6*

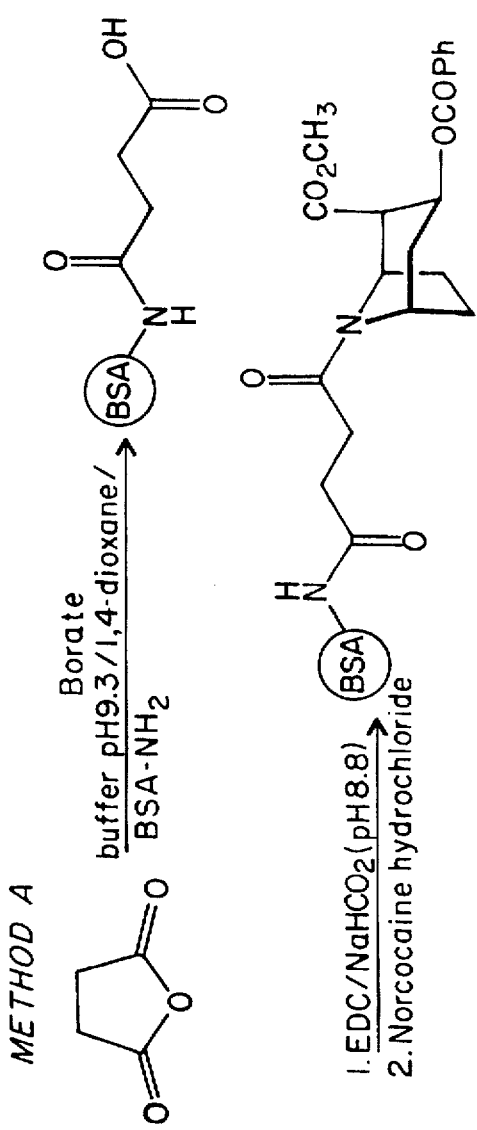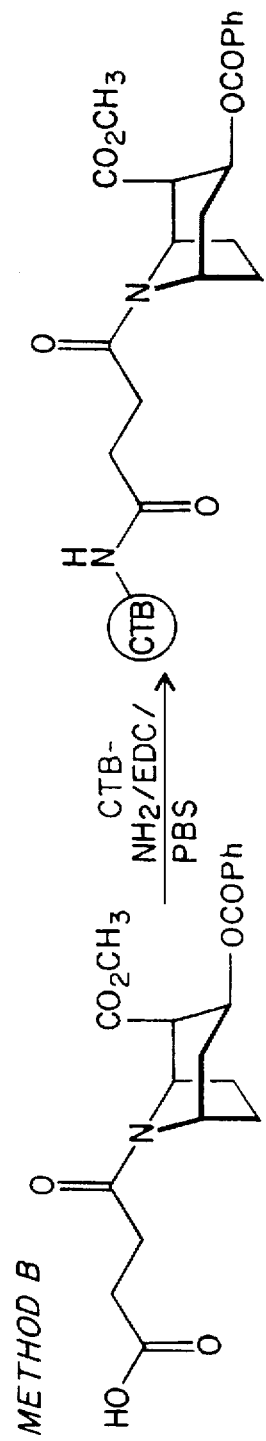
FIG. 7A
FIG. 7B

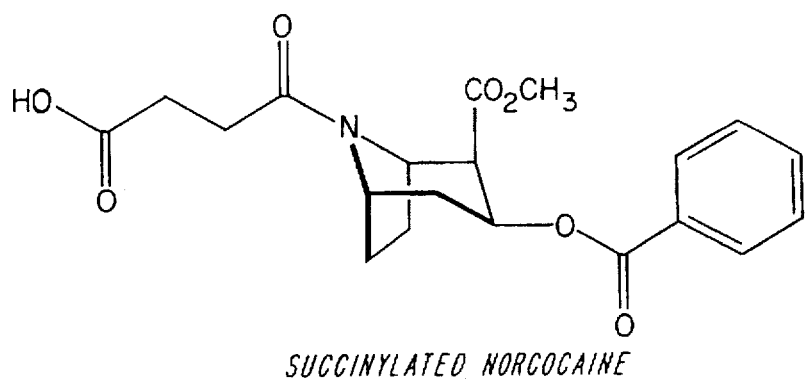
SUCCINYLATED NORCOCAINE
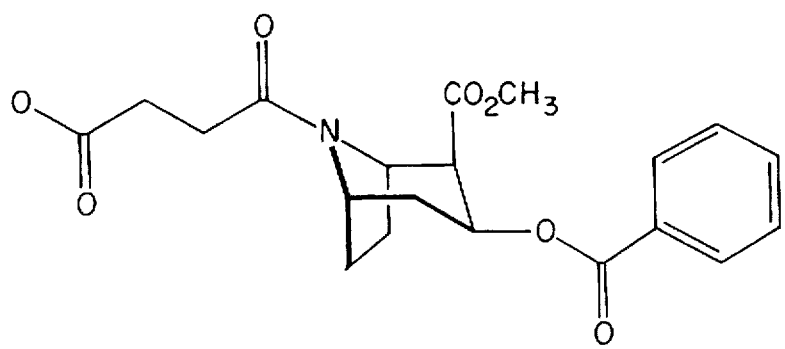
PRE-ACTIVATED SUCCINYALTED NORCOCAINE
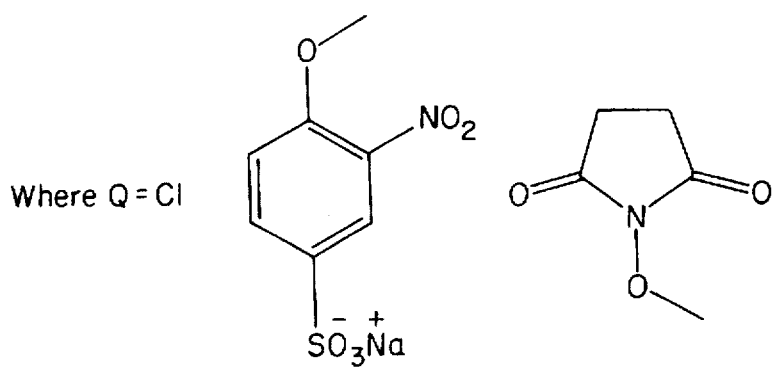
FIG. 8

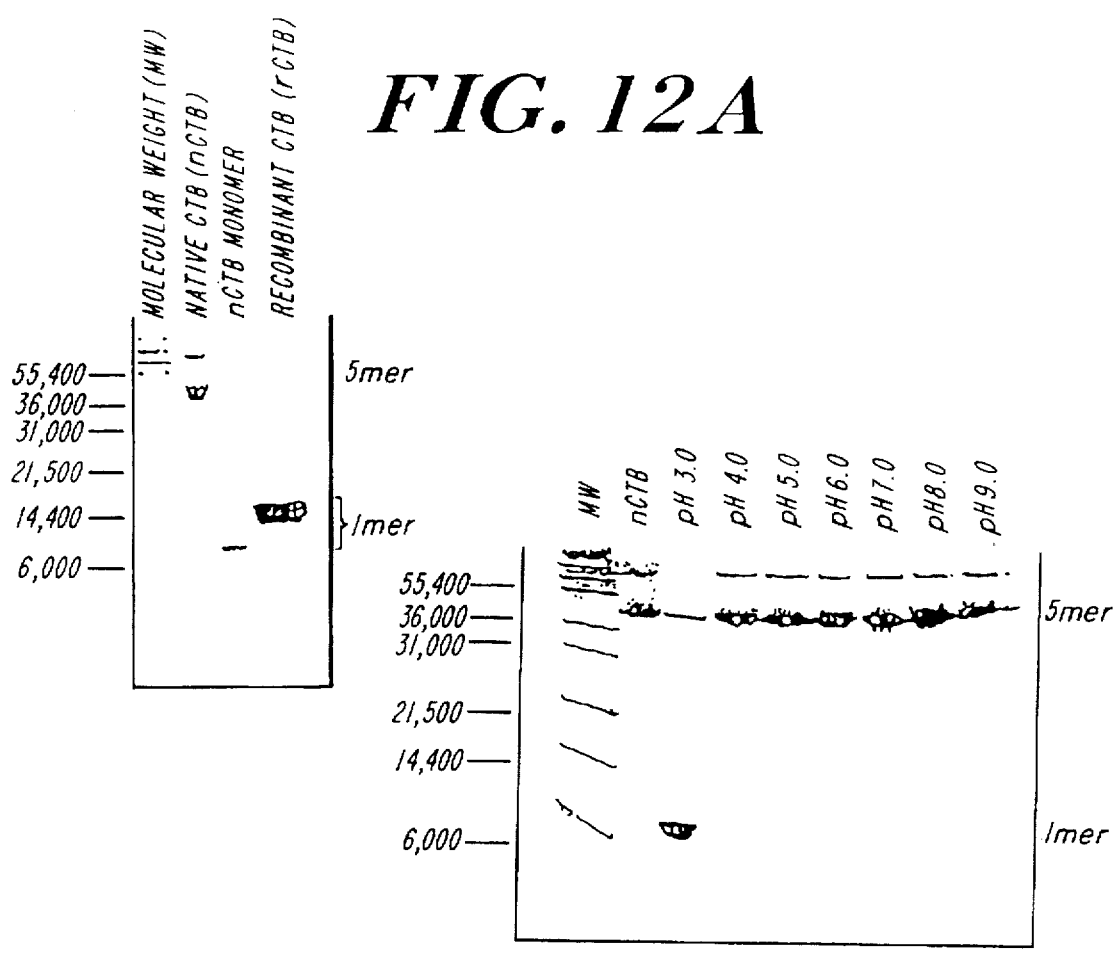
FIG. 12A
FIG. 12B
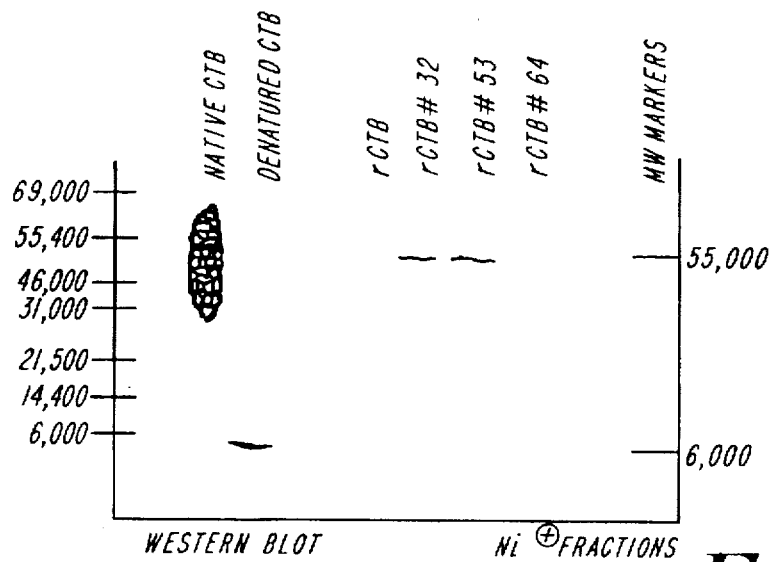
FIG. 12C

HAPTEN-CARRIER CONJUGATES FOR USE IN DRUG-ABUSE THERAPY AND METHODS FOR PREPARATION OF SAME

REFERENCE TO RELATED APPLICATION

This application is a continuation-in-part of patent application Ser. No. 08/414,971, entitled "Hapten-Carrier Conjugates For Use In Drug-Abuse Therapy and Methods For Preparation of Same", filed Mar. 30, 1995 now abandoned.

FIELD OF THE INVENTION

The present invention relates to treatment of drug abuse. More specifically, the present invention relates to methods of treating drug abuse using drug-hapten carrier conjugates which elicit antibody responses and/or using the antibodies to the drug-hapten carrier conjugates.

BACKGROUND OF THE INVENTION

The prevalence of drug use and abuse worldwide, especially in the United States, has reached epidemic levels. There are a plethora of drugs, both legal and illegal, the abuse of which have become serious public policy issues affecting all strata of society with its obvious medical and social consequences. Some users live in an extremely high risk population associated with poverty and illegal activity. Other users who might classify themselves as recreational users are at risk due to (a) properties of the drug(s) which make them addictive, (b) a predisposition of the user to become a heavy user or (c) a combination of factors including personal circumstances, hardship, environment and accessibility. Adequate treatment of drug abuse, including polydrug abuse, requires innovative and creative programs of intervention.

An especially problematic drug is cocaine, an alkaloid derived from the leaves of the coca plant (*Erythroxylon coca*). In the United States alone, there currently are more than 5 million regular cocaine users of whom at least 600,000 are classified as severely addicted (Miller et al. (1989) *N.Y. State J. Med.* pp. 390–395; and Carroll et al. (1994) *Pharm. News.* 1:11–16). Within this population, a significant number of addicts actively are seeking therapy. For example, in 1990, 380,000 people sought medical treatment for cocaine addiction and the number is increasing. At that time, it was estimated that 100,000 emergency room admissions per year involve cocaine use. The cumulative effects of cocaine-associated violent crime, loss in individual productivity, illness, and death is an international problem.

The lack of effective therapies for the treatment of cocaine addiction strongly suggests that novel approaches must be developed. Additional factors contributing to the lack of successful treatment programs is that patterns of cocaine abuse have varied with time. In an article entitled "1994 Chemical Approaches to the Treatment of Cocaine Abuse" (Carroll et al. (1994) *Pharm. News,* Vol. 1, No. 2), Carroll et al. report that since the mid-1980's, intravenous and nasal dosing of the hydrochloride salt (coke, snow, blow) and smoking of cocaine free-base (crack) have become common routes of administration, producing euphoria and psychomotor stimulation which last 30–60 minutes. Unlike some other abused drugs, cocaine can be taken in binges lasting for several hours. This behavior leads to addiction, and in some cases, to toxic consequences (Carroll et al., *Pharm. News,* supra.).

There are only very limited treatments for drugs of abuse and no effective long term treatments for cocaine addiction.

Treatments include, but are not limited to, counseling coupled with the administration of drugs that act as antagonists at the opioid receptors or drugs that try to reduce the craving associated with drug addiction. One approach to treatment is detoxification. Even temporary remissions with attendant physical, social and psychological improvements are preferable to the continuation or progressive acceleration of abuse and its related adverse medical and interpersonal consequences (Wilson et al. in *Harrison's Principle Of Internal Medicine* Vol. 2, 12th Ed., McGraw-Hill (1991) pp. 2157–8). More specifically, pharmacological approaches to the treatment of cocaine abuse generally involve the use of anti-depressant drugs, such as desipramine or fluoxetine which may help manage the psychological aspects of withdrawal but, in general, do not directly affect the physiology of cocaine. Further, their effectiveness varies widely (Brooke et al. (1992) *Drug Alcohol Depend.* 31:37–43). In some studies, desipramine reduced self-administration (Tella (1994) *College on Problems of Drug Dependence Meeting Abstracts*; Mello et al. (1990) *J. Pharmacol. Exp. Ther.* 254:926–939; and Kleven et al. (1990) *Behavl. Pharmacol.* 1:365–373), but abstinence rate following treatment did not exceed 70% (Kosten (1993) *Problems of Drug Dependence, NIDA Res. Monogr.* 85). There has also been the use of drugs which potentiate dopaminergic transmission, such as bromocriptine, but the benefits of such drugs are limited in part by toxicity (Taylor et al. (1990) *West. J. Med.* 152:573–577). New drugs aimed at replacing methadone for opioid addiction, such as buprenorphine, have also been used based on cross-interference with the dopaminergic system, however only limited clinical study information is available (Fudula et al. (1991) NIDA *Research Monograph,* 105:587–588). Buprenorphine has been reported to decrease cocaine self-administration (Carroll et al. (1991) *Psychopharmacology* 106:439–446; Mello et al. (1989) *Science* 245:859–862; and Mello et al. (1990) J. Pharmacol. Exp. Ther. 254:926–939); however, cocaine abstinence rates following treatment generally do not exceed 50% (Gastfried et al. (1994) *College on Problems of Drug Dependence Meeting Abstracts*; and Schottenfeld et al. (1993) *Problems on Drug Dependence, NIDA Res. Monogr.* 311).

Present therapies used to treat cocaine addicts have at least four major limitations leading to a very high rate of recidivism. First, and perhaps most fundamentally, the contributing neurochemical events in cocaine abuse and addiction are complex (Carroll et al. (1994) supra.). As a result, single acting neuropharmacological approaches, such as inhibition of dopamine uptake, do not appear to be sufficient to overcome addiction. Second, the drugs currently used in cocaine addiction treatments have significant side-effects themselves, limiting their utility. Third, drug therapy compliance is problematic among this patient population. Current therapies can require frequent visits to a health care provider and/or self-administration of drugs designed to cure the addict of his habit. Because many of these drugs prevent the euphoria associated with cocaine, there is a strong disincentive to taking the drug. (Carroll, et al. (1994) supra.; Kosten et al. (1993) Problems of Drug Dependence, *NIDA Res. Monogr.* 132:85; Schottenfeld et al. (1993) Problems of Drug Dependence, *NIDA Res. Monogr.* 132:311.) Fourth, because of the complex chemistries involved in pharmacological therapies, many of them may be incompatible with other therapies currently in use or in clinical trials.

Experimental diagnostic approaches and therapies have been suggested in the literature which have yet to be practiced. For example, vaccination as a therapeutic approach for drug addiction has been described previously in principle. Bonese et al. investigated changes in heroin self-administration by a rhesus monkey after immunization against morphine (Bonese et al. (1974) *Nature* 252: 708–710). Bagasra et al. investigated using cocaine-KLH vaccination as a means to prevent addiction (*Immunopharmacol.* (1992) 23:173–179). Rats were immunized with cocaine-KLH conjugate which raised some anti-cocaine antibodies. However, these results are in dispute (Gallacher (1994) *Immunopharm.* 27:79–81). Obviously, if a conjugate is to be effective in a therapeutic regimen, it must be capable of raising antibodies that can recognize free cocaine circulating in vivo. Cerny (WO 92/03163) describes a vaccine and immunoserum against drugs. The vaccine is comprised of a hapten bonded to a carrier protein to produce antibodies. Also disclosed is the production of antibodies against drugs, and the use of these antibodies in the detoxification of one who has taken the drug.

Passive administration of monoclonal antibodies to treat drug abuse has been previously described (see, Killian et al. (1978) *Pharmacol. Biochem. Behavior* 9:347–352; Pentel et al. (1991) *Drug Met. Disposition* 19:24–28). In this approach, pre-formed antibodies to selected drugs are passively administered to animals. While these data provide a demonstration of the feasibility of immunological approaches to addiction therapy, passive immunization as a long term human therapeutic strategy suffers from a number of major drawbacks. First, if antibodies to be used for passive therapy are from non-human sources or are monoclonal antibodies, these preparations will be seen as foreign proteins by the patient, and there may be a rapid immune response to the foreign antibodies. This immune response may neutralize the passively administered antibody, blocking its effectiveness and drastically reducing the time of subsequent protection. In addition, readministration of the same antibody may become problematic, due to the potential induction of a hypersensitivity response. These problems can be overcome by production or immune immunoglobulin in human donors immunized with the vaccine. This approach is discussed in more detail in the Examples. Second, passively administered antibodies are cleared relatively rapidly from the circulation. The half life of a given antibody in vivo is between 2.5 and 23 days, depending on the isotype. Thus, when the antibodies are passively administered, rather than induced by immunization, only short term effectiveness can be achieved.

Another immunological approach to drug addiction has been to use a catalytic antibody which is capable of aiding hydrolysis of the cocaine molecule within the patient (Landry et al. (1993) *Science* 259:1899–1901). The catalytic antibody is generated by immunization of an experimental animal with a transition state analog of cocaine linked to a carrier protein; a monoclonal antibody is then selected that has the desired catalytic activity. Although this approach is attractive theoretically, it also suffers from some serious problems. Catalytic antibodies must be administered passively and thus suffer from all of the drawbacks of passive antibody therapy. Active immunization to generate a catalytic antibody is not feasible, because enzymatic activity is rare among antibodies raised against transition state analogs, and activity does not appear to be detectable in polyclonal preparations. In addition, the general esterase-like activity of such catalytic antibodies and the uncontrolled nature of the active immune response in genetically diverse individuals makes them potentially toxic molecules, particularly when they are being produced within a human patient.

Yugawa et al. (EP 0 613 899 A2) suggest the use of cocaine-protein conjugate containing a cocaine derivative for raising antibodies for the detection of cocaine or cocaine derivatives in a blood sample. The Syva patents (U.S. Pat. No. 3,888,866, U.S. Pat. No. 4,123,431 and U.S. Pat. No. 4,129,237) describe conjugates to raise cocaine antibodies for immunoassays. Disclosed are conjugates to BSA using diazonium salts derived from benzoyl ecgonine and cocaine. Conjugates are made using para-imino ester derivatives of cocaine and norcocaine to conjugate a carrier. Biosite (WO 93/12111) discloses conjugates of cocaine using the para-position of the phenyl ring of various cocaine derivatives increasing stability to hydrolysis by introducing an amide bond. The Strahilevitz patents (U.S. Pat. No. 4,620,977; U.S. Pat. No. 4,813,924; U.S. Pat. No. 4,834,973; and U.S. Pat. No. 5,037,645) disclose using protein conjugates of endogenous substances and drugs for treatment of diseases, preventing dependence on psychoactive haptens, as well as for use in immunoassays, immunodialysis and immunoadsorption.

However, no effective therapy for drug addiction, especially, cocaine addiction, has been developed. Thus, there is a need to develop a long term treatment approach to drug addiction, in particular cocaine addiction, which does not depend totally on the addicted individual for compliance and self-administration.

SUMMARY OF THE INVENTION

The present invention overcomes the above mentioned drawbacks and provides methods for treating drug abuse. Using therapeutic compositions, in particular hapten-carrier conjugates, the present invention elicits an immune response in the form of anti-drug antibodies within the addict which upon subsequent exposure to the drug in a vaccinated individual neutralizes the drug so the expected pharmacological effects are diminished, if not eliminated. The present invention provides a therapeutic for drug addiction, particularly cocaine addiction, based on vaccination of subjects with a drug/hapten-carrier conjugate, and more particularly, a cocaine-protein conjugate. Therapeutic compositions of the invention comprise at least one hapten and at least one T cell epitope-containing carrier which when conjugated to form a hapten-carrier conjugate is capable of stimulating the production of anti-hapten antibodies. The hapten can be a drug or drug derivative, particularly cocaine. When the therapeutic composition containing the drug/hapten carrier conjugate is administered to an addicted individual, anti-drug antibodies specific to the drug are elicited. A therapeutic immunization regimen elicits and maintains sufficiently high titers of anti-drug antibodies, such that upon each subsequent exposure to the drug during the period of protection provided by the therapeutic, anti-drug antibodies neutralize a sufficient amount of the drug in order to diminish, if not eliminate, the pharmacological effect of the drug. Also provided are novel methods of preparing these conjugates. A method of passive immunization is also provided, wherein a subject is treated with antibodies generated in a donor by vaccination with the hapten-carrier conjugate of the invention.

These and other features, aspects and advantages of the present invention will become more apparent and better understood with regard to the following drawings, description, and appended claims.

BRIEF DESCRIPTION OF THE DRAWINGS

FIG. 2a is a representation of a number of possible, arbitrarily labelled, "branches" of a hapten-carrier conjugate identified for ease of understanding suitable compounds and conjugates used in the practice of the instant invention.

FIG. 2b is a representation of a number of possible, arbitrarily labelled, "branches" of a hapten-carrier conjugate identified for ease of understanding suitable compounds and conjugates used in the practice of the instant invention, wherein Q' is a modified T-cell epitope-containing carrier, such as a modified protein carrier.

FIG. 3b is a representation of "branches" at the sites of variability off the tropane ring of cocaine of the cocaine conjugates and intermediates of the instant invention.

FIG. 4 is a representation of "branches" at the sites of variability off the tropane ring in FIG. 1b of four compounds useful in preparing the conjugates of the instant invention.

FIG. 6 is a representation of the structures of four alternative drugs of abuse suitable for conjugation and administration in accordance with the teachings of the instant invention.

FIG. 7 is a schematic diagram representing two possible conjugation reactions to prepare a single cocaine conjugate (PS-5) according to the methods of the instant invention.

FIG. 8 is a representation of the structures of "succinylated norcocaine" and "pre-activated succinylated norcocaine" useful in the preparation of some of the conjugates of the instant invention.

FIG. 12a is a gel showing the relative molecular weights of native (monomer and pentamer) and recombinant cholera toxin-B (CTB) (monomer).

FIG. 12b is a gel illustrating the stability of CTB pentamers over a pH range of 3–9.

FIG. 12c is a drawing of a Western Blot gel showing peak fractions rCTB#32 and rCTB#53 which were obtained by periplasmic expression resulting in pentameric CTB.

DETAILED DESCRIPTION OF THE INVENTION

Figure 1A:
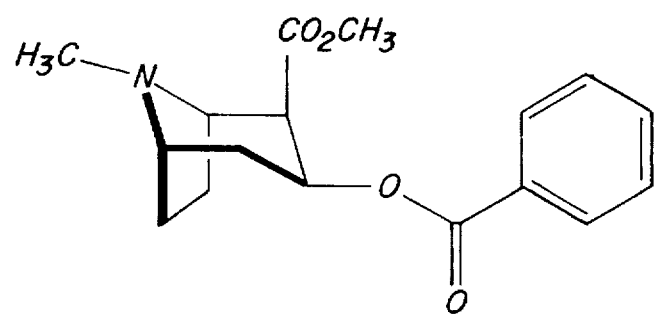
FIG. 1a is a schematic representation of the structural formula of cocaine.

The patent and scientific literature referred to herein establishes the knowledge that is available to those skilled in the art. The issued U.S. Patents, PCT publications, and other publications cited herein are hereby incorporated by reference.

The present invention provides a therapeutic for drug addiction, based on vaccination of an addicted individual with a drug-hapten-carrier conjugate, and more particularly, a cocaine-protein conjugate. Therapeutic compositions of the invention comprise at least one hapten and at least one T cell epitope containing carrier which when conjugated to form a hapten-carrier conjugate is capable of stimulating the production of anti-hapten antibodies. As used herein the term "T cell epitope" refers to the basic element or smallest unit of recognition by a T cell receptor, where the epitope comprises amino acids essential to receptor recognition. Amino acid sequences which mimic those of the T cell epitopes and which modify the allergic response to protein allergens are within the scope of this invention. A "peptidomemetic" can be defined as chemical structures derived from bioactive peptides which imitate natural molecules. The hapten can be a drug such as cocaine or drug derivative. When the therapeutic composition containing the hapten/drug (or derivative thereof) is administered to the addicted individual, anti-drug antibodies specific to the drug are elicited. A therapeutic immunization regimen elicits and maintains sufficiently high titers of anti-drug antibodies, such that upon subsequent exposure to the drug, neutralizing antibodies attach to a sufficient amount of the drug in order to diminish, if not eliminate the pharmacological effects of the drug. For example, when the therapeutic composition is a cocaine-carrier conjugate, treatment induces an anti-cocaine antibody response which is capable of reducing or neutralizing cocaine in the bloodstream or mucosal tissue of a subject, thereby blocking the psychologically addictive properties of the drug. Since in the present invention, delayed or reduced levels of the drug of abuse reach the central nervous system, the addict receives diminished or no gratification from the use of cocaine. No side effects are expected from the administration of the therapeutic of the instant invention. For example, the drug-of-abuse is small and monovalent and so is not able to cross-link antibody. Therefore, formation of immune complexes and the associated pathologies are not expected to occur after exposure to the drug of abuse. It is now, and is expected to be, compatible with current and future pharmacological therapies. Further, effective neutralization is long lasting. For example, neutralizing antibody responses against pathogens are known to last for years. Accordingly, it is expected that high-titer anti-drug antibodies elicited using the therapeutic composition of the instant invention can be maintained for long periods of time and possibly, at least a year. This long-term effect of the therapeutic composition with reduced compliance issues reduces recidivism which is a problem with current therapies.

Additionally, the therapeutic vaccination approach of the present invention to cocaine addiction is compatible with other therapies currently in use or in clinical trials. In fact, early phase co-therapy is highly desirable because of the time necessary to achieve optimal antibody titers. A number of diverse pharmacological agents would be suitable as co-therapies in preventing cocaine relapse, for example, desipramine, buprenorphine, naloxone, halperidol, chlorproazine, bromocriptine, ibogaine, as well as others that may become relevant.

The following are terms used herein, the definitions of which are provided for guidance. As used herein a "hapten" is a low-molecular-weight organic compound that reacts specifically with an antibody and which is incapable of inciting an immune response by itself but is immunogenic when complexed to a T cell epitope-containing carrier forming a hapten-carrier conjugate. Further, the hapten is characterized as the specificity-determining portion of the hapten-carrier conjugate, that is, it is capable of reacting with an antibody specific to the hapten in its free state. In a non-immunized addicted subject, there is an absence of formation of antibodies to the hapten. The therapeutic composition is used to vaccinate individuals who seek treatment for addiction to drugs. In the instant invention, the term hapten shall include the concept of a more specific drug/hapten which is a drug, an analog of a portion of the drug, or drug derivative. The therapeutic composition, or therapeutic anti-drug vaccine, when initially administered will give rise to a "desired measurable outcome". Initially, the desired measurable outcome is the production of a high titer of anti-drug antibodies (approximately 0.1 mg/ml to 1 mg/ml of specific antibody in the serum). However, manipulation of the dosage regimen suitable for the individual gives and maintains a sustained desired therapeutic effect. The "desired therapeutic effect" is the neutralization of a sufficient fraction of free drug of abuse to reduce or eliminate the pharmacological effects of the drug within a therapeutically acceptable time frame by anti-drug antibodies specific for the drug upon a subsequent exposure to the drug. Determining the therapeutically acceptable time frames for how long it takes to get a sufficient antibody response and how long that antibody response is maintained thereto and sufficient fraction of free drug are achieved by those skilled in the art by assessing the characteristics of the subject to be immunized, drug of abuse to be neutralized, as well as the mode of administration. Using this and other vaccination protocols as a model, one skilled in that art would expect the immunity or the period of protection to last several months, up to more than one year.

"Passive immunization" is also disclosed which encompasses administration of or exposure to intact anti-drug antibody or polyclonal antibody or monoclonal antibody fragment (such as Fab, Fv, (Fab')$_2$ or Fab') prepared using the novel conjugates of the instant invention. As stated above, passive immunization of humans with an anti-cocaine antibody of the present invention as a stand-alone treatment may be less useful than active immunization. Passive immunization would be particularly useful as an initial co-treatment and/or a supplementary complementary treatment (for example, during the period of time after initial administration of the vaccine but before the body's own production of antibodies) or in acute situations to prevent death (for example, when a person presents with a drug overdose). In some situations, passive therapy alone may be preferable, such as when the patient is immunocompromised or needs a rapid treatment.

The therapeutic composition of the instant invention, and more specifically, the therapeutic anti-drug vaccine, is a composition containing at least one drug/hapten-carrier conjugate capable of eliciting the production of a sufficiently high titer of antibodies specific to the drug/hapten such that upon subsequent challenge with the drug of the drug/hapten said antibodies are capable of reducing the addictive properties of the drug. The expected immune response to a hapten-carrier conjugate is the formation of both anti-hapten and anti-carrier antibodies. The therapeutic level is reached when a sufficient amount of the anti-drug specific antibodies are elicited and maintained to mount a neutralizing attack on drug introduced after vaccination. The therapeutic regimens of the instant invention allow for sufficient time for production of antibodies after initial vaccination and any boosting. Further, the optimal anti-drug vaccine contains at least one drug/hapten carrier conjugate comprising an optimal combination of the drug as hapten and a carrier so that production of anti-drug antibodies is capable of achieving an optimal therapeutic level, that is, remaining in vivo at a sufficiently high titer to withstand a subsequent challenge within several months with the selected drug. More particularly, the antibody titers remain sufficiently high to provide an effective response upon subsequent exposure to the drug for about two months to about one year or more depending upon the individual, more usually at least three months. This optimal composition consists of a hapten-carrier conjugate, excipients and, optionally adjuvants.

When used in the treatment of cocaine, the present invention defines a hapten-carrier conjugate, wherein the hapten is cocaine or a cocaine derivative, which can be used to immunize mammals, particularly humans, to elicit anti-cocaine antibodies capable of binding free drug and preventing transit of the drug to the reward system in the brain thereby abrogating addictive drug-taking behavior. It is believed that cocaine affects the neuronal uptake of dopamine, norepinephrine, and serotonin. While not intending to exclude other modes of action, it is believed that once cocaine enters the blood stream following inhalation (snorting or smoking) or intravenous administration, it rapidly crosses the blood-brain barrier where the intact cocaine binds to specific recognition sites located on the dopamine transporter of mesolimbocortical neurons, thereby inhibiting dopamine reuptake into presynaptic neurons. The euphoric rush is due to rapid build-up of dopamine in the synapse. The rapid action of cocaine presents problems unique to cocaine therapy. For this reason, cocaine remains the most complex and challenging, and before the present invention, elusive drug for which therapy is sought. Although estimates vary, it is believed that following intranasal administration, changes in mood and feeling states are perceived within about 2 to 5 minutes, and peak effects occur at 10 to 20 minutes. Thus, the active ingredient, the hapten-carrier conjugate, must be capable of eliciting fast-acting antibodies. Cocaine free-base, including the free-base prepared with sodium bicarbonate (crack), has a relatively high potency and rapid onset of action, approximately 8 to 10 seconds following smoking. An embodiment of the instant invention elicits antibodies capable of rapidly and specifically neutralizing cocaine within this time frame. Due to the route of the circulation, i.v. cocaine is intermediate in time of onset of euphoria taking from about 30 seconds to about 1 minute. Thus, when used in the treatment of cocaine abuse, the therapeutic hapten-carrier conjugate composition of the instant invention induce anti-cocaine antibodies which alter the physiological response to cocaine in humans. These antibodies possess the appropriate bioavailability and speed of binding that is required to neutralize cocaine in vivo. The Examples herein describe experiments done in mice to simulate alteration of response in mammals.

Initial vaccination with the therapeutic hapten-carrier conjugate composition of the present invention creates high titers of hapten-specific antibodies in vivo. Periodic tests of the vaccinated subjects plasma are useful to determine individual effective doses. Titer levels are increased and maintained through periodic boosting. It is anticipated that this therapeutic will be used in combination with current drug rehabilitation programs, including counseling. Further, the therapeutic compositions of the present invention may be aimed at a single drug or several drugs simultaneously or in succession and may be used in combination with other therapies. For example, the therapeutic hapten-carrier conjugate compositions and methods of the instant invention are used without adverse interactions in combination with conventional pharmacological approaches and previously discussed "short term" passive immunization and possible active immunization against transition states to enhance the overall effect of therapy.

The therapeutic hapten-carrier conjugate composition of the present invention is prepared by coupling one or more hapten molecules to a T cell epitope containing carrier to obtain a hapten-carrier conjugate capable of stimulating T cells (immunogenic) which leads to T cell proliferation and a characteristic release of mediators which activate relevant B cells and stimulate specific antibody production. Antibodies of interest are those specific to the hapten portion of the hapten-carrier conjugate (also called the hapten-carrier complex). Therapeutic compositions containing a combination of conjugates, either to the same drug (cross-immunization) or to multiple drugs (co-immunization) are disclosed. Such co-mixtures of conjugates of multiple drugs are particularly useful in the treatment of polydrug abuse.

In selecting drug suitable for conjugation according to the instant invention, one skilled in the art would select drug with properties likely to elicit high antibody titers. However, if the chosen molecule is similar to those molecules which are endogenous to the individual, antibodies raised against such a molecule could cross-react with many different molecules in the body giving an undesired effect. Thus, the drug to be selected as the hapten (drug/hapten) must be sufficiently foreign and of a sufficient size so as to avoid eliciting antibodies to molecules commonly found inside a human body. For these reasons, alcohol, for example, would not be suitable for the therapeutic of the instant invention. The antibodies raised against the therapeutic composition are highly specific and of a sufficient quantity to neutralize the drug either in the blood stream or in the mucosa or both. Without limiting the invention, the drugs which are suitable for therapeutic composition (not in order of importance) are:

Hallucinogens, for example mescaline and LSD;

Cannabinoids, for example THC;

Stimulants, for example amphetamines, cocaine, phenmetrazine, methylphenidate;

Nicotine;

Depressants, for example, nonbarbiturates (e.g. bromides, chloral hydrate etc.), methaqualone, barbiturates, diazepam, flurazepam, phencyclidine, and fluoxetine;

Opium and its derivatives, for example, heroin, methadone, morphine, meperidine, codeine, pentazocine, and propoxyphene; and "Designer drugs" such as "ecstasy".

FIG. 6 shows the structure of four drugs suitable for conjugation according to the instant invention.

The carrier of the instant invention is a molecule containing at least one T cell epitope which is capable of stimulating the T cells of the subject, which in turn help the B cells initiate and maintain sustained antibody production to portions of the entire conjugate, including the hapten portion. Thus, since a carrier is selected because it is immunogenic, a strong immune response to the vaccine in a diverse patient population is expected. The carrier, like the hapten, must be sufficiently foreign to elicit a strong immune response to the vaccine and to avoid the phenomenon of carrier-induced epitope suppression. A conservative, but not essential, approach is to use a carrier to which most patients have not been exposed. However, even if carrier-induced epitope suppression does occur, it is manageable as it has been overcome by dose changes (Dijohn et al. (1989) *Lancet* 1415–1418) and other protocol changes (Etlinger et al. (1990) *Science* 249:423–425), including the use of CTB (Stok et al. (1994) *Vaccine* 12:521–526). Still further, carriers containing a large number of lysines are particularly suitable for conjugation according to the methods of the instant invention. Suitable carrier molecules are numerous and include, but are not limited to:

Bacterial toxins or products, for example, cholera toxin B-(CTB), diphtheria toxin, tetanus toxoid, and pertussis toxin and filamentous hemagglutinin, shiga toxin, pseudomonas exotoxin;

Lectins, for example, ricin-B subunit, abrin and sweet pea lectin;

Sub virals, for example, retrovirus nucleoprotein (retro NP), rabies ribonucleoprotein (rabies RNP), plant viruses (e.g. TMV, cow pea and cauliflower mosaic viruses), vesicular stomatitis virus-nucleocapsid protein (VSV-N), poxvirus vectors and Semliki forest virus vectors;

Artificial vehicles, for example, multiantigenic peptides (MAP), microspheres;

Yeast virus-like particles (VLPs);

Malarial protein antigen;

and others such as proteins and peptides as well as any modifications, derivatives or analogs of the above.

To determine features of suitable carriers, initial experiments were performed using bovine serum albumin as a protein carrier. The protein has been ideal for animal experiments, as it is inexpensive and contains large numbers of lysines for conjugation. However, it is less appropriate for human vaccination because the generation of anti-BSA antibodies has the potential to cause adverse responses. Thus, using the results of these experiments, the above-described criteria were applied to a large number of candidate carriers. The result is the list of carriers described above suitable for the practice of the instant invention.

The carrier of a preferred embodiment is a protein or a branched peptide (e.g., multi-antigenic peptides (MAP)) or single chain peptide. An ideal carrier is a protein or peptide which is not commonly used in vaccination in the country in which the therapy is used, thereby avoiding the potential of "carrier induced epitopic suppression." For example, in the U.S., where standard childhood immunization includes diphtheria and tetanus, proteins such as tetanus toxoid and diphtheria toxoid, if unmodified, may be less desirable as appropriate carriers. Further, the carrier protein should not be a protein to which one is tolerant. In humans, this would exclude unmodified human serum albumin. Further, many food proteins would have to be carefully screened before use as a carrier. Again, in humans, bovine serum albumin would be less desirable as a carrier due to the beef in the diet of most humans. Still further, it is highly advantageous if the carrier has inherent immunogenicity/adjuvanticity. A delicate balance must be struck between the desire for immunogenicity of the carrier and the desire to maximize the anti-hapten antibody. Still further, the preferred carrier would be capable of both systemic response and response at the site of exposure. This is particularly true of cocaine which is more frequently administered across mucosal membranes. The speed of response is especially critical where cocaine has been smoked. Accordingly, in the case of cocaine, a preferred carrier elicits not only a systemic response but also a pre-existing mucosal antibody response. In such a mucosal response the reaction of antibodies with cocaine would happen rapidly enough to counteract the drug before it begins circulating in the blood stream.

One such ideal carrier is cholera toxin B (CTB) is a highly immunogenic protein subunit capable of stimulating strong systemic and mucosal antibody responses (Lycke (1992) *J. Immunol.* 150:4810–4821; Holmgren et al. (1994) *Am. J. Trop. Med. Hyg.* 50:42–54; Silbart et al. (1988) *J. Immun. Meth.* 109:103–112; Katz et al. (1993) *Infection Immun.* 61:1964–1971). This combined IgA and IgG anti-hapten response is highly desirable in blocking cocaine that is administered nasally or by inhalation. In addition, CTB has already been shown to be safe for human use in clinical trials for cholera vaccines (Holmgren et al., supra; Jertborn et al. (1994) *Vaccine* 12:1078–1082; "The Jordan Report, Accelerated Development of Vaccines" 1993., *NIAID*, 1993). Fourth, most cocaine addicts in the U.S. have not been exposed to cholera and therefore will not already be immune to CTB.

Other useful carriers include those with the ability to enhance a mucosal response, more particularly, LTB family of bacterial toxins, retrovirus nucleoprotein (retro NP), rabies ribonucleoprotein (rabies RNP), vesicular stomatitis virus-nucleocapsid protein (VSV-N), recombinant pox virus subunits, and multiantigenic peptides (MAP).

In yet another embodiment, various proteins derivatives, peptides fragments or analogs, of allergens are used are carriers. These carriers are chosen because they elicit a T cell response capable of providing help for B cell initiation of anti-hapten antibodies. Examples of and methods of making allergen proteins and peptides and their sequences are disclosed in WO 95/27786 published Oct. 19, 1995.

Using the methods and compositions of the present invention, and more particularly, the techniques set out in the Examples below, one skilled in the art links the selected drug/hapten with the selected carrier to make the hapten-carrier conjugate of the instant invention. An allergen which is particularly suitable as a carrier is *Cryptomeria japonica*, more particularly, recombinant Cry j 1, the sequence of which has been published with slight variation. In countries other than Japan, *Cryptomeria japonica* is not prevalent. Therefore, Cry j 1 allergen generally fits one of the criteria of a suitable carrier, that is a carrier to which a subject has not been previously exposed.

In one embodiment of the present invention, the antibodies induced by the therapeutic composition act within the time it takes for the drug to travel from the lungs through the heart to the brain. The ability to elicit this antibody response requires the careful selection of the carrier molecule.

Production of Recombinant B Subunit of Cholera Toxin

Cholera toxin is the enterotoxin produced by *Vibrio cholerae* and consists of five identical B subunits with each subunit having a molecular weight of 11.6 KDa (103 amino acids) and one A subunit of 27.2 KDa (230 amino acids) (Finkelstein (1988) *Immunochem. Mol. Gen. Anal. Bac. Path.* 85–102). The binding subunit, CTB, binds to ganglioside $G_{M1}$ on the cell surface (Sixma et al. (1991) *Nature* 351:371–375; Orlandi et al. (1993) *J. Biol. Chem.* 268:17038–17044). CTA is the enzymatic subunit which enters the cell and catalyzes ADP-ribosylation of a G protein, constitutively activating adenylate cyclase (Finkelstein (1988) *Immunochem. Mol. Gen. Anal. Bac. Path.* pp. 85–102). In the absence of the A subunit, cholera toxin is not toxic.

Others have disclosed the production of high level recombinant expression of CTB pentamers (L'hoir et al. (1990) *Gene* 89:47–52; Slos et al. (1994) *Protein Exp. Purif.* 5:518–526). While native CTB is commercially available, it is frequently contaminated with (approximately 0.1%) CTA. Therefore, recombinant CTB has been expressed in *E. coli* and developed assays for its characterization. The choleragenoid construct was purchased from the American Type Culture Collection (pursuant to U.S. Pat. No. 4,666,837). Recombinant CTB was cloned from the original vector (pRIT10810) into an expression plasmid (pET11d, Novagen) with an extra N-terminal sequence containing a $His_6$ tag and expressed in *E. coli* to the level of 25 mg/liter of culture. The protein was purified over a $Ni^{2+}$ column using standard techniques and analyzed on SDS-PAGE (see FIGS. 12a, b and c). The recombinant CTB is monomeric in this assay and is larger than the native CTB monomer due to the N-terminal extension.

Pentameric recombinant CTB was produced both with and without the His tag using the cDNA modified by PCR to include the Pel b leader sequence. A C-terminal Stop codon was inserted to remove the His tag. Both constructs were expressed in *E. coli* from the pET22b vector (Novagen). The His tagged protein was purified by $Ni^{2+}$ affinity chromatography as above (13 mg/L). The untagged recombinant CTB was purified by ganglioside $G_{M1}$ column affinity chromatography as described (Tayot et al. (1981) *Eur. J. Biochem.* 113:249–258). Recombinant CTB pentamer was shown to bind to ganglioside $G_{M1}$ in an ELISA and reacted with pentamer-specific antibodies in Western blots and ELISA. Recombinant CTB is also available from other sources.

Figure 13A:
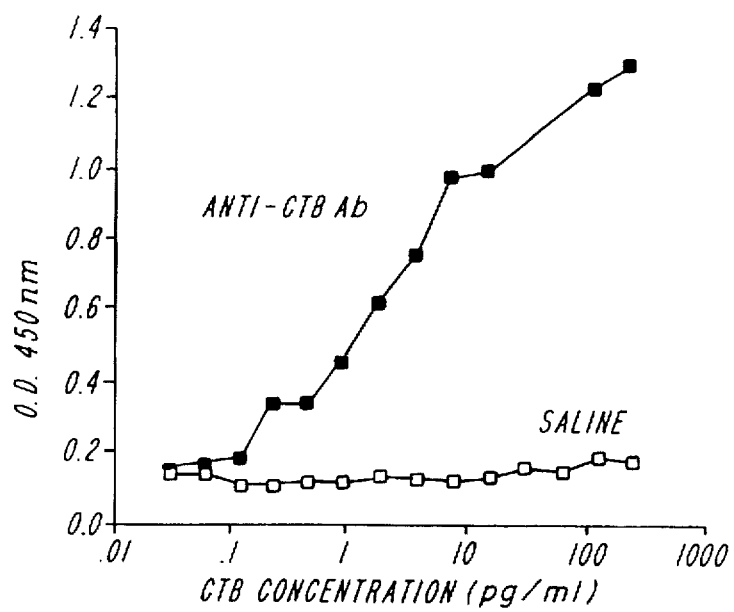
FIG. 13a is a graph representing an ELISA where the anti-CTB antibody detects the ability of rCTB to bind to ganglioside $G_{M1}$ on the ELISA plate.
Figure 13B:
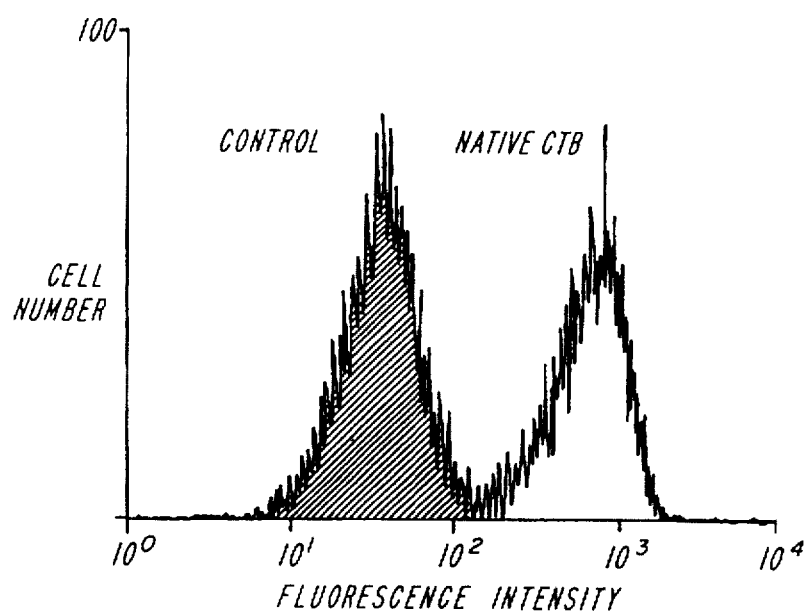
FIG. 13b is a scan depicting a flow cytometry binding assay in which rCTB is bound to eukaryotic cells expressing ganglioside $G_{M1}$.

The pentameric structure of CTB may be preferred for binding to ganglioside $G_{M1}$. The pentamer is stable to SDS as long as the samples are not boiled, permitting pentamerization to be assessed by SDS-PAGE. The gel in FIG. 12a demonstrates that the native CTB is a pentamer and is readily distinguishable from the denatured monomeric CTB. Pentamer structure is maintained over a pH range from 4 to 9 (see FIG. 12b), which facilitates a variety of conjugation chemistries. The recombinant CTB initially expressed is monomeric. One way to obtain pentameric CTB is by making adjustments to express properly folded pentameric CTB. It has been found that cytoplasmic expression provides a much higher levels of monomeric CTB. One skilled in the art is aware of methods of folding monomeric CTB into pentameric CTB (see, e.g., L'hoir et al. (1990) *Gene* 89:47–52). An alternative to re-folding monomeric CTB to obtain pentameric CTB is periplasmic expression which resulted in pentameric recombinant CTB able to bind $G_{M1}$-ganglioside by ELISA, FIG. 13a and FIG. 13b show the data supporting this finding. One skilled in the art may find several approaches for obtaining pentameric recombinant CTB have been described, including periplasmic expression with a leader (Slos et al., supra; Sandez et al. (1989) *Proc. Nat'l. Acad. Sci.* 86:481–485; Lebens et al. (1993) *BioTechnol.* 11:1574–1578) or post-translational refolding (L'hoir et al., supra; Jobling et al. (1991) *Mol. Microbiol.* 5:1755–1767).

Another useful carrier is cholera toxin which provides improved mucosal response over CTB. It has been reported that the enzymatically active A subunit adjuvant enhances activity (Liang et al. (1988) *J. Immunol.* 141:1495–1501; Wilson et al. (1993) *Vaccine* 11:113–118; Snider et al. (1994) *J. Immunol.* 153:647).

Figure 10A:
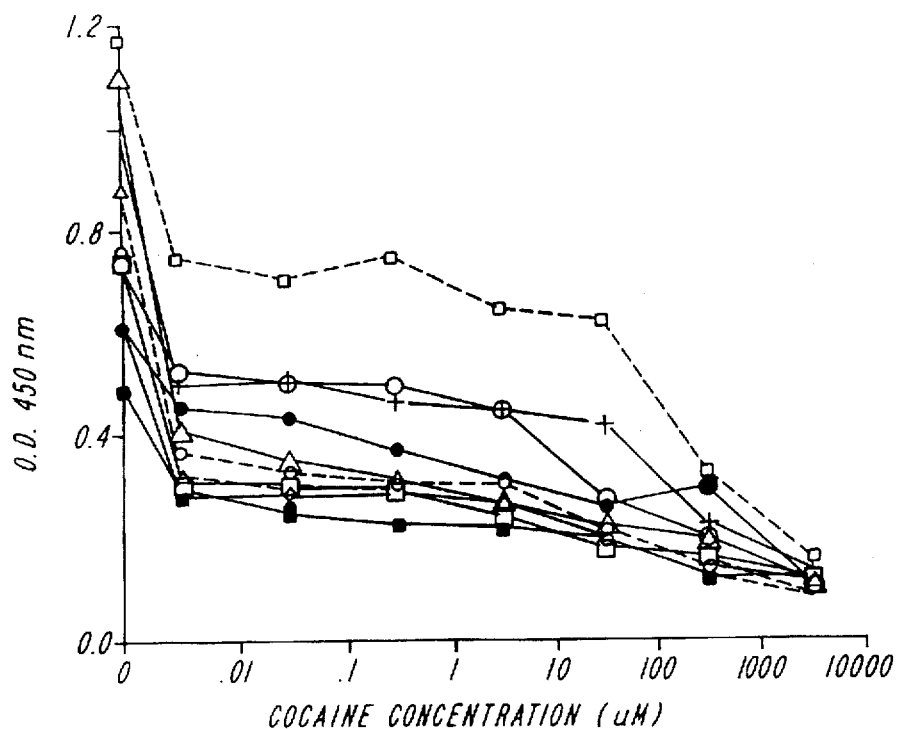
FIG. 10a is a graph demonstrating that antiserum binding to a cocaine-protein conjugate can be competed off using free cocaine.

One aspect of achieving the conjugate of the instant invention involves modifying the hapten, sufficiently to render it capable of being conjugated or joined to a carrier while maintaining enough of the structure so that it is recognized as free state hapten (for example, as free cocaine). It is essential that a vaccinated individual has antibodies which recognize free (hapten cocaine). Radioimmunoassay and competition ELISA assay (FIGS. 10a and 10b) experiments, explained in more detail in the Examples, can measure antibody titers to free hapten. Antibodies of interest are hapten-specific antibodies and, in some embodiments, are cocaine-specific antibodies. It should be recognized that principles and methods used to describe the preferred embodiments may be extended from this disclosure to a wide range of hapten-carrier conjugates useful in the treatment of a variety of drug addictions and toxic responses.

Conjugates

Preparation of the novel cocaine-carrier conjugates of the instant invention are derived from cocaine and cocaine metabolites, primarily derivatives of norcocaine, benzoyl ecgonine and ecgonine methyl ester. FIG. 4 shows a representation of the cocaine molecule as compared to these molecules. In the case of norcocaine and ecgonine methyl ester, the secondary amine and the secondary alcohol functional groups present in the two compounds respectively, are modified to provide a chemical linkage which enables attachment to a protein carrier. In the case of benzoyl ecgonine, the free acid is either used directly to attach to a carrier protein or is modified with a linkage to facilitate the same. The length and nature of the linkage is such that the hapten is displaced a sufficient distance from the carrier domain to allow its optimal recognition by the antibodies initially raised against it. The length of the linker is optimized by varying the number of —$CH_2$— groups which are strategically placed within a "branch" selected from the group consisting of:

| | |
|---|---|
| CJ 0 | Q |
| CJ 1 | $(CH_2)_nQ$ |
| CJ 1.1 | $CO_2Q$ |
| CJ 1.2 | COQ |
| CJ 2 | $OCO(CH_2)_nQ$ |
| CJ 2.1 | OCOCH=Q |
| CJ 2.2 | $OCOCH(O)CH_2$ |
| CJ 2.3 | $OCO(CH_2)_nCH(O)CH_2$ |
| CJ 3 | $CO(CH_2)_nCOQ$ |
| CJ 3.1 | $CO(CH_2)_nCNQ$ |
| CJ 4 | $OCO(CH_2)_nCOQ$ |
| CJ 4.1 | $OCO(CH_2)_nCNQ$ |
| CJ 5 | $CH_2OCO(CH_2)_nCOQ$ |
| CJ 5.1 | $CH_2OCO(CH_2)_nCNQ$ |
| CJ 6 | $CONH(CH_2)_nQ$ |
| CJ 7 | $Y(CH_2)_nQ$ |
| CJ 7.1 | $CH_2Y(CH_2)_nQ$ |
| CJ 8 | $OCOCH(OH)CH_2Q$ |
| CJ 8.1 | $OCO(CH_2)_nCH(OH)CH_2Q$ |
| CJ 9 | $OCOC_6H_5$ |
| CJ 10 | shown on FIG. 2b | and shown in FIGS. 2a and 2b herein. With regard to the above branches, n is an integer preferably selected from about 3 to about 20, more particularly about 3 to about 6; Y is preferably selected from the group consisting of S, O, and NH; and Q is preferably selected from the group consisting of:

(1) —H (2) —OH (3) —$CH_2$ (4) —$CH_3$ (4a) —$OCH_3$ (5) —COOH (6) halogen (7) protein or peptide carrier (8) modified protein or peptide carrier (9) activated esters, such as 2-nitro-4-sulfophenyl ester and N-oxysuccinimidyl ester

(10) groups reactive towards carriers or modified carriers such as mixed anhydrides, acyl halides, acyl azides, alkyl halides, N-maleimides, imino esters, isocyanate, isothiocyanate; or

(11) another "branch" identified by its "CJ" reference number.

A T cell epitope containing carrier, e.g., a protein or peptide carrier may be modified by methods known to those skilled in the art to facilitate conjugation to the hapten, e.g., by thiolation. For example with 2-iminothiolane (Traut's reagent) or by succinylation, etc. For simplicity, $(CH_2)_nQ$, where Q=H, may be referred to as $(CH_3)$, methyl or Me, however, it is understood that it fits into the motif as identified in the "branches" as shown in FIGS. 2a and b.

Further abbreviations of commercially obtainable compounds used herein include:

BSA=Bovine serum albumin

DCC=Dicyclohexylcarbodiimide

DMF=N,N'-Dimethylformamide

EDC (or EDAC)=N-Ethyl-N'-(3-(dimethylamino)propyl) carbodiimide hydrochloride

EDTA=Ethylenediamine tetraacetic acid, disodium salt

HATU=O-(7-Azabenzotriazol-1-yl)-1,1,3,3-tetramethyluronium hexafluorophosphate

NMM=N-Methylmorpholine

HBTU=2-(1H-Benzotriazole-1-yl)-1,1,3,3-tetramethyluronium hexafluorophosphate

TNTU=2-(5-Norbornene-2,3-dicarboximido)-1,1,3,3-tetramethyluronium tetrafluoroborate PyBroP®=Bromo-tris-pyrrolidino-phosphonium hexafluorophosphate HOBt=N-Hydroxybenzotriazole Further the IUPAC nomenclature for several named compounds are:

Norcocaine

3β-(Benzoyloxy)-8-azabicyclo[3.2.1]octane-2β-carboxylic acid methyl ester

Benzoyl ecgonine

3β-(Benzoyloxy)-8-methyl-8-azabicyclo[3.2.1]octane-2β-carboxylic acid

Cocaine

3β-(Benzoyloxy)-8-methyl-8-azabicyclo[3.2.1]octane-2β-carboxylic acid methyl ester Ecgonine methyl ester 3β-(Hydroxy)-8-methyl-8-azabicyclo[3.2.1]octane-2β-carboxylic acid methyl ester Reactions In one embodiment, precursors of the conjugates of the instant invention are synthesized by acylating ecgonine methyl ester with bromoacetyl bromide in DMF in the presence of two equivalents of diisopropylethylamine. The product is then coupled to the thiol group of a thiolated carrier protein to obtain a conjugate with the general structure of PS-2 (see FIG. 3a and Example 1).

In another embodiment, precursors of the conjugates of the instant invention are synthesized by succinylating ecgonine methyl ester with succinic anhydride in DMF in the presence of one equivalent of triethylamine. The product is then coupled to the ε amino group of a lysine residue of a carrier protein to obtain a conjugate with the general structure of PS-4 (see FIG. 3a and Example 2).

In yet another embodiment, precursors of the conjugates of the instant invention are synthesized by reacting norcocaine with succinic anhydride in DMF in the presence of two equivalents of triethylamine. The product is then coupled to the ε amino group of a lysine residue of a carrier protein using EDC to obtain a conjugate with the general structure of PS-5 (see FIG. 3a and Method A of Example 3).

Conjugates with the general structure of PS-5 may be obtained in an alternative set of reactions. In this alternative, the protein conjugation can be carried out using a pre-activated succinylated norcocaine derivative. That is, the intermediate can be isolated and characterized. The pre-activated succinylated norcocaine derivative is synthesized by reacting 4-hydroxy-3-nitrobenzene sulfonic acid sodium salt with succinylated norcocaine in the presence of dicyclohexylcarbodiimide (DCC) and DMF. The product is conjugated to the amino group of a lysine residue of a carrier protein to obtain a conjugate with the general structure of PS-5 (See FIG. 3a and Example 7, Method B).

In still another embodiment, compounds of the instant invention are synthesized by reacting succinylated norcocaine with N-hydroxysuccimide in the presence of ethyl chloroformate, N-methylmorpholine (NMM) and DMF. The product is then coupled to the amino group of a lysine residue of a carrier protein to obtain a conjugate with the general structure of PS-5 (see FIG. 3a and Example 7, Method C).

In another embodiment, compounds of the instant invention are synthesized by reacting thionyl chloride with succinylated norcocaine. The product is then conjugated to a carrier protein to obtain a conjugate with the general structure of PS-5 (see FIG. 3a and Example 7, Method A).

In another embodiment, compounds of the instant invention are synthesized by reacting succinylated norcocaine with HATU in DMF and diisopropylethylamine (Carpino (1993) *J. Am. Chem. Soc.* 115:4397–4398). The product was added to an aqueous solution containing the carrier protein to obtain a conjugate with the general structure PS-5 (see FIG. 3a and Method A of Example 7).

In another embodiment, compounds of the instant invention are synthesized by reacting succinylated norcocaine with HBTU in DMF and diisopropylethylamine. The product was added to an aqueous solution containing the carrier protein to obtain a conjugate with the general structure PS-5 (see FIG. 3a and Method B of Example 7).

In yet another embodiment, compounds of the instant invention are synthesized by reacting succinylated norcocaine with TNTU in DMF and diisopropylethylamine. The product was added to an aqueous solution containing the carrier protein to obtain a conjugate with the general structure PS-5 (see FIG. 3a and Method C and D of Example 7).

In still another embodiment, compounds of the instant invention are synthesized by reacting succinylated norcocaine with PyBroP in DMF and diisopropylethylamine. The product was added to an aqueous solution containing the carrier protein to obtain a conjugate with the general structure PS-5 (see FIG. 3a and Method E and F of Example 7).

Alternatively, compounds of the instant invention are synthesized by succinylating the carrier protein with succinic anhydride in borate buffer. The product is then coupled to norcocaine in the presence of EDC to obtain a conjugate with the general structure of PS-5 (see FIG. 3a and Method B of Example 3).

In another embodiment, compounds of the instant invention are synthesized by reducing the free acid in benzoyl ecgonine to its corresponding primary alcohol, using borane-dimethylsulfide complex. The alcohol is reacted with succinic anhydride in DMF, the product of which is then conjugated to the free amino acid group of a carrier protein in the presence of EDC to obtain a conjugate with the general structure of PS-6 (see FIG. 3a and Example 4).

Figure 3A:
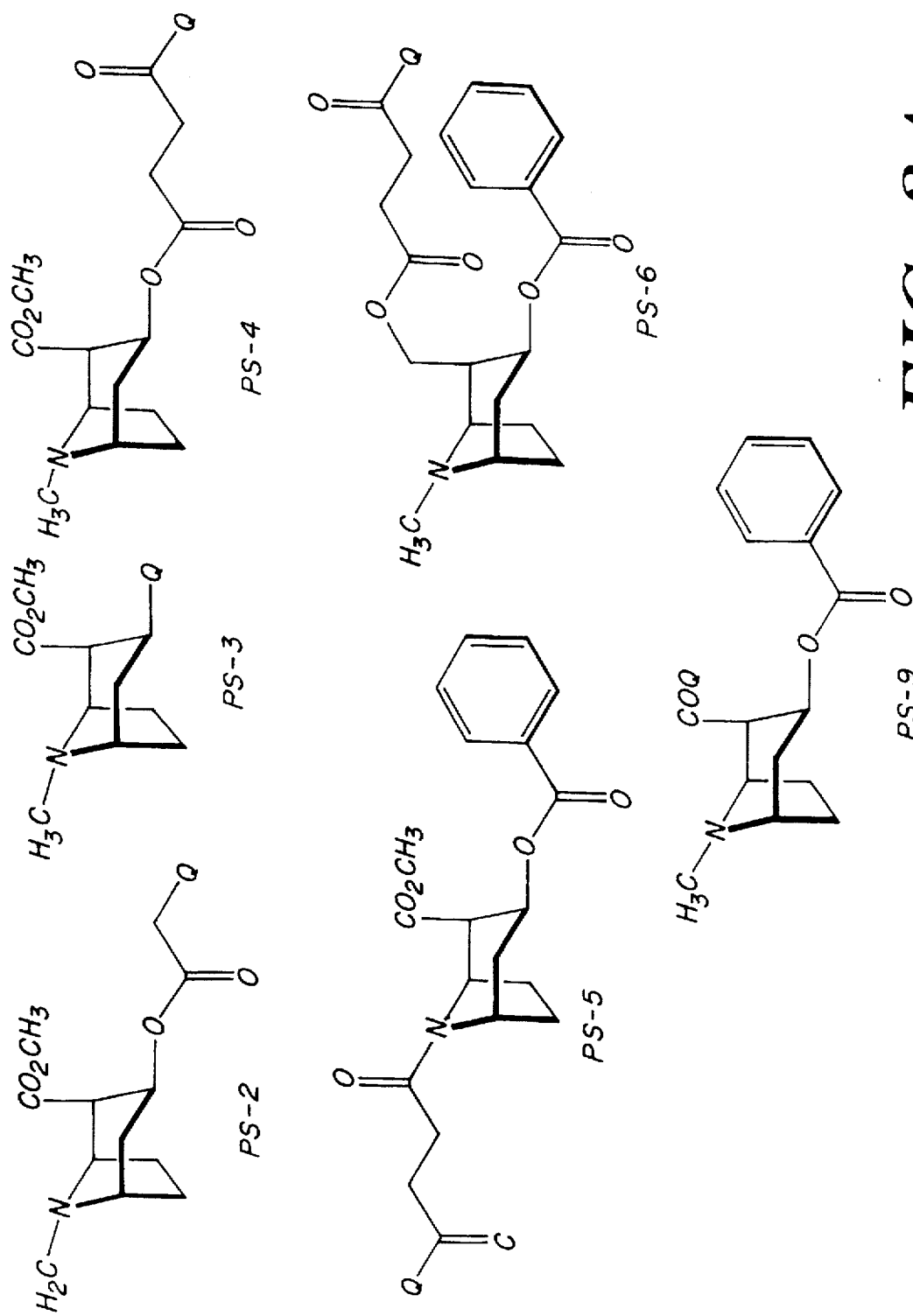
FIG. 3a is a representation of 6 cocaine conjugates (PS-2, PS-3, PS-4, PS-5, PS-6, and PS-9) of the instant invention, where Q is a T cell epitope-containing carrier such as a carrier protein or modified T cell epitope-containing carrier such as a modified carrier protein.
Figure 5:
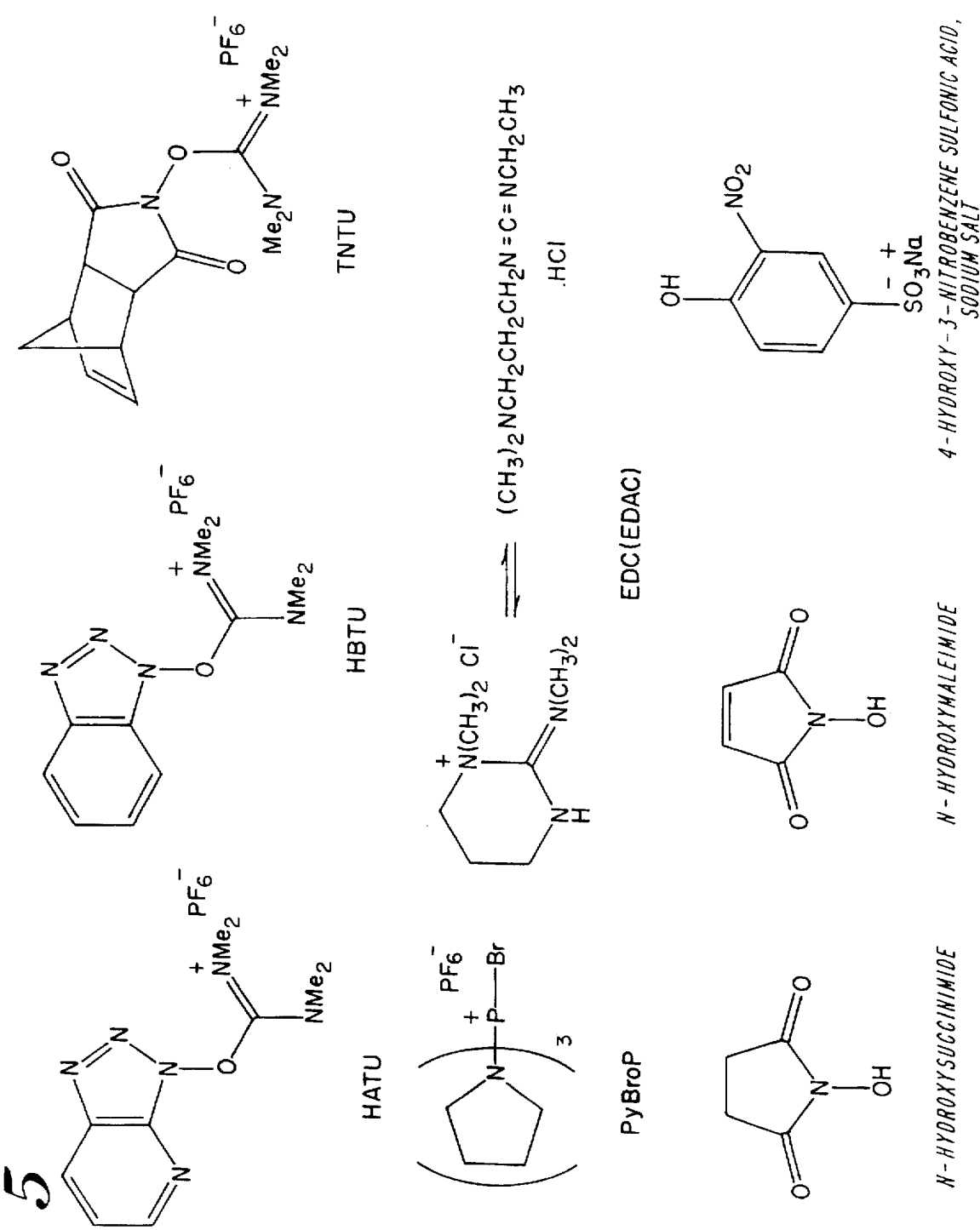
FIG. 5 is a representation of the structures of five reagents useful in the practice of the instant invention.

In another embodiment, compounds of the instant invention are synthesized by conjugating benzoyl ecgonine to the amino group of a lysine residue of a carrier protein in the presence of EDC to obtain a conjugate with the general structure of PS-9 (see FIG. 3a and Example 5).

The PS-5 analogs of CTB are synthesized using the protocols described in Example 5. The various methods described in Example 5 for synthesizing PS-5 analogs of CTB yield PS-5 analogs with different degrees of haptenation. The degree of haptenation can be determined by UV absorption or time of flight (TOF) mass spectral analysis. Table 2 shows that haptenation was achieved using several conjugates (some with CTB as a carrier) made pursuant to the methods of the instant invention. Different batches are indicated by adding a decimal and a number thereafter, e.g., PS-5 batch 6 is PS-5.6. The hapten-carrier conjugates of the invention can be haptenated to different degrees by using the methods described in Example 5 as well as various methods of conjugation known to those skilled in the art, e.g., different choices of activating agents, different buffers, different reaction times, etc. The amount of haptenation of the conjugate is limited, however, by the number of nucleophilic groups contained within the carrier.

TABLE 2

| Conjugate | Carrier Protein | Haptens/Monomer | Conjugation Method |
|---|---|---|---|
| PS-2.2 | BSA | 16 | Ex 1 |
| PS-4.3 | BSA | 24 | Ex 4 |
| PS-5.1 | BSA | 4–20 | Ex 3, Method A |
| PS-5.4 | BSA | 29 | Ex 3, Method A |
| PS-5.6 | BSA | 20 | Ex 3, Method A |
| PS-5.7 | BSA | 27 | Ex 3, Method B |
| PS-6.1 | BSA | 9 | Ex 4 |
| PS-9 | BSA | 1–2 | Ex 5 |
| PS-9.2 | BSA | 7 | Ex 5 |
| PS-5.6 | CTB | 1.25 | Ex 6, Method A |
| PS-5.7 | CTB | <1 | Ex 7, Method A |
| PS-5.8 | CTB | 1.9 | Ex 6, Method A |
| PS-5.9 | CTB | 0.9–6.5 | Ex 7, Method B |
| PS-5.10 | CTB | 0.5–2.5 | Ex 7, Method C |
| PS-11 | CTB | 1.0–7.8 | Ex 6, Method A |
| PS-5.53 | CTB | 3.4 | Ex 6, Method A |
| PS-5.70 | CTB | NA† | Ex 6, Method B |

†NA - not available

This is a non-limiting list of conjugates. Other conjugates have been made with greater than one hapten coupled to the T cell epitope-containing carrier. Preferably, 1 to 100 haptens are coupled to the T cell epitope-containing carrier. Most preferably, 1 to 70 haptens are coupled to the T cell epitope-containing carrier.

Methods of synthesizing compounds PS-2, PS-3, PS-4, PS-5 and PS-6 are disclosed in the Examples. Following the methods disclosed, e.g., using activating agents under aqueous conditions, one skilled in the art can synthesize compounds PS-10 to PS-26 (see FIG. 3b (1) and (2)).

Hydrolysis of the methyl ester in the PS-2, PS-4, and PS-5 conjugates leads to the production of benzoyl ecgonine-specific antibodies, thus rendering the conjugate essentially ineffective as a therapeutic vaccine. For optimal conjugation and to prevent extensive hydrolysis of the methyl ester in the succinylated norcocaine and PS-5 conjugates, the buffer pH during conjugation is maintained between pH 7.6 and 7.8, with reaction times limited to 1.5 hours. In addition, post-conjugation purification of the PS-5 conjugate is ideally carried out at pH 6.5 using 20 mM sodium succinate buffer.

Figure 16:
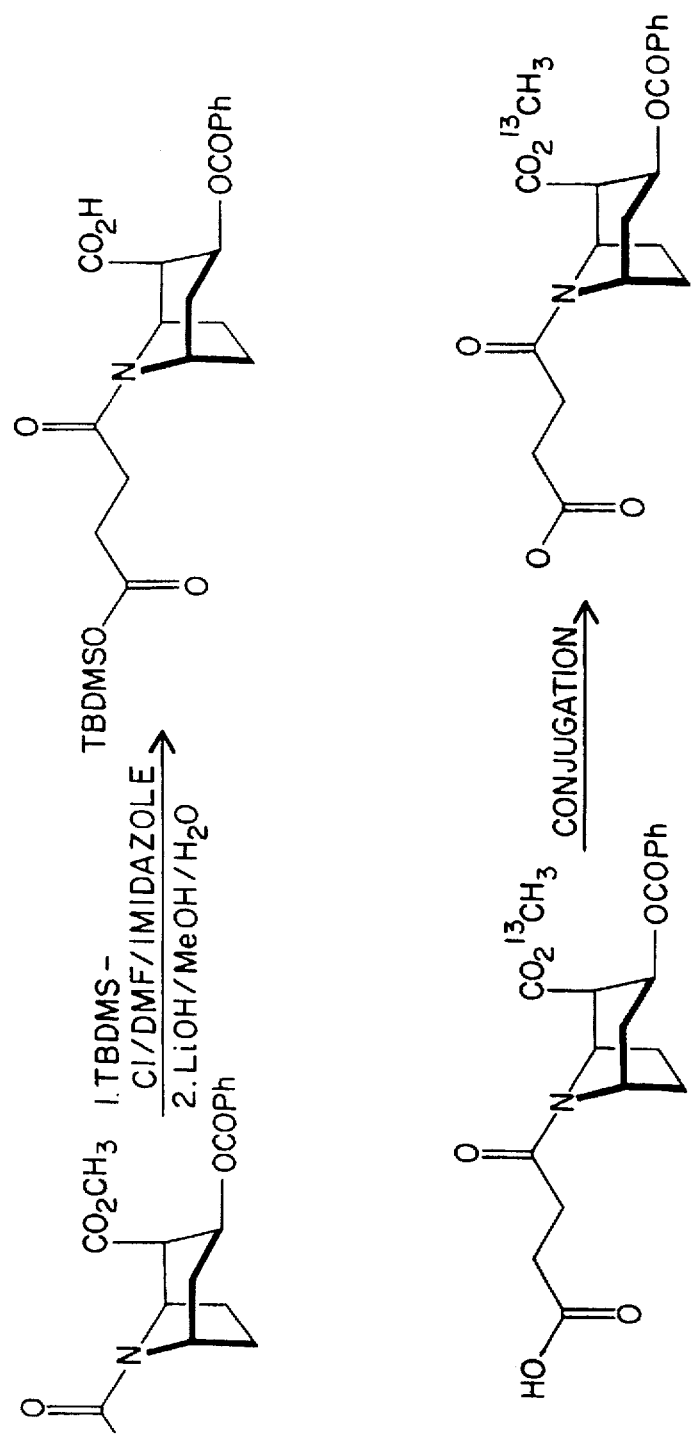
FIG. 16 is a schematic representation of the synthesis of a carbon-13 labelled conjugate.

In order to monitor the stability of the methyl ester, both immunological and physiochemical techniques can be employed. A cocaine-specific monoclonal antibody has been generated which can discriminate between cocaine and its metabolites when attached to the protein carrier. The reactivity to inactive metabolites was 2000 times less than to cocaine. Benzoylecgonine-specific monoclonal antibodies can be generated in-house using similar technology. Either monoclonal antibody or preferably both can be used to measure levels of intact and hydrolyzed conjugates compared to standard mixtures. This differentiation depends on the relative reactivity of each monoclonal antibody to the hydrolyzed and intact conjugate. In another embodiment a carbon-13 enriched containing methyl ester analog of succinylated norcocaine can be synthesized (FIG. 16). When conjugated to a carrier protein to form PS-5, carbon-13 nuclear magnetic resonance spectroscopy ($^{13}$C NMR) can be used to monitor the presence of the methyl ester and since the methyl group is isotope enriched, the signal corresponding to the methyl ester will be distinguishable above the protein signals.

In another embodiment a radioactively labelled methyl ester containing conjugate can be synthesized. This could include either a carbon-14 or tritium containing methyl ester analog of succinylated norcocaine. When conjugated to a carrier protein to form PS-5, the loss of radioactivity from either analog over time can be monitored using techniques known to those familiar with the art. Monitoring the loss of radioactivity will then indicate the residual levels of intact methyl ester.

The benzoate ester group in the PS-5 conjugates is essentially stable under the conditions of conjugation and purification, and therefore requires no monitoring for retention of structural integrity. If, however, increased bioavailability is desirable then incorporation of an amide bond or some other metabolically stable group, known to those familiar with the art, can be incorporated into the conjugate. Similarly, the methyl ester in the PS-5 conjugates can be stabilized using the branch CJ6 where Q=H, i.e. an amide bond. This incorporation would increase both the in vitro and in vivo stability of the conjugates.

Figure 1B:
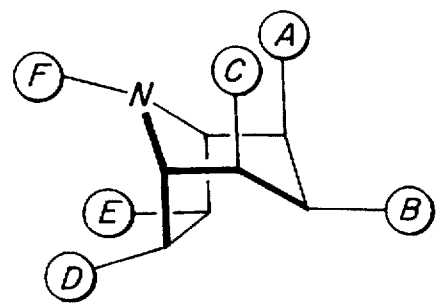
FIG. 1b is a diagram representing sites of variability when preparing a cocaine conjugate of the instant invention. The sites of variability are arbitrarily assigned to easily designate the compound and conjugates of the instant invention and not necessarily reaction sites.
Figure 15:
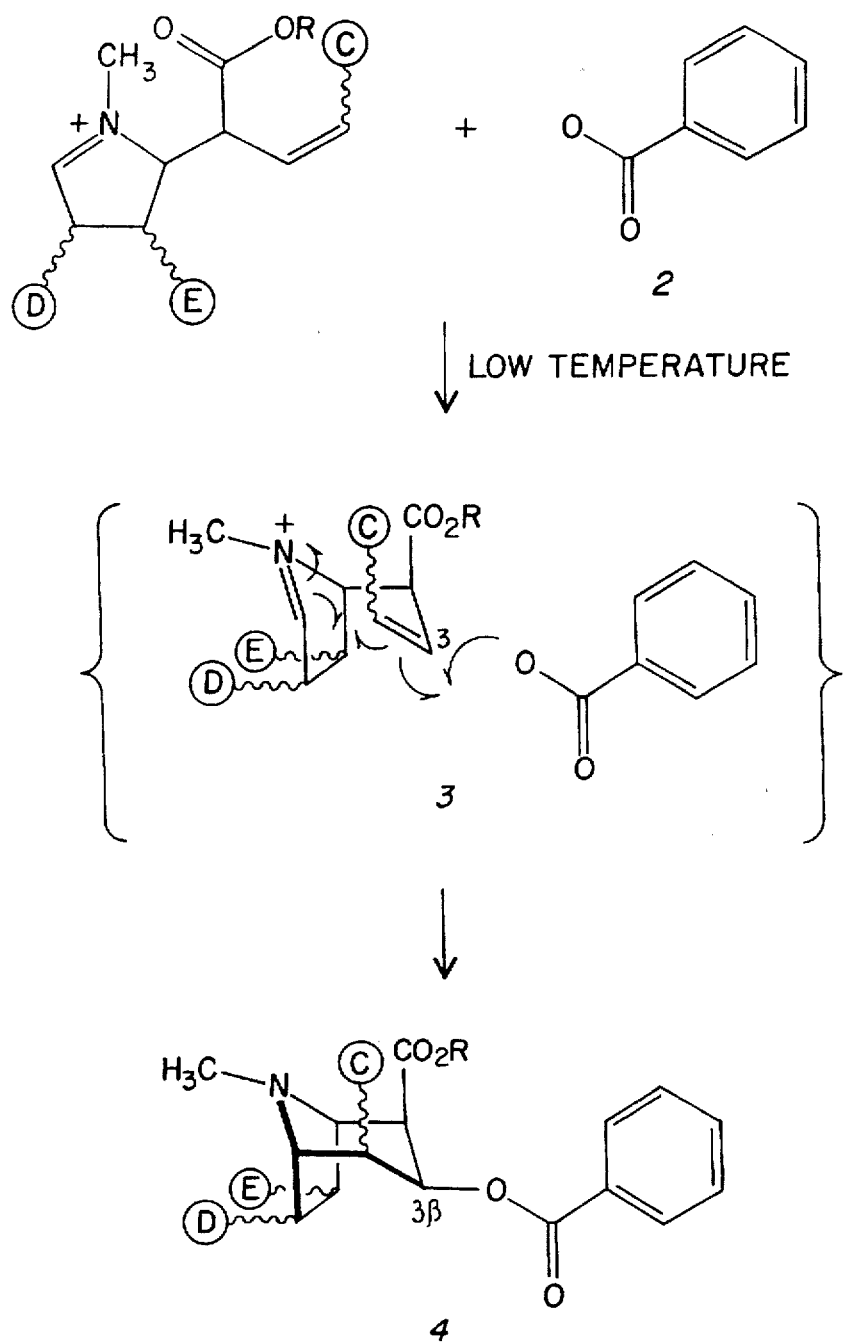
FIG. 15 is a schematic representation of another reaction useful in the preparation of conjugates of the instant invention, in particular, 3βbenzoate ester adduct 4.

In yet another embodiment, compounds PS-27 to PS-50 are synthesized via a series of reaction which allow a novel entry into the tropane class of alkaloids. This novel route involves a free radical mediated 1,6 diene-like intermolecular cyclization (March, *Advanced Organic Chemistry: Reactions, Mechanisms and Structure*, (1992) 4th ed., Wiley-Interscience, p. 744, and references cited therein). Tropane alkaloids, in particular cocaine and its analogs, have been previously synthesized; however these routes involve multiple steps and usually resolution of an intermediate (Wilstatter et al. (1923) *Ann. Chem.* 434:111–139; Tufariello et al. (1979) *J. Am. Chem.* 101:2435–2442; Lewin et al. (1987) *J. Heterocyclic Chem.* 24:19–21; and Simoni et al. (1993) *J. Med. Chem.* 36:3975–3977). Although limited to the synthesis of 3-aryltropane derivatives, Davies et al. (U.S. Pat. No. 5,262,428), synthesized cocaine analogs by decomposing vinyldiazothanes in the presence of pyrroles to form a tropane ring which is then followed by a Grignard addition to provide the cocaine analogs. In this alternative embodiment, novel cocaine-carrier conjugates with "remote site" branches are synthesized. As used herein "remote sites" are labelled C, D and E on FIG. 1. Those sites pose special challenges to the chemist due to the nature of the tropane ring and are especially difficult positions for "branches" necessary for conjugates of the instant invention. One embodiment, adds the "branches" then builds the tropane ring last. As represented in FIG. 15, there is a novel single step addition of the radical 2 and cyclization of, at low temperature, general compound 1. The stereochemical outcome is defined by the boat-like form of the intermediate 3 in which addition of the radical 2 occurs equatorially at position 3 followed by ring closure by the predicted mechanism, which gives the 3,β-benzoate ester adduct 4 (cocaine analog). The orientation of C, D, E and CO$_2$R would be predefined in 1.

There is a wide range of compounds which have been developed to facilitate cross-linking linking of proteins/peptides or conjugation of proteins to derivatized molecules, e.g., haptens. These include, but are not limited, to carboxylic acid derived active esters (activated compounds), mixed anhydrides, acyl halides, acyl azides, alkyl halides, N-maleimides, imino esters, isocyanates and isothiocyanates, which are known to those skilled in the art. These are capable of forming a covalent bond with a reactive group of a protein molecule. Depending upon the activating group, the reactive group is the ε amino group of a lysine residue on a protein molecule or a thiol group in a carrier protein or a modified carrier protein molecule which, when reacted, result in amide, amine, thioether, amidine urea or thiourea bond formation. One skilled in the art may identify further suitable activating groups, for example, in general reference texts such as *Chemistry of Protein Conjugation* and *Cross-Linking* (Wong (1991) CRC Press, Inc., Boca Raton, Fla.). Ideally, conjugation is via a lysine side chain amino group. Most reagents react preferentially with lysine. An especially suitable carrier is CTB as it has 9 lysine residues per monomer in its native form. To determine if conjugated CTB retains its structure and activity, $G_{M1}$ ganglioside binding can be assessed.

Applicants have expressed and purified amounts of recombinant CTB which, once optimized, are produced in large fermentation batches. Processes for expressing and purifying recombinant protein are know in the art, for example, U.S. Ser. No. 07/807,529. For example, CTB may be purified by affinity chromatography (Tayot et al. (1981) *Eur. J. Biochem.* 113:249–258), conjugated to cocaine derivatives, and the conjugate is then further purified. The purified CTB and the resulting conjugate are analyzed for purity and for maintenance of the pentameric structure of CTB. Techniques include SDS-PAGE, native PAGE, gel filtration chromatography, Western blotting, direct and $G_{M1}$-capture ELISA, and competition ELISA with biotinylated CTB. Level of haptenation is measured by mass spectrometry and by analysis of the increase in UV absorbance resulting from the presence of the hapten. Both the solubility and the stability of the conjugate are optimized in preparation for full-scale formulation. Details of some of these analyses are given in the Examples.

Several conjugates produced according to the present invention include conjugates with analogs of cocaine and either BSA, HEL or CTB as the protein carrier. Six representative cocaine analogs are shown in FIG. 3a. Of the six, PS-2, PS-4, PS-5, PS-6, and PS-9 were conjugated with BSA or HEL, while PS-5 was also conjugated with CTB. (See Table 2 above).

In order to vary levels of haptenation, alternative approaches are taken. In one embodiment the carrier is haptenated with a multivalent cocaine construct. This idea is based on the concept of multiple antigenic peptides (MAP) (Lu et al. *Mol. Immunol.*, 28:623–630 (1991)). In this system, multiple branched lysine residues are exploited to maximize hapten density and valency. The premise of this approach is that the immune response is enhanced if there are multiple copies of the hapten attached to the same peptide or protein molecule. Therefore, a multivalent hapten which needs to be attached to only one or two sites on the carrier CTB pentamer is prepared as set out herein. The core of such a multiple antigenic hapten is a branched polylysine core as suggested by Tam (Lu et al., supra). A chemically reactive handle is preserved by inclusion of a protected Cys residue. After cocaine haptenation of all available amino groups, the sulfhydryl of Cys is unmasked and made available for coupling to the protein with any of several bifunctional sulfhydryl/amino specific cross-linkers (Yoshitake et al. (1979) *Eur. J. Biochem.* 101:395–399. A number of dendrimeric structures are used as a core.

Adjuvant

Figure 9A:
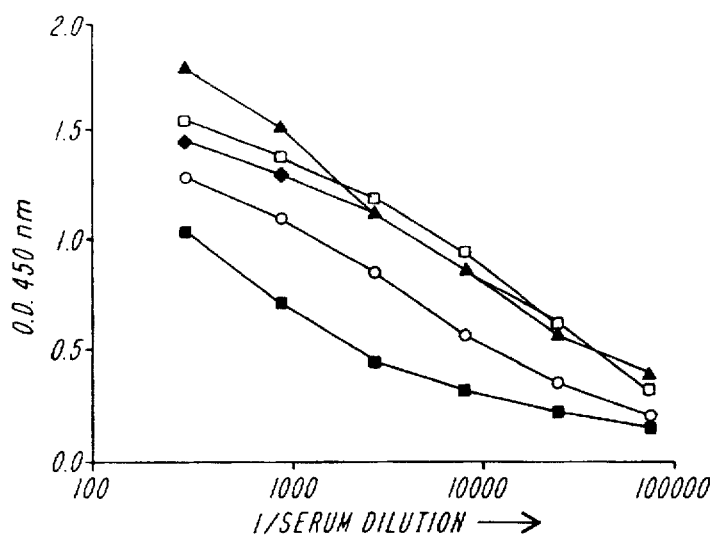
FIG. 9a is a graph showing the IgG antibody response in mice immunized with cocaine conjugate (PS-5.1/.6+CFA i.p.) of the instant invention. The antibody response is detected by in vitro binding to the appropriate HEL conjugate made using HEL rather than BSA as a carrier. Mice received 2 injections of 50 µg per injection. The curves represent the response of 5 individuals mice per group.

Any adjuvant which does not mask the effect of the carrier is considered useful in the cocaine therapeutic vaccine of the present invention (see, Edelman (1980) *Rev. Infect. Dis.* 2:370–373). Initial experiments aimed at demonstrating the feasibility of a therapeutic vaccine against cocaine addiction used the powerful adjuvant CFA (FIGS. 9a and c). However, CFA is not preferred in humans. A useful adjuvant currently licensed for use in humans is alum, including aluminum hydroxide (Spectrum Chem. Mtg. Corp., New Brunswick, N.J.) or aluminum phosphate (Spectrum). Typically, the vaccine is adsorbed onto the alum, which has very limited solubility. Preliminary data in the murine model suggests that alum is capable of inducing a strong anti-cocaine antibody response (FIG. 9b), and RIBI adjuvant is also suitable.

Effective immunization with CTB as the carrier protein does not require a powerful adjuvant. As shown in the Examples, high titer anti-cocaine antibody responses were induced by immunization with the CTB-cocaine conjugate either using alum as the adjuvant or in the absence of any added adjuvant.

Excipients and Auxiliary Agents

Therapeutic compositions may optionally contain one or more pharmaceutically acceptable excipients including, but not limited to, sterile water, salt solutions such as saline, sodium phosphate, sodium chloride, alcohol, gum arabic, vegetable oils, benzyl alcohols, polyethylene glycol, gelatine, mannitol, carbohydrates, magnesium stearate, viscous paraffin, fatty acid esters, hydroxy methyl cellulose, and buffer. Other suitable excipients may be used by those skilled in that art. The therapeutic composition may optionally comprising at least one auxiliary agent, for example, dispersion media, coatings, such as lipids and liposomes, surfactants such as wetting agents and emulsifiers, lubricants, preservatives such as antibacterial agents and anti fungal agents, stabilizers and other agents well known to those skilled in the art. The composition of the present invention may also contain further adjuvants, agents and/or inert pharmacologically acceptable excipients which may be added to enhance the therapeutic properties of the drug or enable alternative modes of administration.

Highly purified hapten-carrier conjugates produced as discussed above may be formulated into therapeutic compositions of the invention suitable for human therapy. If a therapeutic composition of the invention is to be administered by injection (i.e., subcutaneous injection), then it is preferable that the highly purified hapten-carrier conjugate be soluble in aqueous solution at a pharmaceutically acceptable pH (that is, a range of about 4–9) such that the composition is fluid and easy administration exists. The composition also optionally includes pharmaceutically acceptable excipients, adjuvant and auxiliary agents or supplementary active compounds. Depending upon the mode of administration, optional ingredients would ensure desirable properties of the therapeutic composition, for example, proper fluidity, prevention of action of undesirable microorganisms, enhanced bioavailability or prolonged absorption.

A therapeutic composition of the invention should be sterile, stable under conditions of manufacture, storage, distribution and use, and preserved against the contaminating action of microorganisms such as bacteria and fungi. A preferred means for manufacturing a therapeutic composition of the invention in order to maintain the integrity of the composition is to prepare the formulation of conjugate and pharmaceutically excipient such that the composition may be in the form of a lyophilized powder which is reconstituted in excipients or auxiliary agents, for example sterile water, just prior to use. In the case of sterile powders for the preparation of sterile injectable solutions, the preferred methods of preparation are vacuum drying, freeze-drying or spin drying which yields a powder of the active ingredient plus any additional desired ingredient from a previously sterile-filtered solution thereof.

The active compounds of this invention can be processed in accordance with conventional methods of galenic pharmacy to produce therapeutic compositions for administration to patients, e.g., mammals including humans. The preferred modes of administration are intranasal, intratracheal, oral, dermal, and/or injection. One particularly suitable combination of modes of administration comprises an initial injection with intranasal boosts.

For parenteral application, particularly suitable are injectable, sterile solutions, preferably oily or aqueous solutions, as well as suspensions, emulsions, or implants, including suppositories. Ampoules are convenient unit dosages. For enteral application, particularly suitable are tablets, dragees, liquids, drops, suppositories, or capsules. A syrup, elixir, or the like can be used wherein a sweetened vehicle is employed.

Sustained or directed release compositions can be formulated, e.g., liposomes or those wherein the active compound (conjugate) is protected with differentially degradable coatings, e.g., by microencapsulation, multiple coatings, etc. It is also possible to freeze-dry the new compounds and use the lyophilizates obtained, for example, for the preparation of products for injection.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments etc., which are, if desired, sterilized or mixed with auxiliary agent. For topical application suitable are sprayable aerosol preparations wherein the active compound, preferably in combination with a suitable excipient or auxiliary agent, is packaged in a squeeze bottle or in admixture with a pressurized volatile, normally gaseous propellant.

An antibody raised through the compositions and methods of the instant invention may have a molecular weight ranging from 150 KDa to 1,000 KDa. When the subject is exposed to free cocaine after vaccination with the optimized conjugate in the therapeutic composition, the free cocaine is targeted by cocaine-specific antibody or antibodies. No changes in the form or structure of the drug are necessary for the antibody to recognize the drug in vivo. While not intending to limit the present invention, it is believed that upon exposure of the vaccinated individual to cocaine, the anti-drug antibodies will block the effects of cocaine. At least three mechanisms are believed to contribute to the blocking activity. First, antibodies are unable to cross the blood-brain barrier. Therefore, it is believed that cocaine, when bound to the anti-cocaine antibody, will not cross the blood-brain barrier and will not be able to exert its effect on dopamine transporters. Second, the antibody prevents the drug from binding to its receptor by simple steric blockade. This mechanism is expected to be operative in blocking some of the non-CNS effects of cocaine (e.g. cardiac toxicity) and in the activity of antibodies against other drugs with non-CNS targets. Third, cocaine has a relatively short half-life in vivo due to both enzymatic and non-enzymatic hydrolysis, creating inactive metabolites. Cocaine, in particular, is a sufficiently small drug that is unable to cross-link antibodies, thus, no immune complex formation will occur.

Still further embodiments of mucosal applications are used in the practice of the present invention. For example, copolymer microspheres are used to induce or enhance a mucosal immune response. These small, biodegradable microspheres encapsulate and protect the conjugate and facilitate uptake by the mucosal immune system. Although they are most widely used for oral immunization, they also have been reported to be effective with intranasal immunization (Walker (1994) *Vaccine* 12:387–399). Inert polymers such as poly(lactide-co-glycolide) (PLG) of 1–10 µM diameter are particularly useful in this regard (Holmgren et al. (1994) *Am. J. Trop. Med. Hyg.* 50:42–54; Serva (1994) *Science* 265:1522–1524).

In addition to the preferred conjugates, cross-immunization with different conjugates is carried out in order to minimize antibody cross-reactivity. Mice are primed with conjugates, more particularly PS-5 or PS-9 conjugates, and then boosted at day 14 with the reciprocal PS-9 or PS-5 conjugates coupled to the same carrier, BSA. Only the subset of antibody-secreting B cells that recognize both of the cocaine conjugates are maximally stimulated and expanded. It is believed that because the two conjugates differ in their point of attachment to the cocaine molecule, the specificity of the recognition increases. Specificity of the induced antisera is then confirmed by competition ELISA.

Still further, therapeutic compositions containing more than one conjugate stimulate polyclonal antibodies thereby enhancing antibody response upon subsequent challenge.

Dose

Neutralizing antibody responses against pathogens are known to last for years, and it should be possible to achieve a high-titer anti-cocaine antibody response that is maintained for at least a year. Based on values obtained with conventional vaccines, it should be possible to achieve the concentrations of specific antibody required to neutralize cocaine plasma concentrations (1–10 µM); the pharmacokinetic data in mice, described in the Examples, clearly demonstrates that physiologically relevant neutralizing antibody concentrations can be achieved. Finally, the ability of maternal antibodies to cross the placenta in women addicted to cocaine, and thus protect the fetus, represents a further desirable effect of therapeutic cocaine vaccination. Optimizing therapy to be effective across a broad population is always challenging yet those skilled in the art use a careful understanding of various factors in determining the appropriate therapeutic dose. Further, antibody responses could be monitored using specific ELISAs as set out in the Examples and other antibody based assays.

Genetic variation in elimination rates, interactions with other drugs, disease-induced alterations in elimination and distribution, and other factors combine to yield a wide range of response to vaccine levels in patients given the same dose. Clinical indicators assist the titration of some drugs into the desired range, and no chemical determination is a substitute for careful observations of the response to treatment. Because clearance, half-life accumulation, and steady state plasma levels are difficult to predict, the measurement of anti-drug-of-abuse antibody production is useful as a guide to the optimal dose. Each of the conjugates/carriers/adjuvants of the present invention is evaluated for the ability to induce an antibody response that is best able to bind free cocaine in the circulation.

Further details about the effects of carriers and adjuvants on the induction of an antibody response are given in the Examples.

Thus, it will be appreciated that the actual preferred amounts of active compound in a specific case will vary according to the specific conjugate being utilized, the particular compositions formulated, the mode of application, and the particular situs and organism being treated. For example, in one embodiment, the therapeutic composition containing a suitable carrier, is given first parenterally and boosted mucosally. As is discussed in more detail herein, this type of immunization with the optimal hapten and carrier combination is very effective in generating primarily IgG systemically and primarily IgA locally.

As set out in the Examples murine models have been used to demonstrate and measure different characteristics of the antibody response, including antibody titer, ability to recognize free cocaine, cocaine binding capacity, affinity for cocaine, specificity of the antibody response, antibody isotype, antibody tissue localization, and the physiological effects of the antibody following cocaine administration.

Antibody Titer

The first screen for vaccination is whether the conjugate of interest induces a high titer antibody response. Antibody titers are determined using an ELISA assay as described in the Examples below. Plates are coated with a cocaine-HEL conjugate, washed extensively, and incubated with varying dilutions of the test serum. The plates are again washed and developed with an enzyme-labelled anti-mouse IgG second antibody. Titers are defined as the reciprocal of the dilution of serum that gives 50% of the maximal response.

Antibody titer depends on both the concentration of antibody and on the antibody affinity. As detailed in the Examples, antisera with about 0.7 mg/ml cocaine-specific antibody of median affinity of about $2\times10^{-8}$M (or $5\times10^7$M$^{-1}$) had an ELISA titer of 80,000. In estimating required antibody titer, both the concentration and the affinity of the antibodies are considered by those skilled in the art.

Although other methods of calculating appropriate antibody concentration are well known to those skilled in the art, without intending to limit the invention, one method of predicting anti-cocaine antibody concentration requirements is disclosed. Published peak plasma levels of cocaine in addicts are in the range of 0.3-1.5 µg/ml (Ambre et al. (1991) *J. Anal. Tox.* 15:17-20; Cone (1995) *J. Anal. Tox.* 19:159-478; and Cone et al. (1989) *J. Anal. Tox.* 13:65-68). Therefore, 0.075-0.375 mg/ml antibody is close to molar equivalence (The weight ratio of monoclonal antibody/cocaine=approximately 160,000/303=approximately 500 but there are two binding sites on each antibody, so the molar ratio for binding site to cocaine is about 250). It is possible to achieve this level of antibody response with haptenated carrier, as demonstrated in the Examples. However, if a drug-of-abuse-specific dimeric secreted-form IgA response is induced in the mucosa, as disclosed in at least one embodiment herein, the antibody concentration requirement is two-fold less relative to drug-of-abuse. It is not implied here that molar excess of antibody over drug-of-abuse is needed for successful therapy.

In one therapeutic composition of the instant invention, cocaine-specific antibody (monoclonal antibody) blocked the effects of a molar excess of cocaine in a rat addiction model. Rats were injected with 4 mg monoclonal antibody before infusion of cocaine (1 mg/kg; 300µg/rat). The measured concentration of monoclonal antibody in the rats was about 50µg/ml. The antibody was at less than molar equivalence to the cocaine when compared either in the whole animal or in the plasma.

Antibody affinity reflects the amount of antibody-drug complex at equilibrium with unbound antibody and unbound drug-of-abuse, thus:

$$K_{eq}=[Ab+drug\ complex]/[Ab]\times[drug]$$

where [Ab]=molar concentration of unoccupied antibody binding sites; [drug]=molar concentration of unbound drug [Ab+drug]=molar concentration of antibody-drug complex.

For example, based on calculations, antibodies with affinity for cocaine above $10^{-6}$ M are mostly bound to cocaine and antibodies with affinities of about $10^{-7}$M and are nearly all bound to cocaine at the expected antibody and cocaine plasma concentrations.

Ability to Recognize Free Cocaine

Once a conjugate is capable of inducing a high-titer serum antibody response, the serum also is tested for its ability to recognize free cocaine in a competition ELISA as described in the Examples. An ELISA assay is set up using a suboptimal dilution of serum. Varying concentrations of free cocaine are added along with the antiserum, and the ELISA is developed as above. Data is expressed as the concentration of free cocaine required to compete 50% of the antibody binding, an approximate measure of affinity. Lidocaine, among others, is used as a negative control in the competition experiments, and the cocaine-carrier conjugate that was used in the immunization is used as a positive control.

In addition to the competition ELISA assay binding is assessed using radiolabelled cocaine. The data resulting from such assays can indicate if the immune serum is binding to free cocaine. This is discussed in more detail in the Examples.

Specificity of Antibody Response

In order to be maximally effective at blocking the activity of cocaine, the induced antibodies must have minimal affinity for pharmacologically inactive metabolites of cocaine. Binding of antibodies to pharmacologically inactive metabolites of cocaine would reduce the potency of the vaccine. The primary inactive metabolites are ecgonine methyl ester, norcocaine and benzoylecgonine each of which is commercially available. The specificity of the antisera for each of these metabolites is determined in a competition ELISA and by radiolabelled immunoassay. This is discussed in more detail in the Examples, below.

Additionally, interaction of the antibodies raised with other drugs used in addiction therapy and in other medical procedures should be minimized. In particular, cross reaction with drugs commonly prescribed to cocaine and poly drug abusers is avoided. While the unique nature of the cocaine tropane ring structure minimizes cross-reactivities, they can be readily tested in a competition ELISA. Indeed, lidocaine is used as a negative control in our competition ELISA. The following molecules are useful as co-treatment, buprenorphine, desipramine, naloxone, haloperidol, chlorproazine, and bromocriptine, as well as others that may become relevant.

Effect on Cocaine $LD_{50}$

Those conjugates and immunization protocols that are most effective at inducing high titer specific antibody responses are further evaluated for their ability to shift the cocaine $LD_{50}$. In these experiments, cocaine-immunized and control carrier-immunized mice are injected i.v. with cocaine at doses around the previously defined $LD_{50}$. Ten mice are used at each point, and the data is analyzed using a Cochran-Mantel-Haenzel Chi-squared test.

In addition, a failure time model is used to analyze the time-to-death induced by cocaine. The extent to which the anti-cocaine antibodies increase both (a) the dose of cocaine required for lethality and (b) the time-to-death are measures of efficacy in this model. These provide a rapid and rigorous test of the in vivo efficacy of the antibodies.

Observing the Physiological Effect on Humans

A person who seeks medical attention during an episode of abuse might present with a rapid pulse, an increased respiratory rate and an elevated body temperature. At high levels of overdose, the picture progresses to grand mal convulsions, markedly elevated blood pressure, and a very high body temperature, all of which can lead to cardiovascular shock. In addition to blood levels, all these factors will be assessed and specific criteria will be established when administration of either active immunization with the vaccine or passive administration of antibodies to humans in contemplated.

Figure 11A:
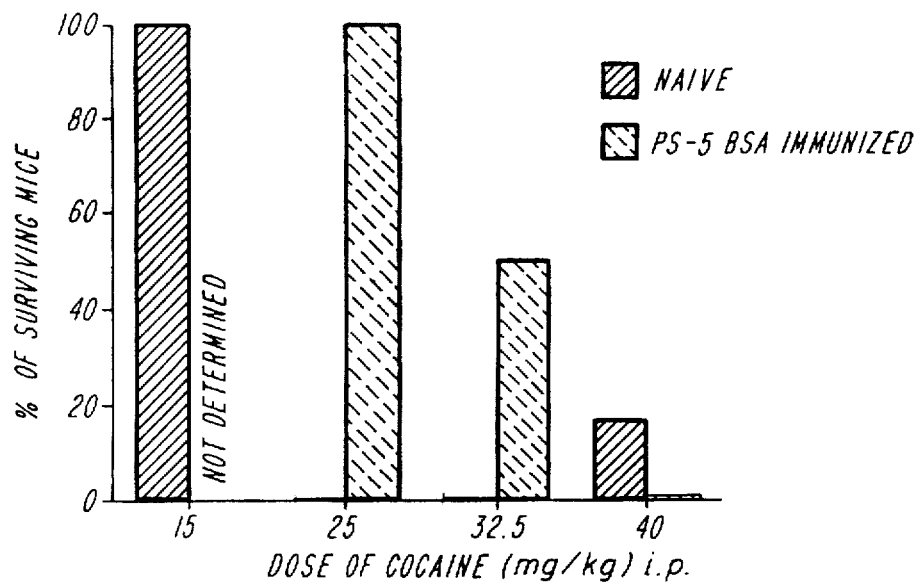
FIG. 11a is a bar graph illustrating that a cocaine-BSA conjugate prepared according to the method of the instant invention provide two-fold protection in high dose cocaine $LD_{50}$.

When embodiments of the invention were tested on mice, immunization with a protein-cocaine conjugate induced an antibody response that shifts the $LD_{50}$ for cocaine (FIGS. 11a & b). It is hypothesized that the relatively small shift that was observed at very high doses of cocaine translates into a more dramatic shift at lower cocaine concentrations; the dramatic effect of the anti-cocaine monoclonal antibody on cocaine self-administration is consistent with this hypothesis.

Without intending to limit the scope of the invention, the composition and methods of this invention will now be described in detail with reference to a preferred drug of abuse, cocaine, and specific embodiments.

Unless otherwise indicated in the Examples, female BALB/c mice of 2–3 months of age are used in these studies. These animals have a well defined reproducible response to the antigens under investigation. Animals are immunized either intramuscularly, subcutaneously, intratracheally, or intranasally with a protein-cocaine conjugate either in saline, or on alum, or in CFA. Unless otherwise noted, BALB/c mice are immunized s.c. with 50 μg of test conjugate. After 14 days, mice are boosted with the same dose. In mice immunized using CFA, IFA was used for the subsequent immunizations. Antibody responses in the serum are measured after an additional 14 days. Five mice are used per group and all sera are tested individually. CTB used in the following examples is commercially available, for example, from List or Sigma.

It is to be understood that the example and embodiments described herein are for purposes of illustration only, and that various modification in light thereof will be suggested to persons skilled in the art. Accordingly, the following non-limiting Examples are offered for guidance in the practice of the instant invention.

EXAMPLE 1

Synthesis of PS-2

A solution of ecgonine methyl ester hydrocholoride (50 mg, 0.21 mmol), diisopropylethylamine (80 μl, 0.46 mmol) in DMF (3 ml) was treated with bromoacetyl bromide (22 μl, 0.25 mmol) and heated at 40° C. overnight. The solvents were removed under reduced pressure and the residue purified by silica gel flash chromatography (9:1 chloroform:methanol as the eluent), furnishing the bromo compound (67 mg, 96%) as a pale yellow powder (3β-(Bromoacetyloxy)-8-methyl-8-azabicyclo[3.2.1]octane-2β-carboxylic acid methyl ester).

To a solution of the bromo compound (17 mg, 0.053 mmol) in PBS (0.5 ml), thiolated BSA (15 mg) in PBS (0.5 ml) was added and stirring continued at ambient temperature for 3 days. The conjugate was purified by dialysis against PBS and then analyzed by mass spectral analysis.

EXAMPLE 2

Synthesis of PS-4

To a solution of ecgonine methyl ester (32 mg, 0.16 mmol) in DMF (2 ml), triethylamine (22 μl, 0.16 mmol), followed by succinic anhydride (16 mg, 0.16 mmol) was added and the solution heated at 35° C. for 2 hours. The solvent was removed under reduced pressure and the residue purified by silica gel flash chromatography (9:1 chloroform:methanol as the eluent). This furnished the desired hemisuccinate (21 mg, 44%) as a white powder (3β-(Succinoyloxy)- 8-methyl-8-azabicyclo[3.2.1]octane-2β-carboxylic acid methyl ester).

To a solution of the hemisuccinate (2.4 mg, 7.69 μmol) in distilled water (0.5 ml) at 0° C., EDC (1.5 mg, 7.69 μmol) was added. After 10 minutes, BSA (2 mg in 0.5 ml PBS) and the solution allowed to warm to ambient temperature overnight. The conjugate was purified by dialysis against PBS and the degree of haptenation determined by mass spectral analysis.

EXAMPLE 3

Synthesis of PS-5

Method A

A solution of norcocaine hydrochloride (1 g, 3.07 mmol), triethylamine (0.86 ml, 6.14 mmol) in DMF (20 ml) was treated with succinic anhydride (614 mg, 6.14 mmol) and the mixture heated at 45° C. overnight. The solvents were removed under reduced pressure and the residue purified using silica gel flash chromatography (2:1 chloroform:methanol as the eluent). This gave succinylated norcocaine (1.0 g, 84%) as a thick syrup (3β-(Benzoyloxy)-8-succinoyl-8-azabicyclo[3.2.1]octane-2β-carboxylic acid methyl ester).

To a solution of the acid (14 mg, 0.036 mmol) in distilled water (1 ml) at 0° C., EDC (10.4 mg, 0.055 mmol) was added. After 5 minutes a solution of BSA (14 mg) in PBS (1 ml) was added dropwise and the mixture allowed to warm to ambient temperature overnight. The conjugate was purified by dialysis against PBS and the degree of conjugation analyzed by mass spectral analysis.

Method B

To a solution of BSA (500 mg) in 0.2M borate buffer (80 ml), succinic anhydride (270 mg, 2.70 mmol) in 1,4-dioxane (10 ml) was added in 200 μl aliquots over 30 minutes. The pH was maintained at 9.3 by addition of 3N sodium hydroxide solution. The solution was kept at ambient temperature for 18 hours, dialyzed against 0.01M triethylamine and then lyophilized to yield 583 mg of a fluffy white powder. Mass spectral analysis of the product indicated 55 succinoyl groups per BSA molecule.

A solution of succinylated BSA (72 mg) in 0.1M sodium bicarbonate buffer, pH 8.8 (15 ml) at 0° C. was treated with EDC (88 mg, 0.46 mmol). After 5 minutes, norcocaine hydrochloride (100 mg, 0.31 mmol) was added and the solution allowed to warm to ambient temperature overnight. The conjugate solution was purified by dialysis against PBS and the degree of haptenation determined by mass spectral analysis.

EXAMPLE 4

Synthesis of PS-6

To a solution of benzoyl ecgonine (276 mg, 0.96 mmol) in DMF (5 ml) at −10° C., borane-dimethylsulfide complex (1.0M solution in methylene chloride; 1.0 ml, 1.01 mmol) was added dropwise. This was allowed to warm to ambient temperature overnight, after which the reaction was quenched by the addition of THF: water (1:1 ratio v/v) followed by stirring for a further 10 minutes. The solvents were removed under reduced pressure and the residue purified using silicia gel flash chromatography (chloroform followed by methanol as eluents). This furnished the desired alcohol (246 mg, 93%) as a white powder (3β-(Benzoyloxy)-2β-(hydroxymethyl)-8-methyl-8-azabicyclo-[3.2.1]octane).

To a solution of the alcohol (190 mg, 0.69 mmol) in DMF (5 ml), triethylamine (0.19 ml, 1.38 mmol) was added, followed by succinic anhydride (138 mg, 1.38 mmol) and heated at 40° C. overnight. The solvents were removed under reduced pressure and the residue purified using silica gel flash chromatography (1:1 chloroform: methanol as the eluent). This furnished the hemisuccinate (123 mg, 48%) as a white powder (3β-(Benzoyloxy)-2β-(hydroxymethyl succinoyl)-8-methyl-8-azabicyclo[3.2.1]octane).

To a solution of the hemisuccinate (16 mg, 0.043 mmol) in distilled water (0.5 ml) at 0° C., EDC (12 mg, 0.064 mmol) was added. After 5 minutes, BSA (16 mg) in PBS (0.5 ml) was added dropwise and the solution allowed to warm to ambient temperature overnight. The conjugate solution was purified by dialysis against PBS and the degree of haptenation determined by mass spectral analysis.

EXAMPLE 5

Synthesis of PS-9

To a solution of benzoyl ecgonine (10 mg, 0.035 mmol) in distilled water (1.0 ml) at 0° C., EDC (10 mg, 0.052 mmol) was added. After 5 minutes BSA (10 mg) in PBS (0.5 ml) was added dropwise and the solution warmed to ambient temperature overnight. The protein conjugate was purified by dialysis against PBS buffer. The degree of haptenation was determined by mass spectral analysis.

EXAMPLE 6

Synthesis of CTB-PS-5

Method A

To a solution of succinylated norcocaine (2 mg, 5.14 μmol) in DMF (0.1 ml), diisopropylethylamine (2 μl, 10.3 μmol) was added followed by HATU (2 mg, 5.40 μmol). After 10 minutes, the pale yellow solution was added dropwise to a solution of CTB (0.5 mg in 0.9 ml of 10 mM borate buffer at pH 7.8) and shaken at ambient temperature for 1.5 hours. The pH of the conjugate solution was adjusted to pH 6.5 by the careful addition of 1N HCl, followed by purification by dialysis against 20 mM sodium succinate, pH 6.5. The dialysate was filtered through a 0.2 μm filter and the level of haptenation measured by mass spectral analysis or UV absorbance.

Method B

To a solution of succinylated norcocaine (2 mg, 5.14 μmol) in DMF (0.1 ml), diisopropylethylamine (2 μl, 10.3 μmol) was added followed by HBTU (1.9 mg), 5.40 μmol). After 10 minutes, the pale yellow solution was added dropwise to a solution of CTB (0.5 mg in 0.9 ml of PBS buffer at pH 7.6) and shaken at ambient temperature for 1.5 hours. The pH of the conjugate solution was adjusted to pH 6.5 by the careful addition of 1N HCl, followed by purification by dialysis against 20 mM sodium succinate, pH 6.5. The dialysate was filtered through a 0.2 μm filter and the level of haptenation measured by mass spectral analysis or UV absorbance.

Method C

To a solution of succinylated norcocaine (2 mg, 5.14 μmol) in DMF (0.1 ml), diisopropylethylamine (2 μl, 10.3 μmol) was added followed by TNTU (1.9 mg, 5.40 μmol). After 10 minutes, the pale yellow solution was added dropwise to a solution of CTB (0.5 mg in 0.9 ml of PBS buffer at pH 7.6) and shaken at ambient temperature for 1.5 hours. The pH of the conjugate solution was adjusted to pH 6.5 by the careful addition of 1N HCl, followed by purification by dialysis against 20 mM sodium succinate, pH 6.5. The dialysate was filtered through a 0.2 μm filter and the level of haptenation measured by mass spectral analysis or UV absorbance.

Method D

To a solution of succinylated norcocaine (2 mg, 5.14 μmol) in DMF (0.1 ml), diisopropylethylamine (2 μl, 10.3 μmol) was added followed by TNTU (1.9 mg, 5.40 μmol). After 10 minutes, the pale yellow solution was added dropwise to a solution of CTB (0.5 mg in 0.9 ml of 10 mM borate buffer at pH 7.8) and shaken at ambient temperature for 1.5 hours. The pH of the conjugate solution was adjusted to pH 6.5 by the careful addition of 1N HCl, followed by purification by dialysis against 20 mM sodium succinate, pH 6.5. The dialysate was filtered through a 0.2 μm filter and the level of haptenation measured by mass spectral analysis or UV absorbance.

Method E

To a solution of succinylated norcocaine (2 mg, 5.14 μmol) in DMF (0.1 ml), diisopropylethylamine (2 μl, 10.3 μmol) was added followed by PyBroP (2.4 mg, 5.40 μmol). After 10 minutes, the pale yellow solution was added dropwise to a solution of CTB (0.5 mg in 0.9 ml of PBS buffer at pH 7.6) and shaken at ambient temperature for 1.5 hours. The pH of the conjugate solution was adjusted to pH 6.5 by the careful addition of 1N HCl, followed by purification by dialysis against 20 mM sodium succinate, pH 6.5. The dialysate was filtered through a 0.2 μm filter and the level of haptenation measured by mass spectral analysis or UV absorbance.

Method F

To a solution of succinylated norcocaine (2 mg, 5.14 μmol) in DMF (0.1 ml), diisopropylethylamine (2 μl, 10.3 μmol) was added followed by PyBroP (2.4 mg, 5.40 μmol). After 10 minutes, the pale yellow solution was added dropwise to a solution of CTB (0.5 mg in 0.9 ml of 10 mM borate buffer at pH 7.8) and shaken at ambient temperature for 1.5 hours. The pH of the conjugate solution was adjusted to pH 6.5 by the careful addition of 1N HCl, followed by purification by dialysis against 20 mM sodium succinate, pH 6.5. The dialysate was filtered through a 0.2 μm filter and the level of haptenation measured by mass spectral analysis or UV absorbance.

EXAMPLE 7

Alternative Syntheses of CTB-PS-5

Method A

A solution of succinylated norcocaine (15 mg, 0.39 mol), thionyl chloride (28 μl, 0.39 mmol) in DMF (250 μl) was stirred at ambient temperature for 2 hours. After the reaction was deemed complete (by TLC analysis), the solvents were removed under reduced pressure and the resulting chloro derivative (3β-(Benzoyloxy)-8-chlorosuccinoyl-8-azabicyclo[3.2.1]octane-2β-carboxylic acid methyl ester) taken through to the next step without further purification.

The chloro derivative (16 mg, 0.04 mmol) was dissolved in DMF (100 μl) and added dropwise to a solution of CTB (0.38 mg/ml in 3 ml PBS). The resulting mixture was kept at ambient temperature overnight, dialyzed against PBS and the degree of haptenation determined by mass spectral analysis.

Method B

To a solution of succinylated norcocaine (100 mg, 0.26 mmol) in DMF (5 ml), DCC (64 mg, 0.31 mmol) was added. After 10 minutes, 4-hydroxy-3-nitrobenzene sulfonic acid sodium salt (74 mg, 0.31 mmol) was added and the resulting yellow solution kept at ambient temperature for 4 days. The resulting suspension was filtered under reduced pressure and the filtrate added to cold diethyl ether (10 ml) with vigorous stirring. Hexane (5 ml) added and after complete precipitation of a yellow oil, the colorless supernatant was decanted off. This process was repeated and the oil dried overnight under reduced pressure, furnishing the desired ester (157 mg) (3β-(Benzoyloxy)-8-(2-nitro-4-sulfophenyl ester) succinoyl-8-azabicyclo[3.2.1]octane-2β-carboxylic acid methyl ester) which was taken through to the next stage without further purification.

The ester (5 mg, 8.16 μmol) was dissolved in DMF (100 μl) and added dropwise to CTB (1 mg in 2 ml PBS) at 4° C. and then warmed to ambient temperature. After 3 hours the conjugate solution was purified by dialysis against PBS and the degree of haptenation determined by mass spectral analysis.

Method C

To a solution of succinylated norcocaine (108 mg, 0.28 mmol) in DMF (5 ml) at 0° C., NMM (37 μl, 0.33 mmol) followed by ethyl chlorofomate (32 μl, 0.33 mmol) were added. After 10 minutes, N-hydroxysuccinimide (38 mg, 0.33 mol) was added and the solution warmed to ambient temperature over 18 hours. The solvents were removed under reduced pressure and the residue recrystallized from isopropanol/diethyl ether to furnish the N-oxysuccinimidyl ester (113 mg, 84%) as a white powder (3β-(Benzoyloxy)-8-(N-oxysuccinimidoyl)succinoyl-8-azabicyclo[3.2.1]octane-2β-carboxylic acid methyl ester).

A solution of the ester (2 mg, 4.11 μmol) in DMF (100 μl) was added dropwise to a solution of CTB (1 mg in 2 ml PBS). After 3 days the conjugate solution was purified by dialysis against PBS and the degree of haptenation determined by mass spectral analysis.

EXAMPLE 8

Synthesis of a Conjugate with an Extended Spacer

To a solution of norcocaine hydrochloride (50 mg, 0.15 mmol) in DMF (1 ml), diisopropylethylamine (27 μl, 0.31 mmol) was added. After 5 minutes the solution was cooled to 0° C. and added dropwise to a solution of adipoyl chloride (44 μl, 0.080 mmol) in DMF (100 μl) at 0° C. After 2 hours the solution was added dropwise to a solution of CTB (1 mg in 2 ml PBS) at 0° C. and warmed to ambient temperature overnight. The conjugate solution was purified by dialysis against PBS and the degree of haptenation determined by mass spectral analysis.

EXAMPLE 9

Conjugation of Succinylated Norcocaine with MAP

MAP resin (Novabiochem U.S.A., La Jolla, Calif.) (substitution level: 0.48 mmol/g; 50 mg, 0.023 mmol) was pre-swollen in DMF (5 ml). The solvent was decanted and the resin treated with a solution of 20% piperidine in DMF (5 ml), agitated for 15 minutes and the solvents removed by decanting. The resin was washed sequentially with DMF (5 ml), methanol (5 ml) and DMF (5 ml). A solution of succinylated norcocaine (18 mg, 0.046 mmol) in DMF (1 ml) was treated with a mixture of HOBt/DMF/HATU (0.5M freshly prepared solution in DMF; 92 μl, 0.046 mmol) and after 5 minutes, this was agitated overnight after which the reaction was deemed to be >90% complete by the Kaiser-Ninhydrin test. The solvents were decanted off and the resin beads washed exhaustively with methanol, followed by drying under a stream of argon. The derivatized MAP was cleaved by suspending the resin in 2.5% phenol/TFA/EDT (5 ml) and agitating for 1 hour, filtered, washed with TFA (4×4 ml) and the solvents removed under reduced pressure. The crude peptide was triturated with cold diethyl ether, centrifuged for 5 minutes at 5000 rpm and the process repeated. The pellet was dissolved in water and lyophilized to give 1 mg of crude peptide.

EXAMPLE 10

Synthesis of (N-succinamidyl-cocaine)$_8$-MAP Protein Conjugate

Synthesis of the non-hapten portion (MAP core) of the poly-haptenated MAP is carried out by manual peptide synthesis as described by Tam et al (U.S. Pat. No. 5,229,490). Amino groups are protected by the Boc (t-butyloxycarbonyl) function and the sulfhydryl group of Cys is protected as its 3-nitro-2-pyridylsulfenyl (Npys) derivative. After assembly on the resin and removal of Boc protecting groups with TFA as described by Tam (supra.), the MAP core is cleaved from the resin by HF cleavage leaving the Npys group intact. Crude MAP core is taken up in 7M guanidine hydrochloride containing 0.2M HOAc and subjected to gel permeation chromatography in 0.2M HOAc on Sephadex G-10 t remove any remaining low molecular byproducts generated by the HF cleavage. The MAP core is lyophilized from 0.2M HOAc. (N-succinamidyl-norcocaine)$_8$-MAP is prepared according as described in Example 9.

Prior to coupling to activated protein the thiol group is exposed by treatment with a molar equivalent of tris-(2-carboxyethyl)phosphine hydrochloride (TCEP). Activated protein carrier is dissolved at 5 mg/ml in 0.2M sodium bicarbonate buffer at room temperature. To this solution is added a 2-fold molar excess of (N-succinamidyl-norcocaine)$_8$-MAP at 5 mg/ml. The reaction is allowed to proceed for 20 hours at room temperature and then dialyzed overnight against 0.2M HOAc and lyophilized.

EXAMPLE 11

Testing the Induction of Cocaine Specific Antibody Response

In order to induce an antibody response against a small molecule or hapten, such as cocaine, it is necessary to link it to a T cell epitope-containing carrier, e.g., a protein carrier. The carrier is recognized by T cells which provide help to the cocaine-specific B cells for initiation and maintenance of sustained antibody production. In this example, the carrier used was BSA, a protein which has 36 lysine residues that are exposed and available for conjugation. A panel of structurally distinct cocaine-protein conjugates were produced that were linked through different regions of the cocaine molecule (FIGS. 1a, 1b, 2a, 2b). A set of conjugates was synthesized because the cocaine molecule is physically altered and differently oriented during the conjugation process to the carrier. Since any given cocaine conjugate may induce antibodies which recognize the conjugate only, and not the free hapten (cocaine) itself, screening was performed.

Figure 9B:
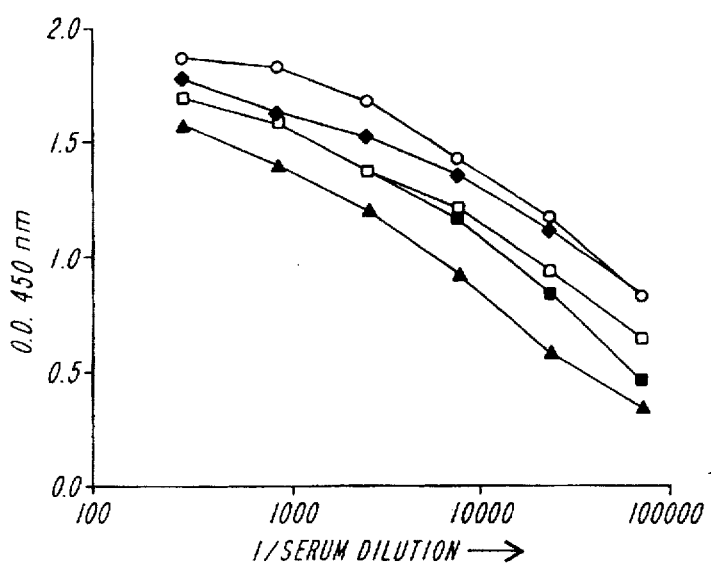
FIG. 9b is a graph showing the IgG antibody response in mice immunized with cocaine conjugate (PS-5.5 Alum i.p.) of the instant invention. The antibody response is detected by in vitro binding to the appropriate HEL conjugate made using HEL rather than BSA as a carrier. Mice received 2 injections of 50 µg per injection. The curves represent the response of 5 individuals mice per group.
Figure 9C:
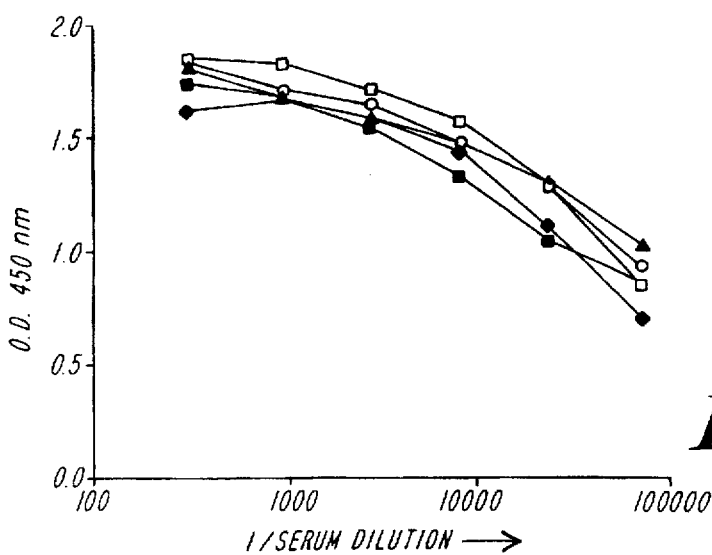
FIG. 9c is a graph showing the IgG antibody response in mice immunized with cocaine conjugate (PS-9.2+CFA i.p.) of the instant invention. The antibody response is detected by in vitro binding to the appropriate HEL conjugate made using HEL rather than BSA as a carrier. Mice received 2 injections of 50 µg per injection. The curves represent the response of 5 individuals mice per group.

Mice were immunized with 50 μg of cocaine-BSA conjugate PS-5.1 and PS-5.6 (FIGS. 9a and b) or with PS-9.1 (FIG. 9c) i.p. either with CFA (FIGS. 9a and 9c) or with alum (FIG. 9b). Mice were boosted one time and then bled. The mice immunized with cocaine-BSA conjugate PS-5.1 were boosted with cocaine-BSA conjugate PS-5.6. Sera were tested in an ELISA assay using plates coated with PS-5 (conjugated to HEL) or PS-9 (conjugated to HEL) as appropriate. The responses of 5 individual mice per group are shown. These data demonstrate that the cocaine-BSA conjugates are able to induce high titer antibody responses.

EXAMPLE 12

Recognition of Free Cocaine

To directly determine whether the induced antibodies were capable of recognizing the free cocaine molecule, a competition ELISA was established. Plates were coated with appropriate free cocaine-HEL conjugate and incubated with the antisera at a 1:2000 dilution in the presence of varying concentrations of free cocaine as competition. When PS-5,6-BSA was used as the immunogen, the majority of the antibody response was effectively competed by free cocaine (FIGS. 10a and b) In this set of sera from ten mice, (each line on the graph in FIG. 10a indicates a different mouse) one was less effective in the competition assay (open squares and dotted line), and this mouse was not used in the $LD_{50}$ experiments described herein. The PS-9,2-BSA conjugate also induces cocaine-specific antibodies. These data demonstrated that cocaine-carrier conjugates can be synthesized which induce high-titer, cocaine-specific antibody responses that should be capable of neutralizing cocaine in vivo.

EXAMPLE 13

Ability of Vaccination to Protect Against Cocaine Toxicity

The present invention discloses a cocaine-protein conjugate that induced an anti-cocaine antibody response in a mouse model. These anti-cocaine antibodies neutralized cocaine in vivo, significantly shifting the dose of cocaine required to induce a lethal response in mice.

The efficacy of therapeutic vaccination against cocaine was assessed by determining the lethal dose of cocaine ($LD_{50}$) in immunized and naive animals. The prediction was that a strong cocaine-specific antibody response should bind sufficient quantities of cocaine to prevent the rapid cardiac, respiratory, and neurological effects of cocaine, thus increasing the $LD_{50}$ of cocaine in the immunized mice. Sixty BALB/c mice were immunized with 50 μg PS-5,4-BSA in CFA and boosted only once with the same conjugate in IFA. Each of the mice was bled at day 34 and serum antibody titers and competition with cocaine were assessed. Forty-eight mice were chosen for the experiment, with average titers of 18,700, all of which displayed competition with free cocaine. For the $LD_{50}$ experiment, 4–6 mice were used per group and each group was carefully matched for antibody titer and apparent affinity for free cocaine.

Figure 11B:
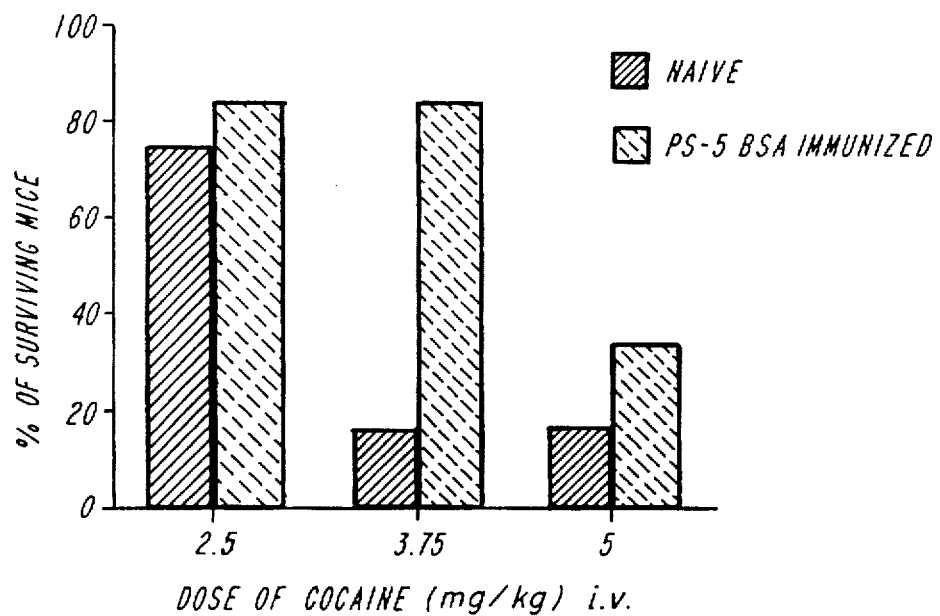
FIG. 11b is another bar graph illustrating that a cocaine-BSA conjugate prepared according to the method of the instant invention provide two-fold protection in high dose cocaine $LD_{50}$.

As shown in FIG. 11, the $LD_{50}$ for cocaine in naive BALB/c mice was 3 mg/kg when the drug was given intravenously (i.v., FIG. 11b) and 20 mg/kg when given intraperitoneally (i.p., FIG. 11a). Immunization of mice with the cocaine-protein conjugate changed the $LD_{50}$ significantly. The doses required for half-maximal toxicity were 4.5 mg/kg and 35 mg/kg for the i.v. and i.p. doses, respectively. These doses were significantly different from the value obtained in the naive mice (p=0.048 for i.v. and p=0.014 for i.p., Cochran-Mantel-Haenszel Chi-squared test). The almost two-fold protection of acute high dose toxicity by cocaine vaccination compares favorably with some drugs affecting cocaine pharmacology. For example, the NMDA antagonist MK-801 increased the $LD_{50}$ 1.3-fold and 1.4-fold when combined with propanolol (Itzhak et al. (1992) *J. Pharmacol. Exp. Therap.* 262:464–467). In addition, vaccination significantly prolonged the time to death from an average of 3.2 min to 5.4 min. for i.v. administration (p=0.007, Wilcoxon 2-sample test) and from 4.0 min to 8.5 min. for i.p. administration (p=0.0003). This study demonstrates that the antibody affected the in vivo physiological response to high dose cocaine.

EXAMPLE 14

Discrimination of Cocaine from Saline in Rat Model

To demonstrate the stability and reproducibility of this system, 8 rats are trained to discriminate i.p. injections of 10 mg/kg cocaine from saline using a 2-lever procedure (Kantak et al. (1995) *J. Pharmacol. Exp. Therap.* 274:657–665). After cocaine injections are given, the animals are required to press one of the levers (drug-appropriate lever) 10 times (FR 10) to obtain a food pellet; upon saline injections, they are required to press the other lever (saline-appropriate lever) 10 times to obtain a food pellet. When animals have learned to discriminate cocaine from saline, at least 90% of the total responses are made on the appropriate lever for several consecutive days. In order to incorporate a cumulative dosing procedure during later substitution test sessions, training sessions are made up of multiple components, each lasting for 10 min or until 10 FRs are completed, whichever occurred first.

Following training, substitution test sessions with different doses of cocaine (0.3–17.8 mg/kg) are conducted twice weekly, with training sessions on intervening days. Drug substitution test sessions consisted of four 10 min components, each preceded by a 15 min time-out period. During substitution tests, completion of 10 responses on either lever produce a food pellet. Incremental doses of cocaine are injected at the beginning of each of the 4 time-out periods. Overlapping ranges of cumulative doses are studied on different test days, permitting a seven-point cumulative dose-response curve to be determined in a single week.

In substitution tests, cocaine engendered dose-related increases in the percentage of cocaine-appropriate responses, which result in full substitution (>90% cocaine-appropriate responses) for all subjects after administration of doses that are at least the level of the training dose. Each data point is based on 2–3 determinations in individual subjects. The $ED_{50}$±95% C.I. for cocaine-appropriate responses is 2.14±0.20 mg/kg, which compares favorably to the value obtained in rats trained to discriminate injections of 10 mg/kg cocaine using single component and single dosing procedures (2.6±0.29 mg/kg; (Kantak et al. (1994) *J. Pharmacol. Exp. Ther.* (under review)).

EXAMPLE 15

Assays to Detect the Function Activity of CTB

Figure 14A:
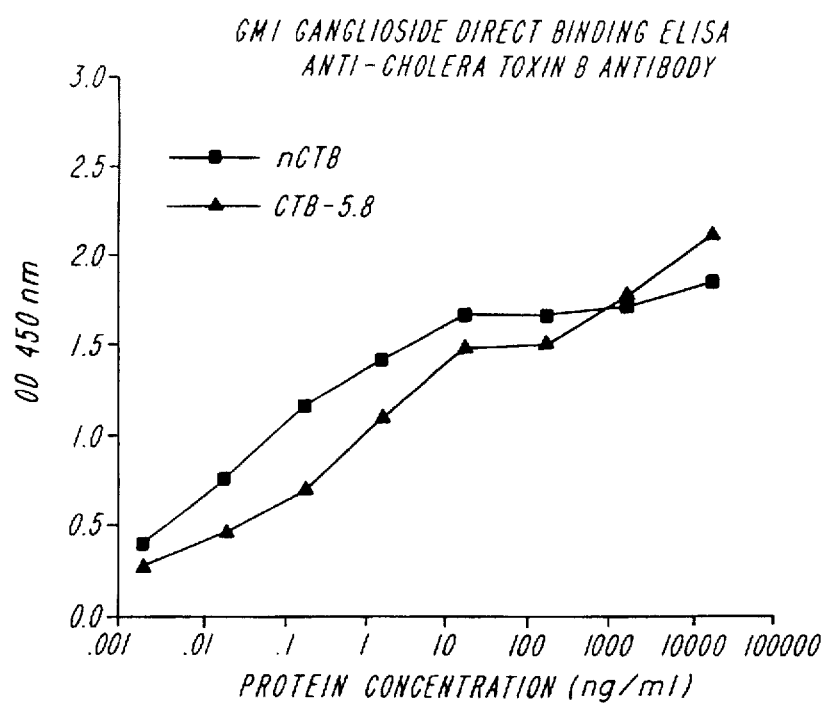
FIG. 14a is a graph representing an ELISA in which native CTB and cocaine-CTB conjugate CTB-5.8 (PS-5.8 conjugated to CTB) are shown to be pentameric, based on their ability to bind to ganglioside $G_{M1}$.
Figure 14B:
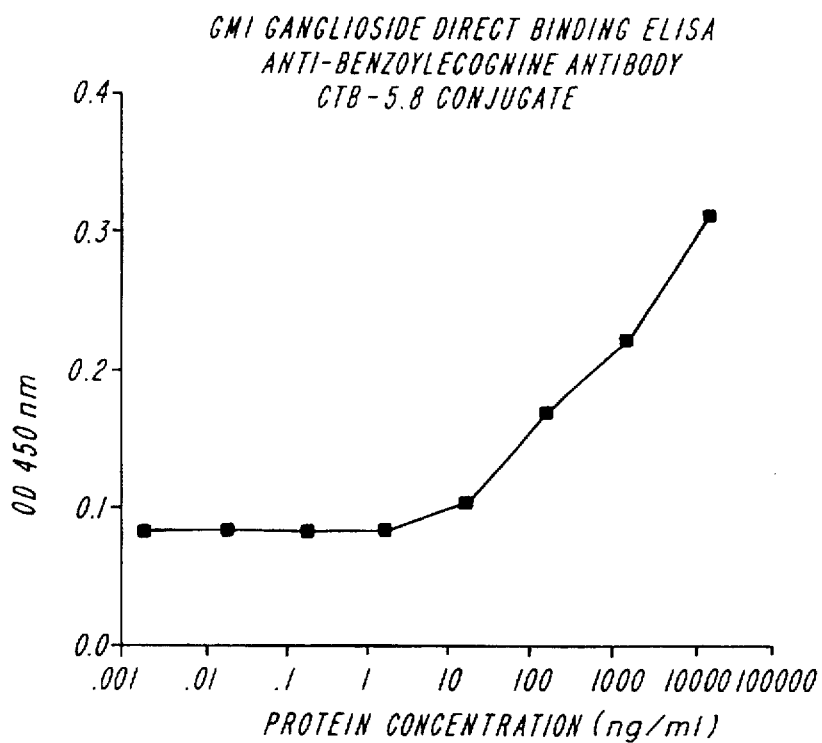
FIG. 14b is a graph representing an ELISA in which CTB-5.8 (PS-5.8 conjugated to CTB) is bound to ganglioside $G_{M1}$ and the conjugate is detected with an anti-cocaine (anti-benzoylecgonine) monoclonal antibody.

To test the functional activity of CTB alone, two assays were developed. First, binding of CTB to cells was measured using flow cytometry. Cells were incubated with CTB, followed by a commercial anti-CTB goat antiserum and a fluorescein isothiocyanate (FITC)-labelled anti-goat secondary antibody (FIG. 13). Native pentameric CTB bound to the cells, causing a dramatic shift in fluorescence intensity. Monomeric CTB was unable to bind to cells in this assay. Second, an ELISA was set up to measure the ability of the CTB to bind to ganglioside $G_{M1}$. ELISA plates were coated with $G_{M1}$-ganglioside and incubated with varying concentrations of CTB. Binding was detected using an anti-CTB antibody (or saline as a control) followed by enzyme-labelled second antibody and development with substrate. This assay provided a quantitative and extremely sensitive measure of the ability of pentameric CTB to bind to $G_{M1}$ gangliosides. These assays are used to monitor the functional activity of recombinant and haptenated CTB conjugates prior to experiments in vivo. Similarly, FIG. 14a shows that conjugation does not affect the ability of CTB-specific antibodies to recognize the conjugate. FIG. 14b shows that the conjugated CTB molecules which are able to bind $G_{M1}$ can also be bound by cocaine-specific antibodies, demonstrating the retention of CTB activity by haptenized CTB.

EXAMPLE 16

Self-Administration Model of Addiction and Effect of Vaccine

In rats, the reinforcing stimulus properties of cocaine can be studied reliably using intravenous self-administration procedures. This is a direct model of addiction and drug self-administration behavior in animal subjects which positively correlates with abuse of that drug by human subjects. To examine the effect of the therapeutic vaccine, adult male rats (Wistar, approximately 300 g) are implanted with a chronic jugular vein catheter using the general procedures described by Weeks (*Meth. Psychobiol.* (1972) 2:115–168) and as adapted by Kantak et al. (Kantak et al. (1990) *Pharm. Biochem. Behavior* 36:9–12; (Kantak et al. (1991) *Psychopharm.* 104:527–535; and Kantak et al. (1992)*Pharmacol. Biochem. Behav.* 41:415–423). All animals are housed individually and maintained at 80%–85% of their free feeding body weights to facilitate comparison with the drug discrimination experiments. One week following surgery, 1.0 mg/kg/infusion of cocaine is available as the training dose in daily 2 hr sessions. Rats typically self-infuse a cumulative dose of 10 mg/kg each hour. During the initial phase of training, each lever press results in drug delivery. The required number of responses to self-infuse cocaine is increased gradually to 5 (FR 5) and then the FR 5:FI 5 min schedule of drug delivery is introduced. Following stable responding for at least 5 days, a baseline cocaine dose-response curve (0.1, 0.3, 0.56, 1.0 and 3.0 mg/kg/infusion) is determined. Each dose of cocaine, as well as saline, is examined for a block of at least 5 sessions and until no systematic upward or downward trends in responding are observed. Data is expressed as mean response rates over the last two days of each block of sessions.

Following determination of the baseline cocaine dose-response curve in 30 rats, half the rats are immunized with the optimal cocaine-carrier conjugate and the other half are immunized with carrier alone. Self-administration sessions are discontinued until significant anti-cocaine antibody titers are achieved, which should take 4–6 weeks. Rats are bled from the tail vein to ensure that all rats have comparable titers of cocaine-specific antibodies. Following immunization, the rats are tested for their ability to respond to cocaine. Rats will have access to varying doses of cocaine (0.3–3.0 mg/kg/infusion), or to saline, in 5-day blocks. Control rats immunized with carrier alone quickly return to the baseline pattern of cocaine self-administration.

Anti-cocaine antibody blocks the reinforcing effects of cocaine. If necessary, doses of cocaine up to 30 mg/kg/infusion are examined to determine how much protection the antibody affords. If the anti-cocaine antibody partially blocks cocaine, the rats require much larger doses of cocaine to achieve the desired physiological effect and responses maintained by cocaine are reinstated with a rightward shift in the cocaine dose-response curve. If the polyclonal cocaine antibody completely blocks doses of cocaine up to 30 mg/kg/infusion, then responding which is maintained by cocaine is not reinstated and cocaine self-administration extinguishes, with the cocaine dose-response curve remaining flat at near-zero saline-like levels.

Cocaine self-administration can also be inhibited by passively administered anti-cocaine antibody. Monoclonal anti-cocaine antibody or control antibody was administered to separate groups of rats. Animals that had been previously stabilized on a FR5: FI5 schedule of cocaine administration extinguished their self-administration of cocaine if passively treated with anti-cocaine antibodies. Rats treated with control antibody maintained their cocaine self-administration responses.

EXAMPLE 17

Co-Treatment with Other Drugs

Screening is done to determine whether pharmacotherapy with buprenorphine and/or desipramine will enhance the activity of the therapeutic vaccine. Treatment with buprenorphine and/or desipramine are expected to be compatible. It is possible that the therapeutic agents could be immunosuppressive, thus inhibiting the induction of a high titer anti-cocaine antibody response. To address this possibility, rats are immunized with the cocaine-carrier conjugate in the presence or absence of buprenorphine or desipramine and the antibody titer is measured at varying times. A drug which is found to be significantly immunosuppressive will be eliminated as an incompatible therapy. This screening test is used for any drug for which co-treatment is considered.

If no immunosuppression is seen, further screening is carried out to determine if the two approaches synergize. Following training, immunization and testing, rats are further evaluated in the two models in the presence of the drugs. Rats will receive drugs before sessions with different doses of cocaine. Initial experiments with control carrier-immunized rats are performed to choose a dose of drug that does not completely extinguish behavior in the self-administration or drug discrimination systems; it is estimated that this dose is approximately 5.6 mg/kg (−)-buprenorphine or 10 mg/kg desipramine. Data is evaluated to determine whether the action of the therapeutic vaccine is additive with the treatment with buprenorphine or desipramine.

EXAMPLE 18

Induction of Mucosal Response

The B subunit of cholera toxin (CTB) has been shown in many systems to retain the activity of intact cholera toxin, including the induction of a mucosal antibody response. Therefore, this carrier should induce a strong anti-cocaine IgA antibody response.

An effective way to prime an immune response in the respiratory tract is to deliver antigen directly to those sites. The antigen is administered in saline, with CTB acting as its own adjuvant. To confirm the ability of CTB to prime a mucosal IgA response, initial experiments are conducted with carrier alone. Mice are primed with 50 µg of the CTB or cocaine-CTB conjugate by two routes: nasally or intratracheally. Nasal administration is a simple and common route of priming. Antigen is applied to each nostril of a lightly anesthetized mouse, for a total volume of 50 µl per mouse. Fourteen days after priming, the mice are boosted using the same protocol. Nasal administration is adaptable readily to human application as a nasal spray. Nasal vaccination has been used successfully with live influenza vaccines (Walker et al. (1994) *Vaccine* 12:387–399).

Intratracheal immunization directly applies the antigen to the lower respiratory tract, thereby enhancing immunity in the lungs. Mice are anesthetized with a cocktail of ketamine and xylazine. The animals are mounted on an apparatus that holds their mouth open and exposes the trachea; the trachea is visualized with a fiberoptic light probe. A blunt 23 gauge needle is used to deliver 50 µl of solution into the lungs. Fourteen days after priming, the mice are boosted using the same protocol.

Animals are sacrificed by $CO_2$ asphyxiation at varying time points after boost (14, 21, or 28 days) and nasal and bronchoalveolar lavage fluids are collected and assayed for IgA specific for the administered conjugate. Nasal wash fluid is obtained by washing the nasal cavity four times with a total of 1 ml PBS as described (Tamura et al. (1989) *Vaccine* 7:257-262. Bronchoalveolar lavage fluid is obtained by surgically exposing the trachea, injecting 0.5 ml PBS into the lungs, and rinsing three times as described (Nedrud et al. (1987) *J. Immunol.* 139:3484-3492). Following centrifugation to remove cells, samples are assayed for antigen-specific IgA by ELISA using an IgA-specific second antibody. Cocaine-specific IgG is measured in the nasal and lung washes, as it has been reported that IgG is frequently both detectable and important in the lung (Cahill et al. (1993) *FEMS Microbiol. Lett.* 107:211-216).

The two routes of administration are compared directly for their ability to induce an IgA response in both the lung or nasal lavage fluid. Whichever route is found to be most potent, it is preferred and used for the remaining experiments. If the two routes are of comparable efficacy, nasal immunization is preferred because of its simplicity.

For maximal protection against cocaine, systemic IgG and mucosal IgA responses may both be maximized. Therefore, both a systemic injection with the cocaine-CTB conjugate in alum (or some other adjuvant) and a mucosal challenge with the conjugate are preferred to effectively prime both compartments. Three groups are compared. First, mice are primed systemically, followed by a mucosal challenge after 14 days. Second, the mice are primed mucosally, followed by a systemic challenge after 14 days. Third, they are primed both systemically and mucosally at the same time, followed by an identical boost after 14 days. Control mice are primed only mucosally or only systemically. In each case, efficacy in challenge is determined by measurement of both IgG and IgA anti-cocaine antibody titers.

As an initial measure of the in vivo efficacy of mucosal anti-cocaine antibodies, the $LD_{50}$ is measured for mucosally administered cocaine. Varying doses of cocaine are administered to anesthetized mice either intratracheally or intranasally. Three groups of mice are compared in the $LD_{50}$ experiment: naive mice, mice which only have been immunized systemically and mice which have been immunized both systemically and mucosally. The actual $LD_{50}$ of all groups may be shifted by anesthetization (Tella et al. (1992) *J. Pharm. Exper. Therap.* 262:936-946). This approach can also be pursued in a non-human primate model of cocaine using smoked cocaine base (Carroll et al. (1992) *J. Pharm. Exper. Therap.* 261:26-37).

EXAMPLE 19

Immunogenicity of Cocaine-CTB Conjugates
A. Definition of Dose Required for Immunogenicity The immunogenicity of cocaine-CTB conjugates was determined by immunization of rodents with cocaine-CTB, boosting where appropriate, and assessing antibody levels at varying times. Antibody levels were measured in an antigen-specific ELISA. Antibody titers were determined as the reciprocals of the serum dilution giving 50% of the maximal response in the ELISA and are expressed as the geometric means of the results from 5 or more mice.

To determine the range of antigen dose required to induce an anti-cocaine antibody response, mice were immunized either subcutaneously or intramuscularly with varying doses of cocaine-CTB PS-5.53. Animals were boosted on days 23 and 59 and bled on day 71. Doses of 3, 10, and 30 μg given intramuscularly induced titers of cocaine-specific IgG of 18429, 29013, and 22957, respectively. Using s.c. immunization, the same doses induced specific antibody titers of 10097, 15136, and 21169. These data demonstrate that cocaine-CTB can be effectively used in the range of 3–30 μg and greater and lower doses are expected to be effective. Similar doses are also effective for use in rats. Those skilled in the art use this data to identify optimal human doses, which are usually comparable.

B. Immunization on Mucosal Surfaces

To generate optimal antibody responses in mucosal secretions, it is usually necessary to prime at a mucosal surface. To determine whether CTB would be a useful carrier protein for the induction of a mucosal antibody response, mice were immunized intranasally or intratracheally. The methods for intranasal and intratracheal immunization are described in Example 18. Intranasal immunization with cocaine-CTB induced significant levels of circulating cocaine-specific IgG, although the titers were lower than those seen following subcutaneous or intramuscular immunization. As with the routes of administration described in Part A of this example, doses of cocaine-CTB of 3–30 μg all induced significant levels of cocaine-specific antibody. Simultaneous immunization by subcutaneous and intranasal routes induced antibody titers indistinguishable from those induced by the subcutaneous route alone. The feasibility of the intratracheal route of immunization was assessed by immunization with CTB alone. This route was also found to induce antigen-specific IgG in the serum (CTB-specific in this case). These data demonstrate that CTB is capable of inducing a systemic antigen-specific IgG response following immunization at a mucosal surface in the absence of any added adjuvant.

C. Induction of Cocaine-Specific Antibodies in Mucosal Secretions

To maximize protection against the addictive properties of cocaine, it is desirable to optimize the levels of cocaine-specific antibody at the sites of cocaine application (e.g. nasal and lung mucosa) as well as in the blood. Mice were immunized intranasally or subcutaneously with 10 μg cocaine-CTB and were boosted using the same protocol on days 27 and 61. Following sacrifice on day 78, bronchial and nasal washes were collected as described in the Examples and assayed for cocaine-specific IgA and IgG. Anti-cocaine antibodies were detectable in both the nasal and bronchial washes using both immunization regimens. Intranasal immunization induced higher levels of antigen-specific IgA, while both routes were comparable at inducing anti-cocaine IgG responses in the mucosal secretions. The intranasal route of administration was also found to be the most effective route for the induction of antigen-specific IgA in the serum. Intratracheal immunization with CTB also induced CTB-specific IgA and IgG in the respiratory secretions. These data demonstrate that CTB is an effective carrier protein for the induction of an antigen-specific antibody response in the respiratory tract.

D. Use of Alum as Adjuvant for Immunization

The use of adjuvant is often beneficial in immunization protocols. To assess the contribution of alum to the immune response, mice were immunized with 10 μg cocaine-CTB PS-5.53 intraperitoneally in saline or adsorbed onto alum. The mice were boosted at day 27 using the same protocol. For both groups of animals, high levels of cocaine-specific antibodies were detected by day 43 (titer of 14687 without alum and 16775 with alum). Immunization with cocaine-CTB adsorbed onto alum has also been shown to be effective with a subcutaneous or intramuscular route of administration. Therefore, the use of alum is acceptable with this antigen.

E. Duration of Antibody Responses

To determine whether antibody responses induced with cocaine-CTB PS-5.8 are long-lasting, serum antibody levels were monitored as a function of time. The animals described in section D of this Example were monitored out to day 128 after immunization. At that time point, antibody titers remained high, dropping approximately 2-fold from the peak at day 43. These data demonstrate that anti-cocaine antibody responses to cocaine-CTB conjugate are long-lasting.

F. Relative Levels of Anti-Hapten and Anti-Carrier Antibody Response

Immunization with cocaine-CTB induces an antibody response against both the hapten (cocaine) and the carrier (CTB). CTB is a very powerful immunogen and it is possible that the anti-CTB response could dominate, preventing the anti-cocaine response from reaching very high titers. To determine whether it was possible to differentially regulate the anti-cocaine and anti-CTB antibody response to CTB by changing the immunization regimen, the following nonlimiting test was performed. Mice were intramuscularly immunizated with 30 µg cocaine-CTB and monitored for antibody response. This immunization induced both anti-cocaine and anti-CTB antibodies with the relative ratio of the serum IgG titers being 0.04. In contrast, a ratio of 0.2 was seen when the mice were immunized with 3 µg cocaine-CTB. These doses of 3 µg and 30 µg produce similar titers of 18429 and 22957, respectively. It is likely that the ratio of anti-cocaine to anti-CTB antibodies will also be affected by other parameters of the immunization regimen as well as by properties of the conjugate itself, such as level of haptenation.

EXAMPLE 20

Direct Binding of Cocaine by Antibodies From Immunized Mice

Figure 10B:
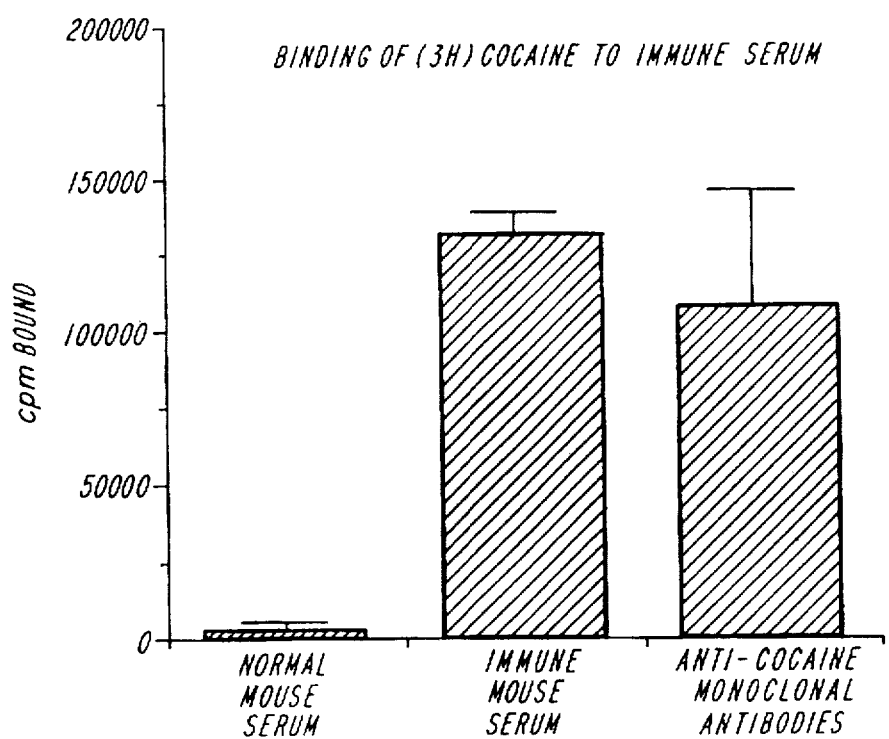
FIG. 10b is a bar graph showing that immune antiserum can bind $^3$H-cocaine.

The ability of the antibodies to bind free cocaine can be assessed using radiolabelled cocaine. $^3$H-Cocaine (1 µCi) was incubated with serum from normal mice (0.05 ml), with serum from mice immunized with a PS-5.4 conjugate (conjugated with BSA) (0.05 ml, pool of serum from 10 mice) or with commercially available anti-cocaine monoclonal antibodies (mixture of two different antibodies, 2 µg of each) (see FIG. 10b). Beads coated with protein G were included in the incubation to bind to the Fc portion of antibody molecules. After 2 hours, the beads were pelleted by centrifugation, washed three times with cold PBS and counted in a scintillation counter. The data in FIG. 10b represent the mean and standard deviations of duplicate samples. These data clearly show that the immune serum is able to bind free cocaine with an affinity sufficiently high to permit the bound cocaine to be precipitated and washed. This is evidence that these antibodies will be able to bind and neutralize cocaine in the circulation of cocaine addicts.

EXAMPLE 21

Specificity of Cocaine-Specific Antibodies

To analyze the specificity of the anti-cocaine antibodies induced by the cocaine vaccine, sera from the mice immunized with cocaine-CTB conjugate were tested in a competition ELISA. A panel of metabolites of cocaine and related molecules were tested at varying concentrations. If the antibodies had high affinity for the metabolite, then low concentrations would be capable of effectively competing in this assay. The relative reactivity is expressed as the $IC_{50}$, the concentration of the inhibitor that decreases the ELISA signal by 50%. Using this method, it was determined that the antibodies elicited by immunization with cocaine-BSA PS-5.6 effectively recognized both norcocaine, the pharmacologically active metabolite of cocaine, and cocaethylene, the active derivative of cocaine produced by transesterification following consumption of alcohol. In contrast, the antibodies recognized only poorly the pharmacologically inactive metabolites benzoylecgonine and ecgonine methyl ester. Antibodies induced by cocaine-BSA PS-5.6 and cocaine-CTB PS-5.53 displayed similar specificity, demonstrating that the carrier protein does not affect the specificity of the anti-cocaine antibodies. A highly specific monoclonal antibody was raised from a cocaine-BSA immunized animal which also displayed very similar specificity for cocaine and its active metabolites. The reactivity of this monoclonal antibody was 2000 times greater to cocaine than to benzoylecgonine.

EXAMPLE 22

Quantification of Cocaine-Specific Antibody

Without intending to limit the invention, one method of directly quantifying the antigen binding capacity and affinity of the antigen-specific antibodies obtained using the cocaine conjugate vaccine is disclosed. The classical immunochemical technique of equilibrium dialysis is used. Immune sera elicited by immunization with cocaine-BSA PS-5.6 and control antisera were placed inside dialysis bags (cellulose ester, 25,000 MWCO, Spectrum, Los Angeles, Calif.) and dialyzed to equilibrium against a large volume containing various concentrations of $^3$H-cocaine in PBS. This allowed measurement of the amount of cocaine bound to the antibody and the amount that was unbound. Data were analyzed both by plotting the amount of bound cocaine as a function of amount of total cocaine and by Scatchard plot (bound versus bound/free antigen). As expected, the antisera contained a heterogeneous mixture of antibodies with affinities ranging from $1\times10^{-7}$ to $-1\times10^{-10}$M. Measured cocaine binding capacity was up to about 10 µM, indicating a concentration of antigen-specific antibody of about 0.7 mg/ml. Therefore, immunization with the cocaine conjugate vaccine can produce antibodies with a range of useful affinities and with high cocaine binding capacities, such that a substantial proportion of the total antibody in the circulation can react with and neutralize cocaine.

EXAMPLE 23

Efficacy of Cocaine-Specific Antibody in Inhibiting Cocaine Distribution in vivo A. Inhibition of Cocaine Distribution to the Brain To assess changes in cocaine tissue distribution caused by cocaine-specific antibody, $^3$H-cocaine distribution was followed in PS-5.7 cocaine-BSA-immunized mice compared to BSA-immune control mice. Immune and control immunized mice were injected with 0.5 mg/kg $^3$H-cocaine i.v. and then decapitated at 0.5 minutes after injection. Brains, hearts and blood (plasma) were removed for subsequent analysis of tissue and plasma cocaine concentration. Blood was collected into tubes containing sodium fluoride solution to inhibit esterases and containing EDTA to prevent clotting. Brains, hearts and plasma samples were placed into scintillation vials containing tissue solubilizer; digestion of samples occurred over 3 days at room temperature. The samples were decolorized and scintillation cocktail was added to each sample. Glacial acetic acid was added to clarify the samples. After the samples were counted in a scintillation counter, data were converted to ng/g or ng/ml of tissue. Cocaine concentration in the brain tissue was significantly lower (n=10, p<0.05) at 0.5 minutes after injection (636.1±57.5 ng/g (mean±SEM) for cocaine-BSA-immunized vs. 1052.2±93.85 ng/g for BSA-immunized mice).

Several groups of mice were injected two times i.v. with 0.5 mg/kg cocaine to determine the ability of cocaine-specific antibody to inhibit distribution of repeated doses of cocaine. Only the second dose of cocaine, given 10 minutes after the initial dose, included the $^3$H-cocaine. The antibody inhibited the distribution of the cocaine redose to the brain tissue in cocaine-BSA-immunized mice (443.6±48.5 ng/g), compared to BSA-immunized mice (948.9±43.3 ng/g (n=10, p<0.001)). Thus, the inhibition of cocaine distribution after the second dose of cocaine was similar to the inhibition of distribution after one dose.

B. Inhibition of Distribution to Cardiac Tissue

Immune and control immunized mice were anesthetized and intravenously injected with 0.015 mg/kg $^3$H-cocaine and were decapitated 0.5 minutes after injection. Brains, hearts and blood (plasma) samples were removed for subsequent analysis of cocaine concentration. The concentration of cocaine in heart tissue of cocaine-BSA immune mice at 5.7±0.78 ng/g was significantly lower than that of control BSA mice at 23.4±4.6 ng/g (n=5,p<0.001). The inhibition of cocaine distribution to heart tissue in cocaine-immunized mice was equal to or greater than the inhibition of cocaine distribution to brain tissue.

C. Inhibition of Cocaine Tissue Distribution After Intranasal Administration

Effects of cocaine-specific antibody after intranasal cocaine administration were compared to effects after intravenous cocaine administration. In intranasal administration the kinetics of distribution are different from intravenous administration. Immune or control mice were anesthetized and 1 mg/kg $^3$H-cocaine was intranasally administered in 50 μl PBS. Cocaine levels did not peak until 2–5 minutes after intranasal administration, as opposed to a 15 second peak after intravenous injection. Therefore, two minutes after cocaine injection mice were decapitated and brains and blood (plasma) samples were removed for subsequent analysis of cocaine concentration. In comparing intranasal cocaine administration to intravenous administration, total levels of cocaine in the brains of control mice are fairly equal (1538 ng/g intranasally versus 2260 ng/g intravenously).

The distribution of cocaine to the brain after intranasal cocaine administration was inhibited by the presence of anti-cocaine antibody. Significant inhibition of brain distribution of cocaine was measured after cocaine was intranasally administered to cocaine-BSA-immune mice (708.3±82.8 ng/g), compared to control mice (1538.1±49.5 ng/g (n=5, p<0.0001)).

D. Antibody Titer

Mice with varying levels of cocaine-specific antibody were compared to determine how antibody titer may affect the level of inhibition of cocaine distribution. Groups of mice immunized in this study achieved titer levels ranging from 6,000 to 256,000. 0.015 mg/kg of $^3$H-cocaine was administered to mice having low titer (about 6,000 to 18,000) or high titer (about 54,000 to 256,000) anti-cocaine antibody. Thirty seconds after i.v. injection, mice were decapitated and brains and blood (plasma) samples were removed for analysis of cocaine distribution.

Mice with high antibody titers inhibited the distribution of cocaine to the brain highly significantly (control mice: 26.1±2.0 ng/g, cocaine-immunized mice: 8.9±1.2 ng/g; n=10, p<0.0001). In contrast, mice with low titers displayed a reduced ability to inhibit the distribution to the brain (control mice: 24.4±2.98 ng/g; cocaine immunized mice, 15.7±3.4 ng/g).

E. Cocaine Metabolism

To determine whether cocaine-specific antibody alters cocaine metabolism in vivo, cocaine metabolites were analyzed over time in cocaine-immune and control mice. Plasma samples tested were obtained as in animal experiments described and performed in Part A of this Example. The time point tested for metabolite composition was 30 minutes. The method for preparing the plasma for analysis is described above in Part A.

Plasma samples were aliquoted and non-radioactive cocaine, benzoyl ecgonine, and norcocaine were added in order to assist in the UV visualization of the compounds. Samples were then applied to silica TLC plates which were developed in two solvent systems: methanol, chloroform, and triethylamine (3:1:0.1); and ethyl acetate, methanol, water, and concentrated ammonia (85:10:3:1). Metabolites were identified by reference to control compounds run on the same plates. The bands were scraped off the plates and $^3$H-containing compounds were detected through scintillation counting. From the counts obtained the amount of cocaine, benzoyl ecgonine, benzoic acid, and norcocaine as percent of total counts was determined. The total radioactivity in the plasma was determined by scintillation counting of whole plasma. Benzoic acid is detected as a metabolite when cocaine degrades into ecgonine methyl ester and benzoic acid, and so is equimolar to the ecgonine methyl ester metabolite.

The anti-cocaine antibodies appear to have no detectable effect on cocaine metabolism in vivo. After 30 minutes the metabolites found are as follows, expressed as percent of total:

| Metabolite | Coc-BSA Immune | BSA Control |
| --- | --- | --- |
| Cocaine | 19.66 +/− 7.5 | 17.31 +/− 3.7 |
| Norcocaine | 5.5 +/− 0.93 | 3.6 +/− 0.93 |
| Benzoic Acid | 47.51 +/− 8.5 | 50.28 +/− 4.4 |
| Benzoyl Ecgonine | 27.3 +/− 0.6 | 29 +/− 7.2 |

F. Disappearance of Cocaine From Plasma

In order to determine whether cocaine-specific antibody changes the rate of disappearance of cocaine from the plasma, plasma samples collected at different times after cocaine injection in cocaine-BSA-immunized animals and in BSA-immunized animals were analyzed. Immune and control immunized mice were injected with 1 mg/kg $^3$H-cocaine i.v. and then decapitated at 0.5, 5 or 30 minutes after injection. Brains and blood (plasma) were removed for subsequent analysis for brain and plasma cocaine concentration, percent of cocaine bound to antibody, and TLC for quantitation of cocaine and cocaine metabolites in plasma.

Plasma was analyzed as described above in Part E above for percent of total radioactivity in the form of cocaine and any metabolites. Plasma samples were also analyzed for total radioactivity. The rate of disappearance of cocaine from the plasma of cocaine-BSA-immunized mice was compared to the rate of disappearance of cocaine from BSA-immunized mice. In this analysis, the small fraction of norcocaine (less than 5%) was considered with the cocaine since norcocaine has CNS activity and binds to antibody. This does not alter the results described below.

Cocaine disappears from the plasma of both groups of animals at very similar rates. Between 30 seconds and 30 minutes, about 80% of the cocaine had disappeared from the plasma of both groups of animals. The disappearance of cocaine in plasma at these times after injection was due to both redistribution and metabolism. Although cocaine disappears at the same rate in the two groups of animals, there is more cocaine in the plasma of the cocaine-BSA-immunized mice than in plasma from the BSA-immunized mice at all times. The presence of cocaine-specific antibody did not detectably alter the duration of cocaine.

G. Percent of Cocaine Bound to Antibody

The inhibition of distribution as shown above is possible if cocaine is bound to antibody in the same animal. To determine the degree of binding of plasma cocaine to antibody, immune and control immunized mice were injected with 1 mg/kg $^3$H-cocaine i.v. and then decapitated at 0.5 minutes after injection. Blood (plasma) was removed and protein G beads were used to capture the antibody-cocaine complexes. Protein G beads were added to plasma from $^3$H-cocaine-injected animal (with NaF to inhibit cocaine degradation) and incubated. After rinsing, each of the rinse volumes and the beads were added to scintillation fluid. The $^3$H-cocaine was detected by scintillation counting. The same plasma was analyzed for degradation of cocaine as in the metabolism assay (Part E) above. Since the antibodies made after immunization with cocaine-BSA bind to cocaine and to norcocaine, but not to the other major metabolites, as demonstrated in the Examples, percent binding was calculated based on the amount of cocaine and norcocaine found in the plasma sample.

In the animals which were immunized with cocaine-BSA, an average of about 50% of the cocaine in the plasma sample was bound to antibody. This is compared to the BSA-immunized animals, in which 3% of the cocaine was bound to antibody. The 3% value represents the background in the assay.

H. Cocaine-CTB Hapten Carrier Elicits Effective Antibody

Cocaine-CTB PS-5.53 was injected into mice to determine whether it was able to elicit antibodies that would alter cocaine distribution. CTB itself was injected into groups of control mice. Mice were boosted with cocaine-CTB PS-5.53 and PS-5.70 as needed until the antibody titers were about 54,000 or greater. The methods used for immunization and assaying cocaine-specific antibody titers are described in Examples. Mice with cocaine-specific antibody titers and control mice were injected with 0.5 mg/kg $^3$H-cocaine and were decapitated 30 seconds after injection. Brain tissue and plasma was isolated and analyzed for $^3$H-cocaine content as described in part A of this Example.

The antibody produced after immunization with cocaine-CTB inhibited the distribution of cocaine to the brain significantly. For cocaine-CTB immunized compared to CTB-immunized mice there was significantly less cocaine in the brain tissue (678.8 ng/g compared to 885.4 ng/g, n=6, p=0.0004 by two-tailed t-test). Likewise, the cocaine was retained in the plasma of cocaine-CTB to a significantly greater extent than in the CTB-immunized animals. Therefore the cocaine-CTB is effective in generating antibody that will inhibit the distribution of cocaine to the brain.

EXAMPLE 24

Passive Transfer of Immune Immunoglobulin in Mice

Mice are immunized with PS-5-CTB using optimal immunization regimens as described in the Examples. At varying times, mice are bled and the titers of anti-cocaine antibody are assessed by ELISA. Animals with antibody titers of about 54,000 or greater are sacrificed and bled by cardiac puncture. Control mice are immunized with the carrier protein alone. Serum from multiple mice (at least 20) are pooled and the IgG fraction are isolated by ammonium sulfate precipitation. Following dialysis to remove the ammonium sulfate, the level of cocaine-specific antibody in the pooled immunoglobulin fraction is quantified by ELISA. Varying amounts of immunoglobulin are administered i.p. or i.v. to naive mice. After 24 hours, the recipient mice are bled and the serum assayed to determine the level of cocaine-specific antibody. Using this method, the amount of antibody that must be transferred to achieve a given titer is determined. Groups of mice are given immune immunoglobulin and bled at varying periods of time to determine the clearance rate of the antigen-specific antibody. Other groups of mice are challenged with radiolabelled cocaine, as described in the Examples, and cocaine distribution to the brain are measured. Control mice are received IgG from carrier-immunized mice. These experiments demonstrate the ability of passively transferred immune immunoglobulin to inhibit cocaine entry into the brain.

EXAMPLE 25

Passive Transfer of Immune Immunoglobulin in Humans

A pool of human donors is immunized with PS-5-CTB or other conjugates of the invention using optimal immunization regimens as described in the Examples. At various times, donors are bled by venipuncture and the titers of anti-cocaine antibody are assayed by ELISA. Hyperimmune plasma from multiple donors is pooled and the IgG fraction is isolated by cold alcohol fractionation. The antibody preparation is buffered, stabilized, preserved and standardized as needed for hyperimmune antibody preparations for human use. The level of anti-cocaine antibody is standardized by ELISA or other antibody-based assay.

An appropriate dose of purified antibody is administered to patients intramuscularly or intravenously with or without the cocaine-CTB vaccine, but not in the same anatomical site as the vaccine. The appropriate dose is determined by assaying serum levels of recipients in a trail patient population by ELISA or other antibody-based assay at 24 hours or other appropriate time point after injection of the hyperimmune antibody preparation and/or assaying the effectiveness of different doses in inhibiting cocaine effects.

The passively transferred immune globulin inhibits cocaine effects in the patients. The use of human donors, polyclonal antibody, and the large number of donors in the donor pool limits the chance of immune response by the patients to the transferred antibody. This demonstrates that the cocaine-CTB elicits antibodies in a donor pool that can be used to passively immunize patients against the effects of cocaine.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. An antibody produced in response to a hapten-carrier conjugate comprising the structure shown in FIG. 1B, wherein B is $OCOC_6H_5$, and A, C, D, E, and F are each independently selected from the group consisting of chemical moieties, said chemical moieties are identified by CJ reference number:

| | |
|---|---|
| CJ0 | Q |
| CJ1 | $(CH_2)_nQ$ |
| CJ1.1 | $CO_2Q$ |
| CJ1.2 | COQ |
| CJ1.3 | $OCH_3$ |
| CJ2 | $OCO(CH_2)_nQ$ |
| CJ2.1 | OCOCH=Q |
| CJ2.2 | OCOCH(O) |
| CJ2.3 | $OCO(CH_2)_nCH(O)CH_2$ |
| CJ3 | $CO(CH_2)_nCOQ$ |
| CJ3.1 | $CO(CH_2)_nCNQ$ |
| CJ4 | $OCO(CH_2)_nCOQ$ |
| CJ4.1 | $OCO(CH_2)_nCNQ$ |
| CJ5 | $CH_2OCO(CH_2)_nCOQ$ |
| CJ5.1 | $CH_2OCO(CH_2)_nCNQ$ |
| CJ6 | $CONH(CH_2)_nQ$ |
| CJ7 | $Y(CH_2)_nQ$ |
| CJ7.1 | $CH_2Y(CH_2)_nQ$ |
| CJ8 | $OCOCH(OH)CH_2Q$ |
| CJ8.1 | $OCO(CH_2)_nCH(OH)CH_2Q$ |
| CJ9 | $OCOC_6H_5$ and |
| CJ10 | See FIG. 2b | wherein Y is sulfur (S), oxygen (O), or an amine (NH), wherein n is an integer from 3 to 20, and wherein Q is selected from the group consisting of: H, OH, $OCH_3$, $CH_2$, $CH_3$, COOH, halogens, activated esters, mixed anhydrides, acyl halides, acyl azides, alkyl halides, N-maleimides, imino esters, isocyanate, isothiocyanate, and T cell epitope-containing carriers; with the proviso that at least one of A, C, D, E, and F comprises a carrier containing at least one T cell epitope, said carrier is selected from the group consisting of cholera toxin B (CTB), diphtheria toxin, tetanus toxoid, pertussis toxin, ricin B subunit, retrovirus nucleoprotein (retro NP), rabies ribonucleoprotein (rabies RNP), Tobacco Mosaic Virus, and vesicular stomatitis virus-nucleocapsid protein (VSV-N).

2. The antibody of claim 1 which is a polyclonal antibody.

3. The antibody of claim 1 which is specific for the hapten portion of the conjugate.

4. An antibody produced in response to a hapten-carrier conjugate selected from the group consisting of PS-2, PS-4, PS-5 and PS-6.

5. The antibody of claim 4 wherein said carrier consists of at least one T cell epitope, said carrier is selected from the group consisting of cholera toxin B (CTB), diphtheria toxin, tetanus toxoid, pertussis toxin, ricin B subunit, retrovirus nucleoprotein (retro NP), rabies ribonucleoprotein (rabies RNP), Tobacco Mosaic Virus, and vesicular stomatitis virus-nucleocapsid protein (VSV-N).

6. The antibody of claim 4 which is a polyclonal antibody.

7. The antibody of claim 4 which is specific for the hapten portion of the conjugate.

8. An antibody produced in response to a hapten-carrier conjugate consisting of PS-5 conjugated to cholera toxin B (CTB).

* * * * *

UNITED STATES PATENT AND TRADEMARK OFFICE
CERTIFICATE OF CORRECTION

PATENT NO. : 5,760,184
DATED : June 2, 1998
INVENTOR(S) : Swain et al.

It is certified that error appears in the above-identified patent and that said Letters Patent is hereby corrected as shown below:

On the title page, item [73], please remove "Assignee: ImmuLogic, Inc., Waltham, Mass." and replace with --Assignee: ImmuLogic Pharmaceutical Corporation, Waltham, Mass.--.

Signed and Sealed this

Seventh Day of December, 1999

Attest:

Q. TODD DICKINSON

*Attesting Officer*  Acting Commissioner of Patents and Trademarks

UNITED STATES PATENT AND TRADEMARK OFFICE
CERTIFICATE OF CORRECTION

PATENT NO. : 5,760,184
DATED : June 2, 1998
INVENTOR(S) : Swain, et al

It is certified that error appears in the above-identified patent and that said Letters Patent is hereby corrected as shown below:

On the title page, item [73], delete

"Assignee: ImmuLogic, Inc., Waltham, Mass." and replace with --Assignee: ImmuLogic Pharmaceutical Corporation, Waltham, Mass.--.

Signed and Sealed this

Twenty-eighth Day of March, 2000

Attest:

Q. TODD DICKINSON

Attesting Officer     Commissioner of Patents and Trademarks